US008529902B2

(12) United States Patent
Teeling et al.

(10) Patent No.: US 8,529,902 B2
(45) Date of Patent: Sep. 10, 2013

(54) HUMAN MONOCLONAL ANTIBODIES AGAINST CD20

(75) Inventors: Jessica Teeling, Southampton (GB); Sigrid Ruuls, De Bilt (NL); Martin Glennie, Southampton (GB); Jan G. J. van de Winkel, Zeist (NL); Paul Parren, Odyk (NL); Jørgen Petersen, Rungsted Kyst (DK); Ole Baadsgaard, Malmo (SE); Haichun Huang, Fremont, CA (US)

(73) Assignee: Genmab A/S, Copenhagen (DK)

( * ) Notice: Subject to any disclaimer, the term of this patent is extended or adjusted under 35 U.S.C. 154(b) by 2481 days.

(21) Appl. No.: 10/687,799

(22) Filed: Oct. 17, 2003

(65) Prior Publication Data

US 2004/0167319 A1 Aug. 26, 2004

Related U.S. Application Data

(60) Provisional application No. 60/419,163, filed on Oct. 17, 2002, provisional application No. 60/460,028, filed on Apr. 2, 2003.

(51) Int. Cl.
| | |
|---|---|
| C07K 16/18 | (2006.01) |
| C07K 16/28 | (2006.01) |
| C07K 16/30 | (2006.01) |
| A61K 39/395 | (2006.01) |
| C12N 5/12 | (2006.01) |

(52) U.S. Cl.
USPC ........... 424/144.1; 424/133.1; 424/139.1; 424/153.1; 424/155.1; 424/173.1; 424/174.1; 424/800; 424/801; 435/326; 435/328; 435/331; 435/334; 435/343.1; 435/344; 435/344.1; 530/387.3; 530/387.9; 530/388.15; 530/388.22; 530/388.73; 530/388.8; 530/388.85; 530/806; 530/867

(58) Field of Classification Search
None
See application file for complete search history.

(56) References Cited

U.S. PATENT DOCUMENTS

| | | |
|---|---|---|
| 5,182,368 A | 1/1993 | Ledbetter et al. |
| 5,247,069 A | 9/1993 | Ledbetter et al. |
| 5,506,126 A | 4/1996 | Seed et al. |
| 5,540,926 A | 7/1996 | Aruffo et al. |
| 5,595,721 A | 1/1997 | Kaminski et al. |
| 5,658,570 A | 8/1997 | Newman et al. |
| 5,681,722 A | 10/1997 | Newman et al. |
| 5,693,780 A | 12/1997 | Newman et al. |
| 5,736,137 A | 4/1998 | Anderson et al. |
| 5,750,105 A | 5/1998 | Newman et al. |
| 5,756,096 A | 5/1998 | Newman et al. |
| 5,770,429 A | 6/1998 | Lonberg et al. |
| 5,776,456 A | 7/1998 | Anderson et al. |
| 5,786,456 A | 7/1998 | Ledbetter et al. |
| 5,830,731 A | 11/1998 | Seed et al. |
| 5,843,398 A | 12/1998 | Kaminski et al. |
| 5,843,439 A | 12/1998 | Anderson et al. |
| 5,849,898 A | 12/1998 | Seed et al. |
| 5,945,513 A | 8/1999 | Aruffo et al. |
| 6,015,542 A | 1/2000 | Kaminski et al. |
| 6,090,365 A | 7/2000 | Kaminski et al. |
| 6,096,878 A | 8/2000 | Honjo et al. |
| 6,111,093 A | 8/2000 | Seed et al. |
| 6,120,767 A | 9/2000 | Robinson et al. |
| 6,136,310 A | 10/2000 | Hanna et al. |
| 6,183,744 B1 | 2/2001 | Goldenberg |
| 6,218,525 B1 | 4/2001 | Seed et al. |
| 6,224,866 B1 | 5/2001 | Barbera-Guillem |
| 6,287,537 B1 | 9/2001 | Kaminski et al. |
| 6,306,393 B1 | 10/2001 | Goldenberg |
| 6,399,061 B1 | 6/2002 | Anderson et al. |
| 6,455,043 B1 | 9/2002 | Grillo-López |
| 2001/0018041 A1 | 8/2001 | Hanna et al. |
| 2001/0033839 A1 | 10/2001 | Barbera-Guillem |
| 2001/0056066 A1 | 12/2001 | Bugelski et al. |
| 2002/0006404 A1 | 1/2002 | Hanna et al. |
| 2002/0009427 A1 | 1/2002 | Wolin et al. |
| 2002/0009444 A1 | 1/2002 | Grillo-López |
| 2002/0012665 A1 | 1/2002 | Hanna |
| 2002/0028178 A1 | 3/2002 | Hanna et al. |
| 2002/0039557 A1 | 4/2002 | White |
| 2002/0041847 A1 | 4/2002 | Goldenberg |
| 2002/0048550 A1 | 4/2002 | Vallera et al. |

(Continued)

FOREIGN PATENT DOCUMENTS

| | | |
|---|---|---|
| WO | WO 88/04936 A1 | 7/1988 |
| WO | WO 92/03918 A1 | 3/1992 |

(Continued)

OTHER PUBLICATIONS

Rudikoff et al. "Single amino acid substitution altering antigen binding specificity", Proceedings of the National Academy of Sciences, 1982. vol. 79, pp. 1979-1983.*

(Continued)

Primary Examiner — Ronald Schwadron
(74) Attorney, Agent, or Firm — Finnegan, Henderson, Farabow, Garrett & Dunner, L.L.P.

(57) ABSTRACT

Isolated human monoclonal antibodies which bind to and inhibit human CD20, and related antibody-based compositions and molecules, are disclosed. The human antibodies can be produced by a transfectoma or in a non-human transgenic animal, e.g., a transgenic mouse, capable of producing multiple isotypes of human monoclonal antibodies by undergoing V-D-J recombination and isotype switching. Also disclosed are pharmaceutical compositions comprising the human antibodies, non-human transgenic animals and hybridomas which produce the human antibodies, and therapeutic and diagnostic methods for using the human antibodies.

5 Claims, 65 Drawing Sheets

(56) References Cited

U.S. PATENT DOCUMENTS

| | | | |
|---|---|---|---|
| 2002/0058029 | A1 | 5/2002 | Hanna |
| 2002/0064823 | A1 | 5/2002 | Welcher et al. |
| 2002/0071807 | A1 | 6/2002 | Goldenberg |
| 2002/0128448 | A1 | 9/2002 | Reff |
| 2002/0150580 | A1 | 10/2002 | Newman et al. |
| 2002/0159996 | A1 | 10/2002 | Hariharan et al. |

FOREIGN PATENT DOCUMENTS

| | | | |
|---|---|---|---|
| WO | WO 93/02108 A1 | | 2/1993 |
| WO | WO 94/11026 A2 | | 5/1994 |
| WO | WO-94/11026 A2 | | 5/1994 |
| WO | WO 94/11026 A3 | | 5/1994 |
| WO | WO 94/25585 A1 | | 11/1994 |
| WO | WO 96/33735 | | 10/1996 |
| WO | WO 97/09351 A1 | | 3/1997 |
| WO | WO 98/04281 A1 | | 2/1998 |
| WO | WO 98/24884 A1 | | 6/1998 |
| WO | WO 98/42378 A1 | | 10/1998 |
| WO | WO 99/14353 A2 | | 3/1999 |
| WO | WO 99/14353 A3 | | 3/1999 |
| WO | WO 99/33485 A1 | | 7/1999 |
| WO | WO 00/03733 A1 | | 1/2000 |
| WO | WO 00/09160 A1 | | 2/2000 |
| WO | WO-00/09160 A1 | | 2/2000 |
| WO | WO 00/20864 A1 | | 4/2000 |
| WO | WO 00/27428 A1 | | 5/2000 |
| WO | WO 00/27433 A1 | | 5/2000 |
| WO | WO 00/67796 A1 | | 11/2000 |
| WO | WO 00/74718 A1 | | 12/2000 |
| WO | WO 01/03734 A1 | | 1/2001 |
| WO | WO 01/10460 A1 | | 2/2001 |
| WO | WO 01/10462 A1 | | 2/2001 |
| WO | WO 01/14424 | * | 3/2001 |
| WO | WO 01/34194 A1 | | 5/2001 |
| WO | WO 01/57226 A1 | | 8/2001 |
| WO | WO 01/72333 A1 | | 10/2001 |
| WO | WO 01/74388 A1 | | 10/2001 |
| WO | WO 01/80884 A1 | | 11/2001 |
| WO | WO 01/97843 A2 | | 12/2001 |
| WO | WO 01/97843 A3 | | 12/2001 |
| WO | WO 01/97858 A2 | | 12/2001 |
| WO | WO 01/97858 A3 | | 12/2001 |
| WO | WO 02/04021 A1 | | 1/2002 |
| WO | WO 02/07783 A2 | | 1/2002 |
| WO | WO 02/07783 A3 | | 1/2002 |
| WO | WO 02/12437 A2 | | 2/2002 |
| WO | WO 02/12437 A3 | | 2/2002 |
| WO | WO 02/22212 A2 | | 3/2002 |
| WO | WO 02/22212 A3 | | 3/2002 |
| WO | WO 02/34790 A1 | | 5/2002 |
| WO | WO 02/43478 A2 | | 6/2002 |
| WO | WO 02/060484 A1 | | 8/2002 |
| WO | WO 02/060485 A2 | | 8/2002 |
| WO | WO 02/060485 A3 | | 8/2002 |
| WO | WO 02/062946 A2 | | 8/2002 |
| WO | WO 02/062946 A3 | | 8/2002 |
| WO | WO 02/079255 A1 | | 10/2002 |
| WO | WO 2004/035607 A2 | | 4/2004 |
| WO | WO 2009/086072 A2 | | 7/2009 |

OTHER PUBLICATIONS

MacCallum et al. "Antibody-antigen interactions: contact analysis and binding site topography", Journal of Molecular Biology, 1996. vol. 262, pp. 732-745.*

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

Edwards, J.C.W. et al, "Sustained improvement in rheumatoid arthritis following a protocol designed to deplete B lymphocytes," *Rheumatology*, vol. 40:205-211 (2001).

Gazzano-Santoro, Hélène et al, "A non-radioactive complement-dependent cytotoxicity assay for anti-CD20 monoclonal antibody," *Journal of Immunological Methods*, vol. 202:163-171 (1997).

van Spriel, Annemiek B. et al, "Immunotherapeutic perspective for bispecific antibodies," *Immunology Today*, vol. 21(8):391-397 (2000).

Coiffier, Bertrand, "Monoclonal antibodies combined to chemotherapy for the treatment of patients with lymphoma," *Blood Reviews*, 17: pp. 25-31 (2003).

Teeling, Jessica L., et al., "Characterization of new human CD20 monoclonal antibodies with potent cytolytic activity against non-Hodgkin lymphomas," *Blood*, vol. 104(6); pp. 1793-1800 (Sep. 15, 2004).

Johnson, PWM, et al., "Rituximab: mechanisms and applications," *British Journal of Cancer*, 85(11): pp. 1619-1623 (2001).

Dechant, Michael, et al., "Novel Fully Human CD20 Antibodies with Different Mechanisms of Actions", Abstract #349, p. 103a: Simultaneous Session: Clinicopathologic and Molecular Factors Impacting Prognosis (11:00 AM-12:30 PM), Dec. 8, 2003.

Foran, J.M., "Antibody-based therapy of non-Hodgkin's lymphoma", *Best Practice & Research Clinical Haematology*, 15(3): 449-465 (2002).

Tamura, M., et al., "Structural Correlates of an Anticarcinoma Antibody: Identification of Specificity-Determining Residues (SDRs) and Development of a Minimally Immunugenic Antibody Variant by Retention of SDRs Only", *J Immunol*, 164: 1432-1441 (Feb. 23, 2011).

Fishwild, D., et al., "High-avidity human IgGk monoclonal antibodies from a novel strain of minilocus transgenic mice," *Nature Biotechnology*, 14:845-851 (1996).

Teeling, J., et al., "The Biological Activity of Human CD20 Monoclonal Antibodies Is Linked to Unique Epitopes on CD20", *The Journal of Immunology*, 177:362-371 (2006).

Kagami, Y., "Mechanism of action of anti-tumor effect by rituximab," *Hematology & Oncology*, 44(4) 264-271 (Apr. 2002) (English abstract attached).

Patentee's Response to the Opposition of Actavis Group Plc., dated Mar. 22, 2013, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20) (13 pages).

Declaration of Dr. Tom Vink dated Aug. 6, 2009, submitted to the European Patent Office on Mar. 22, 2013 as exhibit D10, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20) (17 pages).

European Search Report for corresponding European Application No. 03809145.0 based on PCT/US03/33057, received Jan. 3, 2006 (international filing date, Oct. 17, 2003, inventors Teeling et al., applicant Genmab A/S, title: Human Monoclonal Antibodies Against CD20).

International Search Report for corresponding International Application No. PCT/US03/33057, mailed May 27, 2004 (international filing date, Oct. 17, 2003, inventors Teeling et al., applicant Genmab A/S, title: Human Monoclonal Antibodies Against CD20).

Notice of Allowance for U.S. Appl. No. 11/578,818, mailed Aug. 9, 2010 (U.S. filing date, May 29, 2008; inventors Teeling et al., assignee Genmab A/S, title: Human Monoclonal Antibodies Against CD20).

Notice of Allowability for U.S. Appl. No. 11/578,818, mailed Oct. 18, 2010 (U.S. filing date, May 29, 2008; inventors Teeling et al., assignee Genmab A/S, title: Human Monoclonal Antibodies Against CD20).

Opposition in the name of Actavis Group Plc., dated Oct. 11, 2012, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20).

Exhibit D6a (Sequence Alignment between SEQ ID No:97 of U.S. Patent No. 6,096,878 and SEQ ID No:2 of U.S. Application No. 10/687,799) of the Opposition in the name of Actavis Group Plc., dated Oct. 11, 2012, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20).

Exhibit D7a (Sequence Alignment between SEQ ID No:88 of WO 01/57226 and SEQ ID No:2 of U.S. Appl. No. 10/687,799) of the Opposition in the name of Actavis Group Plc., dated Oct. 11, 2012, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20).

Exhibit D8a (Sequence Alignment between Accession No. BACO2018 and SEQ ID No:2 of U.S. Appl. No. 10/687,799) of the Opposition in the name of Actavis Group Plc., dated Oct. 11, 2012, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20).

Exhibit D8b (Sequence Alignment between Accession No. S23628 and SEQ ID No:4 of U.S. Appl. No. 10/687,799) of the Opposition in the name of Actavis Group Plc., dated Oct. 11, 2012, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20).

Exhibit D8c (Sequence Alignment between Accession No. AAK94935 and SEQ ID No:4 of U.S. Appl. No. 10/687,799) of the Opposition in the name of Actavis Group Plc., dated Oct. 11, 2012, in corresponding European Patent No. EP 1 558 648 (Application No. 03809145.0, international filing date, Oct. 17, 2003, inventors Teeling et al., applicant Genmab A/S, title: Human Monoclonal Antibodies Against CD20).

Wu, A. et al., "Multimerization of action of anti-tumor effect by rituximab," *Hematology & Oncology*, 44(4) 264-271 (Apr. 2002) (English abstract attached).

* cited by examiner

Homotypic adhesion of Ramos cells.

Translation of 2F2 VH
E VQLVESGGGL VQPGRSLRLS CAASGFTFND
YAMHWVRQAP GKGLEWVSTI SWNSGSIGYA DSVKGRFTIS RDNAKKSLYL
QMNSLRAEDT ALYYCAKDIQ YGNYYYGMDY WGQGTTVTVS S
Translation of 2F2VL
EIVLTQSPAT LSLSPGERAT LSCRASQSVS
SYLAWYQQKP GQAPRLLIYD ASNRATGIPA RFSGSGSGTD FTLTISSLEP
EDFAVYYCQQ RSNWPIT FGQ GTRLEIK
 CDR1
 CDR2
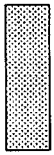 CDR3
*Fig. 53*

2F2 VH

```
  1  ATGGAG TTGGGA CTGAGC TGGATT TTCCTT TTGGCT ATTTTA AAAGGT GTCCAG
 55  TGTGAA GTGCAG CTGGTG GAGTCT GGGGGA GGCTTG GTACAG CCTGGC AGGTCC
109  CTGAGA CTCTCC TGTGCA GCCTCT GGATTC ACCTTT AATGAT TATGCC ATGCAC
163  TGGGTC CGGCAA GTTCCA GGGAAG GGCCTG GAGTGG GTCTCA ACTATT AGTTGG
217  AATAGT GGTTCC ATAGGC TATGCG GACTCT GTGAAG GGCCGA TTCACC ATCTCC
271  AGAGAC AACGCC AAGAAC TCCCTG TATCTG CAAATG AACAGT CTGAGA GCTGAG
325  GACACG GCCTTG TATTAC TGTGCA AAAGAT ATACAG TACGGC AACTAC TACTAC
379  GGTATG GACGTC TGGGGC CAAGGG ACCACG GTCACC GTCTCC TCAG
```

2F2VL

```
  1  ATGGAA GCCCCA GCTCAG CTTCTC TTCCTC CTGCTA CTCTGG CTCCCA GATACC
 55  ACCGGA GAAATT GTGTTG ACACAG TCTCCA GCCACC CTGTCT TTGTCT CCAGGG
109  GAAAGA GCCACC CTCTCC TGCAGG GCCAGT CAGAGT GTTAGC AGCTAC TTAGCC
163  TGGTAC CAACAG AAACCT GGCCAG GCTCCC AGGCTC CTCATC TATGAT GCATCC
217  AACAGG GCCACT GGCATC CCAGCC AGGTTC CGTGGC AGTGGG TCTGGG ACAGAC
271  TTCACT CTCACC ATCAGC AGCCTA GAGCCT GAAGAT TTTGCA GTTTAT TACTGT
325  CAGCAG CGTAGC AACTGG CCGATC ACCTTC GGCCAA GGGACA CGACTG GAGATT
379  AAAC
```

*Fig. 54*

Translation of 7D8VH

E VQLVESGGGL VQPDRSLRLS CAASGFTFHD
YAMHWVRQAP GKGLEWVSTI SWNSGTIGYA DSVKGRFTIS RDNAKNSLYL
QMNSLRAEDT ALYYCAKDLQ YGN YYGMDY WGQGTTVTVS S

Translation of 7D8VL

EIVLTQSPAT LSLSPGERAT LSCRASQSVS
SYLAWYQQKP GQAPRLLIYD ASNRATGIPA RFSGSGSGTD FTLTISSLEP
EDFAVYYCQQ RSNWPITFGQ GTRLEIK

▨ CDR1
☐ CDR2
▓ CDR3

```
  1  ATGGAG TTGGGA CTGAGC TGGATT TTCCTT TTGGCT ATTTTA AAAGGT GTCCAG
 55  TGTGAA GTGCAG CTGGTG GAGTCT GGGGGA GGCTTG GTACAG CCTGAC AGGTCC
109  CTGAGA CTCTCC TGTGCA GCCTCT GGATTC ACCTTT CATGAT TATGCC ATGCAC
163  TGGGTC CGGCAA GCTCCA GGGAAG GGCCTG GAGTGG GTCTCA ACTATT AGTTGG
217  AATAGT GGTACC ATAGGC TATGCG GACTCT GTGAAG GGCCGA TTCACC ATCTCC
271  AGAGAC AACGCC AAGAAC TCCCTG TATCTG CAAATG AACAGT CTGAGA GCTGAG
325  GACACG GCCTTG TATTAC TGTGCA AAAGAT ATACGG AACTAC TACTAC
379  GGTATG GACGTC TGGGGC CAAGGG ACCACG GTCACC GTCTCC TCAG
```

7D8VH

```
  1  ATGGAA GCCCCA GCTCAG CTTCTC TTCCTC CTGCTA CTCTGG CTCCCA GATACC
 55  ACCGGA GAAATT GTGTTG ACACAG TCTCCA GCCACC CTGTCT TTGTCT CCAGGG
109  GAAAGA GCCACC CTCTCC TGCAGG GCCAGT CAGAGT GTTAGC AGCTAC TTAGCC
163  TGGTAC CAACAG AAACCT GGCCAG GCTCCC AGGCTC CTCATC TATGAT GCATCC
217  AACAGG GCCACT GGCATC CCAGCC AGGTTC AGTGGC AGTGGG TCTGGG ACAGAC
271  TTCACT CTCACC ATCAGC AGCCTA GAGCCT GAAGAT TTTGCA GTTTAT TACTGT
325  CAGCAG CGTAGC AACTGG CCGATC ACCTTC GGCCAA GGGACA CGACTG GAGATT
379  AAAC
```

*Fig. 56*

Translation of VHCD2011B8

```
E VQLVQSGGGL VHPGGSLRLS CTGSGFTFSY
HAMHWVRQAP GKGLEWVSI IGTGGVTYYAD SVKGRFTISR DNVKNSLYLQ
MNSLRAEDMA VYYCARDYYC ACSFYDC YG MDVWGQGTTV TVSS
```

Translation of VLCD2011B8

```
EIVLTQSPAT LSLSPGERAT LSCRASQSVS
SYLAWYQQKP GQAPRLLIYD ASNRATGIPA RFSGSGSGTD FTLTISSLEP
EDFAVYYCQQ RSDWPLT FGG GTKVEIK
```

CDR1
CDR2
CDR3

*Fig. 57*

VHCD2011B8

```
  1 ATGGAG TTGGGG CTGAGC CTGGTG TGTACA GGCTCT GGGGGA GGCTTG GTACAT CCTGGG GGGTCC
 55 TGTGAG GTTCAG CTCTCC TGTACA GGCTCT GGATTC ACCTTC AGTTAC CATGCT ATGCAT
109 CTGAGA CGCCAG GTCACA GCTCCA GGAAAA GGTCTG GAATGG GTATCA ATTATT GGGACT
163 TGGGTT CGCCAG GTCACA TACTAT AACTCC TCCGTG AAGGGC CGATTC ACCATC TCCAGA
217 GGTGGT GTCAGA GTCAAG AACTCC TTGTAT CTTCAA ATGAAC AGCCTG AGAGCC GAGGAC
271 GACAAT GTGTAT TACTGT GCAAGA GATTAC TATGGT GCGGGG AGTTTT TATGAC
325 ATGGCT GTGTAT TACTGT ATGGAT GTCTGG GGCCAA GGGACC ACGGTC ACCGTC TCCTCA
379 GGCCTC TACGGT ATGGAT GTCTGG GGCCAA GGGACC ACGGTC ACCGTC TCCTCA
433 G
```

VLCD2011B8

```
  1 ATGGAA GCCCCA GCACAG CTTCTC TTCCTC CTGCTA CTCTGG CTCCCA GATACC
 55 ACCGGA GAAATT GTGTTG ACACAG TCTCCA GCCACC CTGTCT TTGTCT CCAGGG
109 GAAAGA GCCACC CTCTCC TGCAGG GCCAGT CAGAGT GTTAGC AGCTAC TTAGCC
163 TGGTAC CAACAG AAACCT GGCCAG GCTCCC AGGCTC CTCATC TATGAT GCATCC
217 AACAGG GCCACT GGCATC CCAGCC AGGTTC AGTGGC AGTGGG TCTGGG ACAGAC
271 TTCACT CTCACC ATCAGC AGCCTA GAGCCT GAAGAT TTTGCA GTTTAT TACTGT
325 CAGCAG CGTAGC GACTGG CCGCTC ACTTTC GGCGGA GGGACC AAGGTG GAGATC
379 AAAC
```

*Fig. 58*

SEQUENCE LISTING

<160> NUMBER OF SEQ ID NOS: 95

<210> SEQ ID NO 1
<211> LENGTH: 424
<212> TYPE: DNA
<213> ORGANISM: Homo sapiens

<400> SEQUENCE: 1

| | | | | | |
|---|---|---|---|---|---|
| atggagttgg | gactgagctg | gattttcctt | ttggctattt | taaaaggtgt | ccagtgtgaa | 60 |
| gtgcagctgg | tggagtctgg | gggaggcttg | gtacagcctg | gcaggtccct | gagactctcc | 120 |
| tgtgcagcct | ctggattcac | ctttaatgat | tatgccatgc | actgggtccg | gcaagctcca | 180 |
| gggaagggcc | tggagtgggt | ctcaactatt | agttggaata | gtggttccat | aggctatgcg | 240 |
| gactctgtga | agggccgatt | caccatctcc | agagacaacg | ccaagaagtc | cctgtatctg | 300 |
| caaatgaaca | gtctgagagc | tgaggacacg | gccttgtatt | actgtgcaaa | agatatacag | 360 |
| tacggcaact | actactacgg | tatggacgtc | tggggccaag | ggaccacggt | caccgtctcc | 420 |
| tcag | | | | | | 424 |

<210> SEQ ID NO 2
<211> LENGTH: 122
<212> TYPE: PRT
<213> ORGANISM: Homo sapiens

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 3
<211> LENGTH: 382
<212> TYPE: DNA
<213> ORGANISM: Homo sapiens

<400> SEQUENCE: 3

| | | | | | |
|---|---|---|---|---|---|
| atggaagccc | cagctcagct | tctcttcctc | ctgctactct | ggctcccaga | taccaccgga | 60 |
| gaaattgtgt | tgacacagtc | tccagccacc | ctgtctttgt | ctccagggga | aagagccacc | 120 |
| ctctcctgca | gggccagtca | gagtgttagc | agctacttag | cctggtacca | acagaaacct | 180 |
| ggccaggctc | ccaggctcct | catctatgat | gcatccaaca | gggccactgg | catcccagcc | 240 |
| aggttcagtg | gcagtgggtc | tgggacagac | ttcactctca | ccatcagcag | cctagagcct | 300 |
| gaagattttg | cagtttatta | ctgtcagcag | cgtagcaact | ggccgatcac | cttcggccaa | 360 | gggacacgac tggagattaa ac                                              382

<210> SEQ ID NO 4
<211> LENGTH: 107
<212> TYPE: PRT
<213> ORGANISM: Homo sapiens

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 5
<211> LENGTH: 424
<212> TYPE: DNA
<213> ORGANISM: Homo sapiens

<400> SEQUENCE: 5
atggagttgg gactgagctg gatttccctt ttggctattt taaaaggtgt ccagtgtgaa    60
gtgcagctgg tggagtctgg gggaggcttg gtacagcctg acaggtccct gagactctcc   120
tgtgcagcct ctggattcac ctttcatgat tatgccatgc actgggtccg gcaagctcca   180
gggaagggcc tggagtgggt ctcaactatt agttggaata gtggtaccat aggctatgcg   240
gactctgtga agggccgatt caccatctcc agagacaacg ccaagaactc cctgtatctg   300
caaatgaaca gtctgagagc tgaggacacg gccttgtatt actgtgcaaa agatatacag   360
tacggcaact actactacgg tatggacgtc tggggccaag ggaccacggt caccgtctcc   420
tcag                                                                424

<210> SEQ ID NO 6
<211> LENGTH: 122
<212> TYPE: PRT
<213> ORGANISM: Homo sapiens

<400> SEQUENCE: 6

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

```
Ala Lys Asp Ile Gln Tyr Gly Asn Tyr Tyr Tyr Gly Met Asp Val Trp
            100                 105                 110
Gly Gln Gly Thr Thr Val Thr Val Ser Ser
            115                 120

<210> SEQ ID NO 7
<211> LENGTH: 382
<212> TYPE: DNA
<213> ORGANISM: Homo sapiens

<400> SEQUENCE: 7
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaact ggccgatcac cttcggccaa     360
gggacacgac tggagattaa ac                                              382

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
  1               5                  10                  15
Glu Arg Ala Thr Leu Ser Cys Arg Ala Ser Gln Ser Val Ser Ser Tyr
             20                  25                  30
Leu Ala Trp Tyr Gln Gln Lys Pro Gly Gln Ala Pro Arg Leu Leu Ile
         35                  40                  45
Tyr Asp Ala Ser Asn Arg Ala Thr Gly Ile Pro Ala Arg Phe Ser Gly
     50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Ile
                 85                  90                  95
Thr Phe Gly Gln Gly Thr Arg Leu Glu Ile Lys
            100                 105

<210> SEQ ID NO 9
<211> LENGTH: 433
<212> TYPE: DNA
<213> ORGANISM: Homo sapiens

<400> SEQUENCE: 9
atggagttgg ggctgagctg gttttccctt gttgctatat taaaaggtgt ccagtgtgag      60
gttcagctgg tgcagtctgg gggaggcttg gtacatcctg gggggtccct gagactctcc     120
tgtacaggct ctggattcac cttcagttac atgctatgca ttgggttcg ccaggctcca     180 ggaaaaggtc tggaatgggt atcaattatt gggactggtg gtgtcacata ctatgcagac     240
tccgtgaagg gccgattcac catctccaga gacaatgtca agaactcctt gtatcttcaa     300
atgaacagcc tgagagccga ggacatggct gtgtattact gtgcaagaga ttactatggt     360
gcggggagtt tttatgacgg cctctacggt atggacgtct ggggccaagg gaccacggtc     420
```
accgtctcct cag                                                          433

<210> SEQ ID NO 10
<211> LENGTH: 125
<212> TYPE: PRT
<213> ORGANISM: Homo sapiens

<400> SEQUENCE: 10

Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
            20                  25                  30

Ala Met His Trp Val Arg Gln Ala Pro Gly Lys Gly Leu Glu Trp Val
        35                  40                  45

Ser Ile Ile Gly Thr Gly Gly Val Thr Tyr Tyr Ala Asp Ser Val Lys
    50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser
        115                 120                 125

<210> SEQ ID NO 11
<211> LENGTH: 382
<212> TYPE: DNA
<213> ORGANISM: Homo sapiens

<400> SEQUENCE: 11
atggaagccc cagcacagct tctcttcctc ctgctactct ggctcccaga taccaccgga    60
gaaattgtgt tgacacagtc tccagccacc ctgtctttgt ctccagggga agagccacc    120 ctctcctgca gggccagtca gagtgttagc agctacttag cctggtacca acagaaacct   180
ggccaggctc ccaggctcct catctatgat gcatccaaca gggccactgg catcccagcc   240
aggttcagtg gcagtgggtc tgggacagac ttcactctca ccatcagcag cctagagcct   300
gaagattttg cagtttatta ctgtcagcag cgtagcgact ggccgctcac tttcggcgga   360
gggaccaagg tggagatcaa ac                                            382

<210> SEQ ID NO 12
<211> LENGTH: 107
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu

-continued

```
                    85                  90                  95
Thr Phe Gly Gly Gly Thr Lys Val Glu Ile Lys
            100                 105

<210> SEQ ID NO 13
<211> LENGTH: 5
<212> TYPE: PRT
<213> ORGANISM: Homo sapiens

<400> SEQUENCE: 13

Asp Tyr Ala Met His
1               5

<210> SEQ ID NO 14
<211> LENGTH: 17
<212> TYPE: PRT
<213> ORGANISM: Homo sapiens

<400> SEQUENCE: 14

Thr Ile Ser Trp Asn Ser Gly Ser Ile Gly Tyr Ala Asp Ser Val Lys
1               5                   10                  15

Gly

<210> SEQ ID NO 15
<211> LENGTH: 13
<212> TYPE: PRT
<213> ORGANISM: Homo sapiens

<400> SEQUENCE: 15

Asp Ile Gln Tyr Gly Asn Tyr Tyr Tyr Gly Met Asp Val
1               5                   10

<210> SEQ ID NO 16
<211> LENGTH: 11
<212> TYPE: PRT
<213> ORGANISM: Homo sapiens

<400> SEQUENCE: 16

Arg Ala Ser Gln Ser Val Ser Ser Tyr Leu Ala
1               5                   10

<210> SEQ ID NO 17
<211> LENGTH: 7
<212> TYPE: PRT
<213> ORGANISM: Homo sapiens

<400> SEQUENCE: 17

Asp Ala Ser Asn Arg Ala Thr
1               5

<210> SEQ ID NO 18
<211> LENGTH: 9
<212> TYPE: PRT
<213> ORGANISM: Homo sapiens

<400> SEQUENCE: 18

Gln Gln Arg Ser Asn Trp Pro Ile Thr
1               5

<210> SEQ ID NO 19
<211> LENGTH: 5
<212> TYPE: PRT
<213> ORGANISM: Homo sapiens

<400> SEQUENCE: 19
```

```
Asp Tyr Ala Met His
1               5
```

<210> SEQ ID NO 20
<211> LENGTH: 17
<212> TYPE: PRT
<213> ORGANISM: Homo sapiens

<400> SEQUENCE: 20

```
Thr Ile Ser Trp Asn Ser Gly Thr Ile Gly Tyr Ala Asp Ser Val Lys
1               5                   10                  15

Gly
```

<210> SEQ ID NO 21
<211> LENGTH: 13
<212> TYPE: PRT
<213> ORGANISM: Homo sapiens

<400> SEQUENCE: 21

```
Asp Ile Gln Tyr Gly Asn Tyr Tyr Tyr Gly Met Asp Val
1               5                   10
```

<210> SEQ ID NO 22
<211> LENGTH: 11
<212> TYPE: PRT
<213> ORGANISM: Homo sapiens

<400> SEQUENCE: 22

```
Arg Ala Ser Gln Ser Val Ser Ser Tyr Leu Ala
1               5                   10
```

<210> SEQ ID NO 23
<211> LENGTH: 7
<212> TYPE: PRT
<213> ORGANISM: Homo sapiens

<400> SEQUENCE: 23

```
Asp Ala Ser Asn Arg Ala Thr
1               5
```

<210> SEQ ID NO 24
<211> LENGTH: 9
<212> TYPE: PRT
<213> ORGANISM: Homo sapiens

<400> SEQUENCE: 24

```
Gln Gln Arg Ser Asn Trp Pro Ile Thr
1               5
```

<210> SEQ ID NO 25
<211> LENGTH: 5
<212> TYPE: PRT
<213> ORGANISM: Homo sapiens

<400> SEQUENCE: 25

```
Tyr His Ala Met His
1               5
```

<210> SEQ ID NO 26
<211> LENGTH: 16
<212> TYPE: PRT
<213> ORGANISM: Homo sapiens

<400> SEQUENCE: 26

```
Ile Ile Gly Thr Gly Gly Val Thr Tyr Tyr Ala Asp Ser Val Lys Gly
1               5                   10                  15
```

<210> SEQ ID NO 27
<211> LENGTH: 17
<212> TYPE: PRT
<213> ORGANISM: Homo sapiens

<400> SEQUENCE: 27

```
Asp Tyr Tyr Gly Ala Gly Ser Phe Tyr Asp Gly Leu Tyr Gly Met Asp
1               5                   10                  15
Val
```

<210> SEQ ID NO 28
<211> LENGTH: 11
<212> TYPE: PRT
<213> ORGANISM: Homo sapiens

<400> SEQUENCE: 28

```
Arg Ala Ser Gln Ser Val Ser Ser Tyr Leu Ala
1               5                   10
```

<210> SEQ ID NO 29
<211> LENGTH: 7
<212> TYPE: PRT
<213> ORGANISM: Homo sapiens

<400> SEQUENCE: 29

```
Asp Ala Ser Asn Arg Ala Thr
1               5
```

<210> SEQ ID NO 30
<211> LENGTH: 9
<212> TYPE: PRT
<213> ORGANISM: Homo sapiens

<400> SEQUENCE: 30

```
Gln Gln Arg Ser Asp Trp Pro Leu Thr
1               5
```

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
gcaggcacac aacagaggca gttccagatt tc                                    32

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
gctgtgcccc cagaggtgct cttggagg                                         28

<210> SEQ ID NO 33
<211> LENGTH: 20
<212> TYPE: DNA
<213> ORGANISM: Artificial Sequence
<220> FEATURE:
<223> OTHER INFORMATION: Primer

```
<220> FEATURE:
<221> NAME/KEY: variation
<222> LOCATION: (6)...(6)
<223> OTHER INFORMATION: n = T or G

<400> SEQUENCE: 33
caggtncagc tggtgcagtc                                                      20

<210> SEQ ID NO 34
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (1)...(1)
<223> OTHER INFORMATION: n= C or G
<220> FEATURE:
<221> NAME/KEY: variation
<222> LOCATION: (13)...(13)
<223> OTHER INFORMATION: n = T or G

<400> SEQUENCE: 34
naggtgcagc tgntggagtc                                                      20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gaggtgcagc tggtgcagtc                                                      20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
atggactgga cctggagcat c                                                    21

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
atggaattgg ggctgagctg                                                      20

<210> SEQ ID NO 38
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (12)...(12)
<223> OTHER INFORMATION: n = A or G

<400> SEQUENCE: 38
atggagtttg gnctgagctg                                                      20
```

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
atgaaacacc tgtggttctt c                                              21

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
atggggtcaa ccgccatcct                                                20

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
tgccaggggg aagaccgatg g                                              21

<210> SEQ ID NO 42
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (1)...(1)
<223> OTHER INFORMATION: n = A or G
<220> FEATURE:
<221> NAME/KEY: variation
<222> LOCATION: (14)...(14)
<223> OTHER INFORMATION: n = C or T

<400> SEQUENCE: 42
nacatccaga tganccagtc                                                20

<210> SEQ ID NO 43
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (2)...(2)
<223> OTHER INFORMATION: n = C or T
<220> FEATURE:
<221> NAME/KEY: variation
<222> LOCATION: (7)...(7)
<223> OTHER INFORMATION: n = C or T
<220> FEATURE:
<221> NAME/KEY: variation
<222> LOCATION: (8)...(8)
<223> OTHER INFORMATION: n = A or G

<400> SEQUENCE: 43
gncatcnnga tgacccagtc                                                20

```
<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
gatattgtga tgacccagac                                              20

<210> SEQ ID NO 45
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (15)...(15)
<223> OTHER INFORMATION: n = A or G

<400> SEQUENCE: 45
gaaattgtgt tgacncagtc                                              20

<210> SEQ ID NO 46
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: variation
<222> LOCATION: (6)...(6)
<223> OTHER INFORMATION: n = A or T
<220> FEATURE:
<221> NAME/KEY: variation
<222> LOCATION: (9)...(9)
<223> OTHER INFORMATION: n = A or G

<400> SEQUENCE: 46
gaaatngtna tgacacagtc                                              20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gatgttgtga tgacacagtc                                              20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gaaattgtgc tgactcagtc                                              20

<210> SEQ ID NO 49
<211> LENGTH: 24
<212> TYPE: DNA
<213> ORGANISM: Artificial Sequence
<220> FEATURE:
<223> OTHER INFORMATION: Primer
```

<400> SEQUENCE: 49
cccgctcagc tcctggggct cctg                                          24

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
ccctgctcag ctcctggggc tgc                                           23

<210> SEQ ID NO 51
<211> LENGTH: 26
<212> TYPE: DNA
<213> ORGANISM: Artificial Sequence
<220> FEATURE:
<223> OTHER INFORMATION: Primer

<400> SEQUENCE: 51
cccagcgcag cttctcttcc tcctgc                                        26

<210> SEQ ID NO 52
<211> LENGTH: 27
<212> TYPE: DNA
<213> ORGANISM: Artificial Sequence
<220> FEATURE:
<223> OTHER INFORMATION: Primer

<400> SEQUENCE: 52
atggaaccat ggaagcccca gcacagc                                       27

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
cgggaagatg aagacagatg                                               20

<210> SEQ ID NO 54
<211> LENGTH: 116
<212> TYPE: PRT
<213> ORGANISM: Homo sapiens

<400> SEQUENCE: 54

Met Glu Leu Gly Leu Ser Trp Val Phe Leu Val Ala Ile Leu Glu Gly
 1               5                  10                  15

Val Gln Cys Glu Val Gln Leu Val Gln Ser Gly Gly Gly Leu Val His
            20                  25                  30

Pro Gly Gly Ser Leu Arg Leu Ser Cys Ala Gly Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ser Ala Ile Gly Thr Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr

Tyr Cys Ala Arg
     115

<210> SEQ ID NO 55
<211> LENGTH: 139
<212> TYPE: PRT
<213> ORGANISM: Homo sapiens

<400> SEQUENCE: 55

Met Glu Ala Pro Ala Gln Leu Leu Phe Leu Leu Leu Trp Leu Pro
1              5                   10                15

Asp Thr Thr Gly Glu Ile Val Leu Thr Gln Ser Pro Ala Thr Leu Ser
             20                 25               30

Leu Ser Pro Gly Glu Arg Ala Thr Leu Ser Cys Arg Ala Ser Gln Ser
     35                 40               45

Val Ser Ser Tyr Leu Ala Trp Tyr Gln Gln Lys Pro Gly Gln Ala Pro
 50                 55               60

Arg Leu Leu Ile Tyr Asp Ala Ser Asn Arg Ala Thr Gly Ile Pro Ala
65               70                 75               80

Arg Phe Ser Gly Ser Gly Ser Gly Thr Asp Phe Thr Leu Thr Ile Ser
             85                 90               95

Ser Leu Glu Pro Glu Asp Phe Ala Val Tyr Tyr Cys Gln Gln Arg Ser
            100               105              110

Asn Trp Pro Leu Thr Phe Gly Gly Gly Thr Lys Val Glu Ile Lys Arg
         115               120              125

Thr Val Ala Ala Pro Ser Val Phe Ile Phe Pro
    130               135

<210> SEQ ID NO 56
<211> LENGTH: 141
<212> TYPE: PRT
<213> ORGANISM: Homo sapiens

<400> SEQUENCE: 56

Met Glu Leu Gly Leu Ser Trp Ile Phe Leu Leu Ala Ile Leu Lys Gly
1              5                   10                15

Val Gln Cys Glu Val Gln Leu Val Glu Ser Gly Gly Gly Leu Val Gln
             20                 25               30

Pro Gly Arg Ser Leu Arg Leu Ser Cys Ala Ala Ser Gly Phe Thr Phe
     35                 40               45

Asp Asp Tyr Ala Met His Trp Val Arg Gln Ala Pro Gly Lys Gly Leu
 50                 55               60

Glu Trp Val Ser Gly Ile Ser Trp Asn Ser Gly Ser Ile Gly Tyr Ala
65               70                 75               80

Asp Ser Val Lys Gly Arg Phe Thr Ile Ser Arg Asp Asn Ala Lys Asn
             85                 90               95

Ser Leu Tyr Leu Gln Met Asn Ser Leu Arg Ala Glu Asp Thr Ala Leu
            100               105              110

Tyr Tyr Cys Ala Lys Asp Ile Asp Tyr Tyr Tyr Tyr Tyr Gly Met
         115               120              125

Asp Val Trp Gly Gln Gly Thr Thr Val Thr Val Ser Ser
    130               135               140

<210> SEQ ID NO 57
<211> LENGTH: 127
<212> TYPE: PRT
<213> ORGANISM: Homo sapiens

<400> SEQUENCE: 57

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys
        115                 120                 125

<210> SEQ ID NO 58
<211> LENGTH: 42
<212> TYPE: DNA
<213> ORGANISM: Artificial Sequence
<220> FEATURE:
<223> OTHER INFORMATION: Primer

<400> SEQUENCE: 58
tggggagttt ttctcagagg aattcgatgg ttcacagttg ta                42

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
tgtaacagta ttgggtagat ggg                                    23

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
aatcatggac atacttaata tta                                    23

<210> SEQ ID NO 61
<211> LENGTH: 41
<212> TYPE: DNA
<213> ORGANISM: Artificial Sequence
<220> FEATURE:
<223> OTHER INFORMATION: Primer

<400> SEQUENCE: 61
tatagcccgg ggccgccacc atgacaacac ccagaaattc a                41

<210> SEQ ID NO 62
<211> LENGTH: 38
<212> TYPE: DNA
<213> ORGANISM: Artificial Sequence

```
<220> FEATURE:
<223> OTHER INFORMATION: Primer

<400> SEQUENCE: 62
gcgtctcatg tacattaagg agagctgtca ttttctat                              38

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
tcggacatct catgactttc ttt                                              23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
gtagtctgag cagtactcgt tgc                                              23

<210> SEQ ID NO 65
<211> LENGTH: 42
<212> TYPE: DNA
<213> ORGANISM: Artificial Sequence
<220> FEATURE:
<223> OTHER INFORMATION: Primer

<400> SEQUENCE: 65
tggggagttt ttctcagagg aattcgatgg ttcacagttg ta                         42

<210> SEQ ID NO 66
<211> LENGTH: 42
<212> TYPE: DNA
<213> ORGANISM: Artificial Sequence
<220> FEATURE:
<223> OTHER INFORMATION: Primer

<400> SEQUENCE: 66
tacaactgtg aaccatcgaa ttcctctgag aaaaactccc ca                         42

<210> SEQ ID NO 67
<211> LENGTH: 23
<212> TYPE: DNA
<213> ORGANISM: Artificial Sequence
<220> FEATURE:
<223> OTHER INFORMATION: Primer

<400> SEQUENCE: 67
tgtaacagta ttgggtagat ggg                                              23

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
aatcatggac atacttaata tta                                              23
```

```
<210> SEQ ID NO 69
<211> LENGTH: 15
<212> TYPE: PRT
<213> ORGANISM: Artificial Sequence
<220> FEATURE:
<223> OTHER INFORMATION: Synthetic peptide

<400> SEQUENCE: 69

Lys Met Glu Cys Leu Asn Phe Ile Arg Ala His Cys Pro Tyr Ile
 1               5                  10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic peptide

<400> SEQUENCE: 70

Leu Lys Met Glu Cys Leu Asn Phe Ile Arg Cys His Thr Pro Tyr
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic peptide

<400> SEQUENCE: 71

Lys Met Glu Ser Cys Asn Phe Ile Arg Ala Cys Thr Pro Tyr Ile
 1               5                  10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic peptide

<400> SEQUENCE: 72

Met Glu Ser Leu Cys Phe Ile Arg Ala His Cys Pro Tyr Ile Asn
 1               5                  10                  15

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Cys Phe Ile Arg Ala His Thr Pro Cys
 1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

Cys Ile Arg Ala His Thr Pro Tyr Cys
 1               5

<210> SEQ ID NO 75
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 75

Cys Arg Ala His Thr Pro Tyr Ile Cys
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Cys Ala His Thr Pro Tyr Ile Asn Cys
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic peptide

<400> SEQUENCE: 77

Ile Pro Ala Gly Ile Tyr Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic peptide

<400> SEQUENCE: 78

Pro Ala Gly Ile Tyr Ala Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Ala Gly Ile Tyr Ala Pro Ile
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Gly Ile Tyr Ala Pro Ile Cys
1               5

<210> SEQ ID NO 81
<211> LENGTH: 7
<212> TYPE: PRT
<213> ORGANISM: Artificial Sequence
```

<220> FEATURE:
<223> OTHER INFORMATION: Synthetic peptide

<400> SEQUENCE: 81

Ile Tyr Ala Pro Ile Cys Val
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Gly Ile Tyr Ala Pro Ile Ala
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide

<400> SEQUENCE: 83

Ile Tyr Ala Pro Ile Ala Val
1               5

<210> SEQ ID NO 84
<211> LENGTH: 15
<212> TYPE: PRT
<213> ORGANISM: Artificial Sequence
<220> FEATURE:
<223> OTHER INFORMATION: Synthetic peptide

<400> SEQUENCE: 84

Pro Cys Ile Asn Ile Tyr Asn Ala Glu Pro Ala Asn Pro Cys Glu
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide

<400> SEQUENCE: 85

Tyr Cys Asn Ile Tyr Asn Ala Glu Pro Ala Asn Pro Ser Cys Lys
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic peptide

<400> SEQUENCE: 86

Ile Cys Ile Tyr Asn Ala Glu Pro Ala Asn Pro Ser Glu Cys Asn
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic peptide -continued

<400> SEQUENCE: 87

Asn Cys Tyr Asn Ala Glu Pro Ala Asn Pro Ser Glu Lys Cys Ser
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic peptide

<400> SEQUENCE: 88

Ile Cys Asn Ala Glu Pro Ala Asn Pro Ser Glu Lys Asn Cys Pro
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic peptide

<400> SEQUENCE: 89

Tyr Cys Ala Glu Pro Ala Asn Pro Ser Glu Lys Asn Ser Cys Ser
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic peptide

<400> SEQUENCE: 90

Asn Cys Glu Pro Ala Asn Pro Ser Glu Lys Asn Ser Pro Cys Thr
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic peptide

<400> SEQUENCE: 91

Ala Cys Pro Ala Asn Pro Ser Glu Lys Asn Ser Pro Ser Cys Gln
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic peptide

<400> SEQUENCE: 92

Glu Cys Ala Asn Pro Ser Glu Lys Asn Ser Pro Ser Thr Cys Tyr
1               5                   10                  15

<210> SEQ ID NO 93
<211> LENGTH: 6
<212> TYPE: PRT
<213> ORGANISM: Artificial Sequence
<220> FEATURE:
<223> OTHER INFORMATION: Synthetic peptide

<400> SEQUENCE: 93

```
Ala Gly Ile Tyr Ala Pro
 1               5

<210> SEQ ID NO 94
<211> LENGTH: 14
<212> TYPE: PRT
<213> ORGANISM: Artificial Sequence
<220> FEATURE:
<223> OTHER INFORMATION: Synthetic peptide

<400> SEQUENCE: 94

Met Glu Ser Leu Asn Phe Ile Arg Ala His Thr Pro Tyr Ile
 1               5                  10

<210> SEQ ID NO 95
<211> LENGTH: 8
<212> TYPE: PRT
<213> ORGANISM: Artificial Sequence
<220> FEATURE:
<223> OTHER INFORMATION: Synthetic peptide

<400> SEQUENCE: 95

Glu Pro Ala Asn Pro Ser Glu Lys
 1               5
```

HUMAN MONOCLONAL ANTIBODIES AGAINST CD20

RELATED APPLICATIONS

This application claims priority to U.S. Provisional Application No.: 60/419163, filed on Oct. 17, 2002, and U.S. Provisional Application No.: 60/460028, filed on Apr. 2, 2003, both entitled HUMAN MONOCLONAL ANTIBODIES AGAINST CD20, and both of which are incorporated herein in their entirety by this reference.

BACKGROUND OF THE INVENTION

The CD20 molecule (also called human B-lymphocyte-restricted differentiation antigen or Bp35) is a hydrophobic transmembrane protein with a molecular weight of approximately 35 kD located on pre-B and mature B lymphocytes (Valentine et al. (1989) *J. Biol. Chem.* 264(19):11282-11287; and Einfield et al. (1988) *EMBO J.* 7(3):711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson et al. (1984) *Blood* 63(6):1424-1433), but is not found on hematopoietic stem cells, pro-B cells, normal plasma cells, or other normal tissues (Tedder et al. (1985) *J. Immunol.* 135(2):973-979).

The 85 amino acid carboxyl-terminal region of the CD20 protein is located within the cytoplasm. The length of this region contrasts with that of other B cell-specific surface structures such as IgM, IgD, and IgG heavy chains or histocompatibility antigens class II $\alpha$ or $\beta$ chains, which have relatively short intracytoplasmic regions of 3, 3, 28, 15, and 16 amino acids, respectively (Komaromy et al. (1983) NAR 11:6775-6785). Of the last 61 carboxyl-terminal amino acids, 21 are acidic residues, whereas only 2 are basic, indicating that this region has a strong net negative charge. The GenBank Accession No. is NP_690605.

It is thought that CD20 might be involved in regulating an early step(s) in the activation and differentiation process of B cells (Tedder et al. (1986) *Eur.J. Immunol.* 16:881-887) and could function as a calcium ion channel (Tedder et al. (1990) *J. Cell. Biochem.* 14D:195).

Despite uncertainty about the actual function of CD20 in promoting proliferation and/or differentiation of B cells, it provides an important target for antibody mediated therapy to control or kill B cells involved in cancers and autoimmune disorders. In particular, the expression of CD20 on tumor cells, e.g., NHL, makes it an important target for antibody mediated therapy to specifically target therapeutic agents against CD20-positive neoplastic cells. However, while the results obtained to date clearly establish CD20 as a useful target for immunotherapy, they also show that currently available murine and chimeric antibodies do not constitute ideal therapeutic agents.

Accordingly, the need exists for improved therapeutic antibodies against CD20 which are effective in preventing and/or treating a range of diseases involving cells expressing CD20.

SUMMARY OF THE INVENTION

The present invention provides improved antibody therapeutics for treating and/or preventing diseases associated with cells expressing CD20, including tumor-related diseases, and immune diseases, including autoimmune diseases. The antibodies encompassed by the invention are improved in that they are fully human and, thus, are potentially less immunogenic in patients.

As exemplified herein, the human antibodies of the invention mediate killing of B cells expressing CD20 by a variety of mechanisms. In one embodiment, human antibodies of the invention induce complement dependent cytotoxicity (CDC), e.g., at least about 20% CDC mediated lysis, preferably about 30% CDC mediated lysis, and more preferably 40-50% mediated lysis in cells, such as chronic B-lymphocytic leukaemia (B-CLL) cells. In another embodiment, human antibodies of the invention induce apoptosis of cells expressing CD20. In another embodiment, human antibodies of the invention induce homotypic adhesion of cells expressing CD20. Furthermore, the human antibodies of the invention may induce antibody dependent cellular cytotoxicity (ADCC) of cells expressing CD20 in the presence of human effector cells (e.g., monocytes, mononuclear cells, NK cells and PMNs). Furthermore, human antibodies of the invention may induce phagocytosis of cells expressing CD20 in the presence of macrophages. The human monoclonal antibodies of the invention may work by one or more of these mechanisms. Examples of cells which can be killed by human antibodies of the present invention include, but are not limited to, B cells expressing CD20, such as tumorigenic B cells and B cells involved in immune diseases. In a particular embodiment, the human antibodies are used to mediate killing of B lymphocytes in the treatment of lymphoma, e.g., B cell non-Hodgkin's lymphoma.

Human antibodies of the invention include IgG1 (e.g., IgG1,κ), IgG3 (e.g., IgG3,κ) and IgG4 (e.g., IgG4,κ) antibodies. However, other antibody isotypes are also encompassed by the invention, including IgG2, IgM, IgA1, IgA2, secretory IgA, IgD, and IgE. The antibodies can be whole antibodies or antigen-binding fragments thereof including, for example, Fab, F(ab')$_2$, Fv, single chain Fv fragments or bispecific antibodies. Furthermore, the antigen-binding fragments include binding-domain immunoglobulin fusion proteins comprising (i) a binding domain polypeptide (such as a heavy chain variable region or a light chain variable region) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. Such binding-domain immunoglobulin fusion proteins are further disclosed in US 2003/0118592 and US 2003/0133939.

Particular human antibodies of the present invention include those referred to as 11B8, 2F2, and 7D8, encoded by human heavy chain and human kappa light chain nucleic acids comprising nucleotide sequences in their variable regions as set forth in SEQ ID NOs:1, 5, or 9 and SEQ ID NOs:3, 7, or 11, respectively, and conservative sequence modifications thereof. In another embodiment, the human antibodies are characterized by having human heavy chain and human kappa light chain variable regions comprising the amino acid sequences as set forth in SEQ ID NOs:2, 6, or 10 and SEQ ID NOs:4, 8, or 12, respectively, and conservative sequence modifications thereof.

In yet another embodiment, the human antibodies are characterized by having human heavy chain and human kappa light chain variable regions which are at least 90% homologous, preferably at least 95% homologous, and more preferably at least 98%, or at least 99% homologous to the amino acid sequences as set forth in SEQ ID NO:2 and SEQ ID NO:4, respectively; SEQ ID NO:6 and SEQ ID NO:8, respectively; or SEQ ID NO:10 and SEQ ID NO:12, respectively.

Other particular human antibodies of the invention include those which comprise a CDR domain having a human heavy and light chain CDR1 region, a human heavy and light chain CDR2 region, and a human heavy and light chain CDR3 region, wherein (a) the CDR1, CDR2, and CDR3 human heavy chain regions comprise an amino acid sequence selected from the group consisting of the amino acid sequences CDR1, CDR2, and CDR3 shown in FIGS. 53, 55, or 57 (SEQ ID NOs:13-15, 19-21, and 25-27), and conservative sequence modifications thereof, and (b) the CDR1, CDR2, and CDR3 human light chain regions comprise an amino acid sequence selected from the group consisting of the amino acid sequences CDR1, CDR2, and CDR3 shown in FIGS. 53, 55, or 57 (SEQ ID NOs: 16-18, 22-24, and 28-30), and conservative sequence modifications thereof.

Also included within the present invention are antibodies which dissociate from CD20 with a dissociation equilibrium constant ($K_D$) of approximately 1-10 nM or less. Such antibodies also include those which do not cross-react with related cell-surface antigens and thus do not inhibit their function.

In another embodiment, human anti-CD20 antibodies of the present invention can be characterized by one or more of the following properties:

a) specificity for human CD20;

b) a binding affinity to CD20 ($K_D$) of about 10 nM or less, preferably, about 5 nM or less and, more preferably, about 1-3 nM or less as determined by the binding experiment disclosed in Example 5 (FIG. 9) herein;

c) a dissociation rate constant ($k_d$) from CD20 of about $10^{-4}$ sec$^{-1}$ or less, preferably, about $10^{-5}$ sec$^{-1}$ or less and, more preferably, about $10^{-6}$ sec$^{-1}$ or less, as determined by the dissociation rate experiment disclosed in Example 5 (FIG. 9) herein;

d) the ability to mediate a high level of CDC on either CD55/59 negative or CD55/59 positive cells;

e) the ability to translocate into lipid rafts upon binding to CD20;

f) the ability to inhibit the growth of cells which express CD20;

g) the ability to induce apoptosis of cells which express CD20;

h) the ability to induce homotypic adhesion of cells which express CD20;

i) the ability to induce ADCC of cells which express CD20 in the presence of effector cells;

j) the ability to prolong survival of a subject having tumor cells which express CD20;

k) the ability to deplete cells which express CD20; and/or l) the ability to deplete cells which express low levels of CD20 (CD20$^{low}$ cells).

The human anti-CD20 antibodies of the present invention can be derivatized, linked to or co-expressed to other binding specificities. In a particular embodiment, the invention provides a bispecific or multispecific molecule comprising at least one first binding specificity for CD20 (e.g., a human anti-CD20 antibody or mimetic thereof), and a second binding specificity for a human effector cell, such as a binding specificity for an Fc receptor (e.g., a human Fcγ receptor, such as FcγRI, or a human Fcα receptor) or a T cell receptor, e.g., CD3.

Accordingly, the present invention includes bispecific and multispecific molecules that bind to both human CD20 and to an Fc receptor or a T cell receptor, e.g., CD3. Examples of Fc receptors are, e.g., a human IgG receptor, e.g., an Fc-gamma receptor (FcγR), such as FcγRI (CD64), FcγRII (CD32), and FcγRIII (CD16). Other Fc receptors, such as human IgA receptors (e.g., FcαRI), also can be targeted. The Fc receptor is preferably located on the surface of an effector cell, e.g., a monocyte, macrophage or an activated mononuclear cell. In a preferred embodiment, the bispecific and multispecific molecules bind to an Fc receptor at a site which is distinct from the immunoglobulin Fc (e.g., IgG or IgA) binding site of the receptor. Therefore, the binding of the bispecific and multispecific molecules is not blocked by physiological levels of immunoglobulins.

In yet another aspect, human anti-CD20 antibodies of the invention are derivatized, linked to or co-expressed with another functional molecule, e.g., another peptide or protein (e.g., a Fab' fragment). For example, an antibody of the invention can be functionally linked (e.g., by chemical coupling, genetic fusion, noncovalent association or otherwise) to one or more other molecular entities, such as another antibody (e.g., to produce a bispecific or a multispecific antibody), a cytotoxin, cellular ligand or antigen (e.g., to produce an immunoconjugate, such as an immunotoxin). An antibody of the present invention can be linked to other therapeutic moieties, e.g., a radioisotope, a small molecule anti-cancer drug, an anti-inflammatory agent, or an immunosuppressive agent. Accordingly, the present invention encompasses a large variety of antibody conjugates, bispecific and multispecific molecules, and fusion proteins, all of which bind to CD20 expressing cells and which can be used to target other molecules to such cells.

In still another aspect, the invention provides compositions, e.g., pharmaceutical and diagnostic compositions/kits, comprising a pharmaceutically acceptable carrier formulated along with one or a combination of human monoclonal antibodies of the invention. In a particular embodiment, the composition includes a combination of antibodies which bind to distinct epitopes or which possess distinct functional characteristics, such as inducing CDC and inducing apoptosis.

Human antibodies, immunoconjugates, bispecific and multispecific molecules and compositions of the present invention can be used in a variety of methods for inhibiting growth of cells expressing CD20 and/or killing cells expressing CD20 by contacting the cells with an effective amount of the antibody, immunconjugate, bispecific/multispecific molecule or composition, such that the growth of the cell is inhibited and/or the cell is killed. In one embodiment, the method includes killing of the cell expressing CD20 in the presence of effector cells, for example, by CDC, apoptosis, ADCC, phagocytosis, or by a combination of two or more of these mechanisms. The cells are preferably killed or inhibited without killing or inhibiting the activity of cells which do not express CD20 but which may, for example, express a structurally related cell-surface antigen (i.e., without cross-reactivity to related but functionally distinct cell surface antigens). Cells expressing CD20 which can be inhibited or killed using the human antibodies of the invention include, for example, tumorigenic B cells.

Accordingly, human antibodies of the present invention can be used to treat and/or prevent a variety of diseases involving cells expressing CD20 by administering the antibodies to patients suffering from such diseases. Exemplary diseases that can be treated (e.g., ameliorated) or prevented include, but are not limited to, tumorigenic diseases and immune diseases, e.g., autoimmune diseases. Examples of tumorigenic diseases which can be treated and/or prevented include B cell lymphoma, e.g., NHL, including precursor B cell lymphoblastic leukemia/lymphoma and mature B cell neoplasms, such as B cell chronic lymhocytic leukemia (CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenström's macroglobulinemia, and anaplastic large-cell lymphoma (ALCL). Examples of immune disorders in which CD20 expressing B cells are involved which can be treated and/or prevented include psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HIV, and herpes virus associated diseases. Further examples are severe acute respiratory distress syndrome and choreoretinitis. Yet further examples are diseases and disorders caused by infection of B-cells with virus, such as Epstein-Barr virus (EBV).

In a particular embodiment of the invention, the subject being administered the antibody is additionally treated with a chemotherapeutic agent, radiation, or an agent that modulates, e.g., enhances or inhibits, the expression or activity of an Fc receptor, e.g., an Fcα receptor or an Fcγ receptor, such as a cytokine. Typical, cytokines for administration during treatment include granulocyte colony-stimulating factor (G-CSF), granulocyte-macrophage colony-stimulating factor (GM-CSF), interferon-γ (IFN-γ), and tumor necrosis factor (TNF). Typical therapeutic agents include, among others, anti-neoplastic agents such as doxorubicin, cisplatin, bleomycin, carmustine, chlorambucil, and cyclophosphamide.

In yet another aspect, the present invention provides a method for detecting in vitro or in vivo the presence of CD20 in a sample or individual, e.g., for diagnosing a CD20-related disease, preferably at an early stage. This can also be useful for monitoring the disease and effect of treatment and for determining and adjusting the dose of the antibody to be administered. The in vivo method can be performed using imaging technique such as PET (positron emission tomography) or SPECT (single photon emission computed tomography). In one embodiment, this is achieved by contacting a sample to be tested, optionally along with a control sample, with a human monoclonal antibody of the invention under conditions that allow for formation of a complex between the antibody and CD20. Complex formation is then detected (e.g., using an FACS analysis or Western blotting). When using a control sample along with the test sample, complex is detected in both samples and any statistically significant difference in the formation of complexes between the samples is indicative of the presence of CD20 in the test sample.

In yet another aspect, the invention provides a transgenic non-human animal, such as a transgenic mouse, which express human monoclonal antibodies that bind to CD20. In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of CD20 antigen and/or cells expressing CD20. Preferably, the transgenic non-human animal, e.g., the transgenic mouse, is capable of producing multiple isotypes of human monoclonal antibodies to CD20 (e.g., IgG, IgA and/or IgM) by undergoing V-D-J recombination and isotype switching. Isotype switching may occur by, e.g., classical or non-classical isotype switching.

Accordingly, in yet another aspect, the invention provides isolated B cells from a transgenic non-human animal as described above, e.g., a transgenic mouse, which expresses human anti-CD20 antibodies. The isolated B cells can then be immortalized by fusion to an immortalized cell to provide a source (e.g., a hybridoma) of human anti-CD20 antibodies. Such hybridomas (i.e., which produce human anti-CD20 antibodies) are also included within the scope of the invention.

As exemplified herein, human antibodies of the invention can be obtained directly from hybridomas which express the antibody, or can be cloned and recombinantly expressed in a host cell (e.g., a CHO cell, a NS/0 cell or a lymphocytic cell). Further examples of host cells are microorganisms, such as *E. coli*, and fungi, such as yeast. Alternatively, they can be produced recombinantly in a transgenic non-human animal or plant. Accordingly, in another aspect, the present invention provides methods for producing human monoclonal antibodies which bind to human CD20. In one embodiment, the method includes immunizing a transgenic non-human animal, e.g., a transgenic mouse, as previously described (e.g., having a genome comprising a human heavy chain transgene and a human light chain transgene encoding all or a portion of an anti-CD20 antibody), with a purified or enriched preparation of human CD20 antigen and/or cells expressing human CD20. B cells (e.g., splenic B cells) of the animal are then obtained and fused with myeloma cells to form immortal, hybridoma cells that secrete human monoclonal antibodies against CD20.

In yet another aspect, the invention provides nucleic acid molecules encoding human anti-CD20 antibodies (e.g., variable regions thereof), as well as recombinant expression vectors which include the nucleic acids of the invention, and host cells transfected with such vectors. Methods of producing the antibodies by culturing these host cells are also encompassed by the invention. Particular nucleic acids provided by the invention comprise the nucleotide sequences shown in SEQ ID NOs:1, 5, or 9 and SEQ ID NOs:3, 7, or 11, encoding the heavy and light chains, respectively, of human anti-CD20 antibodies 2F2, 7D8, and 11B8.

Other features and advantages of the instant invention will be apparent from the following detailed description and claims.

BRIEF DESCRIPTION OF THE DRAWINGS

FIG. 53 shows the amino acid sequence (SEQ ID NO:2) of the heavy chain V region and the amino acid sequence (SEQ ID NO:4) of the light (kappa) chain V region of human monoclonal antibody 2F2 with CDR regions SEQ ID NOs:13-18) designated.

FIG. 54 shows the nucleotide sequence (SEQ ID NO:1) of the heavy chain V region and the nucleotide sequence (SEQ ID NO:3) of the light (kappa) chain V region of human monoclonal antibody 2F2.

FIG. 55 shows the amino acid sequence (SEQ ID NO:6) of the heavy chain V region and the amino acid sequence (SEQ ID NO:8) of the light (kappa) chain V region of human monoclonal antibody 7D8 with CDR regions (SEQ ID NOs:19-24) designated.

FIG. 56 shows the nucleotide sequence (SEQ ID NO:5) of the heavy chain V region and the nucleotide sequence (SEQ ID NO:7) of the light (kappa) chain V region of human monoclonal antibody 7D8.

FIG. 57 shows the amino acid sequence (SEQ ID NO:10) of the heavy chain V region and the amino acid sequence (SEQ ID NO:12) of the light (kappa) chain V region of human monoclonal antibody 11B8 with CDR regions (SEQ ID NOs: 25-30) designated.

FIG. 58 shows the nucleotide sequence (SEQ ID NO:9) of the heavy chain V region and the nucleotide sequence (SEQ ID NO:11) of the light (kappa) chain V region of human monoclonal antibody 11B8.

DETAILED DESCRIPTION OF THE INVENTION

Figure 1:
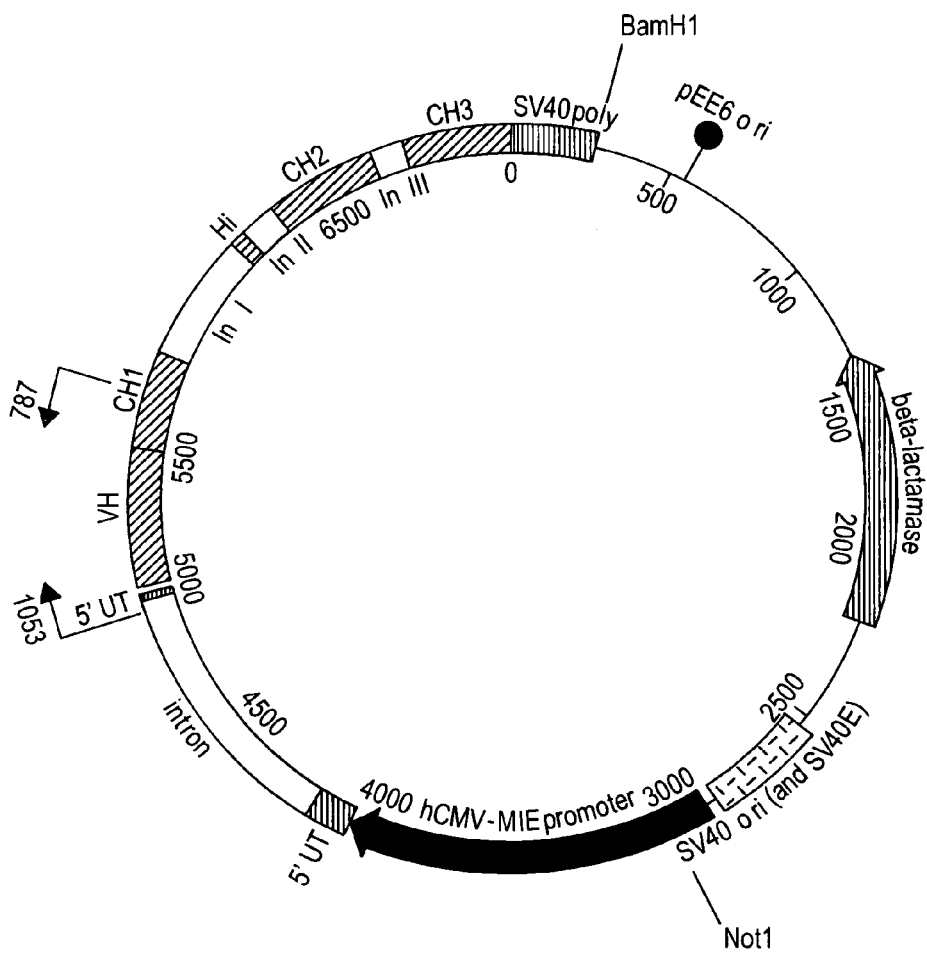
FIG. 1 shows the pCONγ1f/variable-heavy vector used for recombinant production of the human monoclonal antibodies 2F2 and 11B8.

The present invention provides improved antibody-based therapies for treating and diagnosing a variety of disorders involving cells expressing CD20. Therapies of the invention employ isolated human monoclonal antibodies which specifically bind to an epitope present on CD20. Isolated human monoclonal antibodies encompassed by the present invention include IgA, IgG1-4, IgE, IgM, and IgD antibodies.

In one embodiment the antibody is an IgG1 antibody, more particularly an IgG1,κ or IgG1,λ isotype. In another embodiment the antibody is an IgG3 antibody, more particularly an IgG3,κ or IgG3,λ isotype. In yet another embodiment the antibody is an IgG4 antibody, more particularly an IgG4,κ or IgG4,λ isotype. In still another embodiment the antibody is an IgA1 or IgA2 antibody.

In still another embodiment the antibody is an IgM antibody.

In one embodiment, the human antibodies are produced in a non-human transgenic animal, e.g., a transgenic mouse, capable of producing multiple isotypes of human monoclonal antibodies to CD20 by undergoing V-D-J recombination and isotype switching. Accordingly, aspects of the invention include not only antibodies, antibody fragments, and pharmaceutical compositions thereof, but also non-human transgenic animals, B cells, host cell transfectomas, and hybridomas which produce monoclonal antibodies. Such transgenic animal can also be a transgenic rabbit for producing polyclonal antibodies such as disclosed in US 2003/0017534. Accordingly, the invention also encompasses human polyclonal antibodies which specifically bind to CD20. In one embodiment the invention relates to polyclonal antibodies which bind to an epitope on CD20 (i) which does not comprise or require the amino acid residue proline at position 172; (ii) which does not comprise or require the amino acid residues alanine at position 170 or proline at position 172; (iii) which comprises or requires the amino acid residues asparagine at position 163 and asparagine at position 166; (iv) which does not comprise or require the amino acid residue proline at position 172, but which comprises or requires the amino acid residues asparagine at position 163 and asparagine at position 166; or (v) which does not comprise or require the amino acid residues alanine at position 170 or proline at position 172, but which comprises or requires the amino acid residues asparagine at position 163 and asparagine at position 166.

In another embodiment the invention relates to human polyclonal antibodies which have one or more of the following characteristics: (i) bind to mutant P172S CD20 (proline at position 172 mutated to serine) with at least the same affinity as to human CD20; (ii) bind to mutant A×P (alanine at position 170 mutated to serine, and proline at position 172 mutated to serine) with at least the same affinity as to human CD20; (iii) show a reduced binding of 50% or more to mutant N166D (asparagine at position 166 mutated to aspartic acid) to human CD20 at an antibody concentration of 10 μg/ml; and/or (iv) show a reduced binding of 50% or more to mutant N163D (asparagine at position 163 mutated to aspartic acid) compared to human CD20 at an antibody concentration of 10 µg/ml.

In yet another embodiment the invention the invention relates to human polyclonal antibodies which bind to an epitope in the small first extracellular loop of human CD20. In still another embodiment the invention also encompasses human polyclonal antibodies which bind to a discontinuous epitope on CD20. In a further embodiment the invention relates to human polyclonal antibodies which bind a discontinuous epitope on CD20, which has part of the first small extracellular loop and part of the second extracellular loop. In still a further embodiment the invention relates to human polyclonal antibodies which bind to a discontinuous epitope on CD20, which has residues AGIYAP (SEQ ID NO:93) of the small first extracellular loop and residues MESLN-FIRAHTPYI (SEQ ID NO:94) of the second extracellular loop.

Methods of using the antibodies of the invention to detect a cell expressing CD20 are encompassed by the invention. Methods of using the antibodies of the invention to block or inhibit CD20 induced activities, e.g., proliferative and/or differentiation activities, are also provided and are useful in the treatment of disorders associated with CD20, such as tumorigenic diseases (e.g., B cell lymphoma) and autoimmune diseases (e.g., RA, Chrohn's disease and Wegener's granulomatosis).

In order that the present invention may be more readily understood, certain terms are first defined. Additional definitions are set forth throughout the detailed description.

The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 (e.g., a tumor cell) by inactivating CD20. The killing of the cells expressing CD20 may occur by one or more of the following mechanisms:

complement dependent cytotoxity (CDC) of cells expressing CD20;
apoptosis of cells expressing CD20;
effector cell phagocytosis of cells expressing CD20; or
effector cell antibody dependent cellular cytotoxicity (ADCC) of cells expressing CD20.

Synonyms of CD20, as recognized in the art, include B-lymphocyte antigen CD20, B-lymphocyte surface antigen B1, Leu-16, Bp35, BM5, and LF5.

As used herein, the term "inhibits growth" (e.g., referring to cells) is intended to include any measurable decrease in the cell growth when contacted with an anti-CD20 antibody as compared to the growth of the same cells not in contact with an anti-CD20 antibody, e.g., the inhibition of growth of a cell culture by at least about 10%, 20%, 30%, 40%, 50%, 60%, 70%, 80%, 90%, 99%, or 100%. Such a decrease in cell growth can occur by a variety of mechanisms, e.g., effector cell phagocytosis, ADCC, CDC, and/or apoptosis.

The term "raft" refers to the sphingolipid- and cholesterol-rich membrane microdomains located in the outer leaflet area of the plasma membrane of a cell. The ability of certain proteins to associate within such domains can effect the protein's function. For example, the translocation of CD20 molecules into lipid rafts, after being bound by human antibodies of the present invention, creates a high density of CD20 antigen-antibody complexes in the plasma membranes. Such a high density of CD20 antigen-antibody complexes can enable efficient activation of the complement system during CDC.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., CD20). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR), and (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., *Bird* et al. (1988) *Science* 242:423-426; and *Huston* et al. (1988) *Proc. Natl. Acad. Sci. USA* 85:5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "discontinuous epitope," as used herein, means a conformational epitope on a protein antigen which is formed from at least two separate regions in the primary sequence of the protein.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as CD20, and to other targets, such as Fc receptors on effector cells.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

The term "human antibody derivatives" refers to any modified form of the antibody, e.g., a conjugate of the antibody and another agent or antibody.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library, and wherein the selected human antibody is at least 90%, more preferably at least 95%, even more preferably at least 96%, 97%, 98%, or 99% identical in amino acid sequence to the amino acid sequence encoded by the germline immunoglobulin gene. Typically, a human antibody derived from a particular human germline sequence will display no more than 10 amino acid differences, more preferably, no more than 5, or even more preferably, no more than 4, 3, 2, or 1 amino acid difference from the amino acid sequence encoded by the germline immunoglobulin gene.

As used herein, the term "heteroantibodies" refers to two or more antibodies, derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic or transchromosomal non-human animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "transfectoma", as used herein, includes recombinant eukaryotic host cell expressing the antibody, such as CHO cells, NS/0 cells, HEK293 cells, plant cells, or fungi, including yeast cells.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

An "isolated antibody," as used herein, is intended to refer to an antibody which is substantially free of other antibodies having different antigenic specificities (e.g., an isolated antibody that specifically binds to CD20 is substantially free of antibodies that specifically bind antigens other than CD20).

An isolated antibody that specifically binds to an epitope, isoform or variant of human CD20 may, however, have cross-reactivity to other related antigens, e.g., from other species (e.g., CD20 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity corresponding to a $K_D$ of about $1 \times 10^{-7}$ M or less, and binds to the predetermined antigen with an affinity corresponding to a $K_D$ that is at least two orders of magnitude lower than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "$k_d$" (sec$^{-1}$), as used herein, is intended to refer to the dissociation rate constant of a particular antibody-antigen interaction. Said value is also referred to as the $k_{off}$ value.

The term "$k_a$" (M$^{-1} \times$sec$^{-1}$), as used herein, is intended to refer to the association rate constant of a particular antibody-antigen interaction.

The term "$K_D$" (M), as used herein, is intended to refer to the dissociation equilibrium constant of a particular antibody-antigen interaction.

The term "$K_A$" (M$^{-1}$), as used herein, is intended to refer to the association equilibrium constant of a particular antibody-antigen interaction and is obtained by dividing the $k_a$ by the $k_d$.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the non-switched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a $\mu$ switch region, will be 5' (i.e., upstream) of the construct region to be deleted during the switch recombination. The "switch acceptor" region will be between the construct region to be deleted and the replacement constant region (e.g., $\gamma$, $\epsilon$, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin (antibody) protein. A glycosylation pattern of a heterologous antibody can be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding whole antibodies or antibody portions (e.g., $V_H$, $V_L$, CDR3) that bind to CD20, is intended to refer to a nucleic acid molecule in which the nucleotide sequences encoding the intact antibody or antibody portion are free of other nucleotide sequences encoding whole antibodies or antibody portions that bind antigens other than CD20, which other sequences may naturally flank the nucleic acid in human genomic DNA. In one embodiment, the human anti-CD20 antibody includes the nucleotide or amino acid sequence of 2F2, 7D8, or 11B8, as well as heavy chain ($V_H$) and light chain ($V_L$) variable regions having the sequences shown in SEQ ID NOs: 1, 5, or 9, and SEQ ID NOs: 3, 7, or 11, respectively.

As disclosed and claimed herein, the sequences set forth in SEQ ID NOs: 1-30 include "conservative sequence modifications," i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs:1-30 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD20 antibody is preferably replaced with another amino acid residue from the same side chain family.

The present invention also encompasses "derivatives" of the amino acid sequences as set forth in SEQ ID NOs: 1-30 and conservative sequence modifications thereof, wherein one or more of the amino acid residues have been derivatised, e.g., by acylation or glycosylation, without significantly affecting or altering the binding characteristics of the antibody containing the amino acid sequences.

Furthermore, the present invention comprises antibodies in which alterations have been made in the Fc region in order to change the functional or pharmacokinetic properties of the antibodies. Such alterations may result in a decrease or increase of C1q binding and CDC or of FcγR binding and ADCC. Substitutions can, for example, be made in one or more of the amino acid residues at positions 234, 235, 236, 237, 297, 318, 320 and 322 of the heavy chain constant region, thereby causing an alteration in an effector function while retaining the ability to bind to the antigen as compared with the unmodified antibody, cf. U.S. Pat. Nos. 5,624,821 and 5,648,260.

The in vivo half-life of the antibodies can also be improved by modifying the salvage receptor epitope of the Ig constant domain or an Ig-like constant domain such that the molecule does not comprise an intact CH2 domain or an intact Ig Fc region, cf. U.S. Pat. Nos. 6,121,022 and 6,194,551. The in vivo half-life can furthermore be increased by making mutations in the Fc region, e.g., by substituting threonine for leucine at position 252, by substituting threonine for serine at position 254, or by substituting threonine for phenylalanine at position 256, cf. U.S. Pat. No. 6,277,375.

Furthermore, the glycosylation pattern of the antibodies can be modified in order to change the effector function of the antibodies. For example, the antibodies can be expressed in a transfectoma which does not add the fucose unit normally attached to Asn at position 297 of the Fc region in order to enhance the affinity of the Fc region for FcγRIII which, in turn, will result in an increased ADCC of the antibodies in the presence of NK cells, cf. Shield et al. (2002) *JBC*, 277:26733. Furthermore, modification of galactosylation can be made in order to modify CDC.

Alternatively, in another embodiment, mutations can be introduced randomly along all or part of a anti-CD20 antibody coding sequence, such as by saturation mutagenesis, and the resulting modified anti-CD20 antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 1-30) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID Nos:1-30 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For nucleotide and amino acid sequences, the term "homology" indicates the degree of identity between two nucleic acid or amino acid sequences when optimally aligned and compared with appropriate insertions or deletions. Alternatively, substantial homology exists when the DNA segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res*. 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription of regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD20 antibodies when immunized with CD20 antigen and/or cells expressing CD20. The human heavy chain transgene can be integrated into the chromosomal DNA of the mouse, as is the case for transgenic, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to CD20 (e.g., IgG, IgA and/or IgE) by undergoing V-D-J recombination and isotype switching.

Various aspects of the invention are described in further detail in the following subsections.

I. Production of Human Antibodies to CD20

Human monoclonal antibodies of the invention can be produced by a variety of techniques, including conventional monoclonal antibody methodology, e.g., the standard somatic cell hybridization technique of Kohler and Milstein, *Nature* 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

The preferred animal system for preparing hybridomas that secrete human monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against CD20 can be generated using transgenic or transchromosomal mice carrying parts of the human immune system rather than the mouse system. These transgenic and transchromosomic mice include mice referred to herein as HuMAb mice and KM mice, respectively, and are collectively referred to herein as "transgenic mice."

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368 (6474): 856-859). Accordingly, the mice exhibit reduced expression of mouse IgM or κ and in response to immunization, the introduced human heavy and light chain transgenes, undergo class switching and somatic mutation to generate high affinity human IgG κ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y Acad. Sci* 764: 536-546). The preparation of HuMAb mice is described in detail in Taylor, L. et al. (1992) *Nucleic Acids Research* 20:6287-6295; Chen, J. et al (1993) *International Immunology* 5:647-656; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol.* Vol. 13:65-93; Harding, F. and Lonberg, N. (1995) *Ann. N.Y. Acad. Sci* 764:536-546; Fishwild, D. et al. (1996) *Nature Biotechnology* 14:845-851. See further, U.S. Pat. Nos. 5,545,806; 5,569,825; 5,625,126; 5,633,425; 5,789, 650; 5,877,397; 5,661,016; 5,814,318; 5,874,299; and 5,770, 429; all to Lonberg and Kay, as well as U.S. Pat. No. 5,545, 807 to Surani et al.; WO 98/24884, WO 94/25585, WO 93/1227, WO 92/22645, WO 92/03918 and WO 01/09187.

The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478.

Immunizations

To generate fully human monoclonal antibodies to CD20, transgenic or transchromosomal mice containing human immunoglobulin genes (e.g., HCo12, HCo7 or KM mice) can be immunized with an enriched preparation of CD20 antigen and/or cells expressing CD20, as described, for example, by Lonberg et al. (1994), supra; Fishwild et al. (1996), supra, and WO 98/24884. Alternatively, mice can be immunized with DNA encoding human CD20. Preferably, the mice will be 6-16 weeks of age upon the first infusion. For example, an enriched preparation (5-50 µg) of the CD20 antigen can be used to immunize the HuMAb mice intraperitoneally. In the event that immunizations using a purified or enriched preparation of the CD20 antigen do not result in antibodies, mice can also be immunized with cells expressing CD20, e.g., a cell line, to promote immune responses.

Cumulative experience with various antigens has shown that the HuMAb transgenic mice respond best when initially immunized intraperitoneally (IP) or subcutaneously (SC) with CD20 expressing cells in complete Freund's adjuvant, followed by every other week IP immunizations (up to a total of 10) with CD20 expressing cells in PBS. The immune response can be monitored over the course of the immunization protocol with plasma samples being obtained by retroorbital bleeds. The plasma can be screened by FACS analysis (as described below), and mice with sufficient titers of anti-CD20 human immunoglobulin can be used for fusions. Mice can be boosted intravenously with CD20 expressing cells 3 days before sacrifice and removal of the spleen.

Generation of Hybridomas Producing Human Monoclonal Antibodies to CD20

To generate hybridomas producing human monoclonal antibodies to human CD20, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag8.653 nonsecreting mouse myeloma cells (ATCC, CRL 1580) with 50% PEG (w/v). Cells can be plated at approximately $1 \times 10^5$ per well in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human kappa-light chain containing antibodies and by FACS analysis using CD20 expressing cells for CD20 specificity. Once extensive hybridoma growth occurs, medium can be observed usually after 10-14 days. The antibody secreting hybridomas can be replated, screened again, and if still positive for human IgG, anti-CD20 monoclonal antibodies can be subcloned at least twice by limiting dilution. The stable subclones can then be cultured in vitro to generate antibody in tissue culture medium for characterization.

Generation of Transfectomas Producing Human Monoclonal Antibodies to CD20

Human antibodies of the invention also can be produced in a host cell transfectoma using, for example, a combination of recombinant DNA techniques and gene transfection methods as is well known in the art (Morrison, S. (1985) Science 229:1202).

For example, in one embodiment, the gene(s) of interest, e.g., human antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells or HEK293 cells or alternatively other eukaryotic cells like a plant derived cells, fungi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Further Recombinant Means for Producing Human Monoclonal Antibodies to CD20

Alternatively, the cloned antibody genes can be expressed in other expression systems, including prokaryotic cells, such as microorganisms, such as E. coli, for the production of single chain Fv antibodies, algi, as well as insect cells. Furthermore, the antibodies can be produced in transgenic non-human animals, such as in milk from sheep and rabbits or in eggs from hens, or in transgenic plants. See e.g. Verma, R., et al. (1998). Antibody engineering: Comparison of bacterial, yeast, insect and mammalian expression systems. *J.Immunol.Meth*. 216:165-181; Pollock, et al. (1999). Transgenic milk as a method for the production of recombinant antibodies. *J.Immunol.Meth*. 231:147-157; and Fischer, R., et al. (1999). Molecular farming of recombinant antibodies in plants. *Biol.Chem*. 380:825-839.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; and Queen, C. et al. (1989) *Proc. Natl. Acad. Sci. U.S.A*. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, *J. Biol. Chem.* 266:19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric IgG1,κ or IgG4,κ antibodies. Similar plasmids can be constructed for expression of other heavy chain isotypes, or for expression of antibodies comprising lambda light chains.

Thus, in another aspect of the invention, the structural features of the human anti-CD20 antibodies of the invention, e.g., 11B8, 2F2, or 7D8, are used to create structurally related human anti-CD20 antibodies that retain at least one functional property of the antibodies of the invention, such as binding to CD20. More specifically, one or more CDR regions of 2F2, 7D8, or 11B8 can be combined recombinantly with known human framework regions and CDRs to create additional, recombinantly-engineered, human anti-CD20 antibodies of the invention.

Accordingly, in another embodiment, the invention provides a method for preparing an anti-CD20 antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in FIGS. 53, 55, or 57 (or corresponding amino acid residues in SEQ ID NOs:13-15, 19-21, or 25-27); and (2) human light chain framework regions and human light chain CDRs, wherein at least one of the human light chain CDRs comprises an amino acid sequence selected from the amino acid sequences of CDRs shown in FIGS. 53, 55 or 57 (or corresponding amino acid residues in SEQ ID NOs: 16-18, 22-24, or 28-30); wherein the antibody retains the ability to bind to CD20.

The ability of the antibody to bind CD20 can be determined using standard binding assays, such as those set forth in the Examples (e.g., a FACS analysis).

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of 2F2, 7D8, or 11B8. The antibodies further can comprise the CDR2s of 2F2, 7D8, or 11B8. The antibodies further can comprise the CDR1s of 2F2, 7D8, or 11B8. Accordingly, the invention further provides anti-CD20 antibodies comprising: (1) human heavy chain framework regions, a human heavy chain CDR1 region, a human heavy chain CDR2 region, and a human heavy chain CDR3 region, wherein the human heavy chain CDR3 region is the CDR3 of 2F2, 7D8, or 11B8 as shown in FIGS. 53, 55, or 57 (or corresponding amino acid residues as shown in SEQ ID NOs: 15, 21, or 27); and (2) human light chain framework regions, a human light chain CDR1 region, a human light chain CDR2 region, and a human light chain CDR3 region, wherein the human light chain CDR3 region is the CDR3 of 2F2, 7D8, or 11B8 as shown in FIGS. 53, 55, or 57 (or corresponding amino acid residues as shown in SEQ ID NOs: 18, 24, or 30), wherein the antibody binds CD20. The antibody may further comprise the heavy chain CDR2 and/or the light chain CDR2 of 2F2, 7D8, or 11B8. The antibody may further comprise the heavy chain CDR1 and/or the light chain CDR1 of 2F2, 7D8, or 11B8.

Preferably, the CDR1, 2, and/or 3 of the engineered antibodies described above comprise the exact amino acid sequence(s) as those of 2F2, 7D8, or 11B8 disclosed herein. However, the ordinarily skilled artisan will appreciate that some deviation from the exact CDR sequences of 2F2, 7D8, or 11B8 may be possible while still retaining the ability of the antibody to bind CD20 effectively (e.g., conservative substitutions). Accordingly, in another embodiment, the engineered antibody may be composed of one or more CDRs that are, for example, 90%, 95%, 98% or 99.5% identical to one or more CDRs of 2F2, 7D8, or 11B8.

In addition to simply binding CD20, engineered antibodies such as those described above may be selected for their retention of other functional properties of antibodies of the invention, such as:

(1) low dissociation rate from CD20;
(2) high affinity binding to CD20;
(3) binding to a unique epitope on CD20, and/or binding in a specific orientation to CD20, and/or binding to a specific form of CD20;
(4) mediation of a high level of CDC on either CD55/59 negative or CD55/59 positive cells;
(5) translocation into lipid rafts upon binding to CD20;
(6) inhibition of the growth of cells which express CD20;
(7) inducement of apoptosis of cells which express CD20;
(8) inducement of homotypic adhesion of cells which express CD20;
(9) prolonged survival of a subject having tumor cells which express CD20;
(10) mediation of ADCC of CD20 targets when mixed with appropriate effector cells;
(11) ability to deplete cells which express CD20; and/or
(12) ability to deplete cells which express low levels of CD20 ($CD20^{low}$ cells).

Characterization of Binding of Human Monoclonal Antibodies to CD20

To purify human anti-CD20 antibodies, selected hybridomas can be grown in two-liter spinner-flasks for monoclonal antibody purification. Supernatants can be filtered and concentrated before affinity chromatography with protein A-sepharose (for IgG1 isotype antibodies) (Pharmacia, Piscataway, N.J.) or anti-human IgG coated sepharose or protein G-sepharose in case of IgG3 isotype antibodies. Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-CD20 monoclonal antibodies bind to unique epitopes, site-directed or multi-site directed mutagenesis can be used.

To determine the isotype of purified antibodies, isotype ELISAs can be performed. Wells of microtiter plates can be coated with 10 μg/ml of anti-human Ig overnight at 4° C. After blocking with 5% BSA, the plates are reacted with 10 μg/ml of monoclonal antibodies or purified isotype controls, at ambient temperature for two hours. The wells can then be reacted with either human IgG1, IgG2, IgG3 or IgG4 or human IgM-specific alkaline phosphatase-conjugated probes. After washing, the plates are developed with pNPP substrate (1 mg/ml) and analyzed at OD of 405-650.

In order to demonstrate presence of anti-CD20 antibodies in sera of immunized mice or binding of monoclonal antibodies to live cells expressing the CD20, flow cytometry can be used. Briefly, cell lines expressing CD20 (grown under standard growth conditions) are mixed with various concentrations of monoclonal antibodies in PBS containing 0.1% BSA and 0.02% sodium-azide, and incubated at 4° C. for 30 min. After washing, the cells are reacted with fluorescein-labeled anti-human IgG antibody under the same conditions as the primary antibody staining. The samples can be analyzed by flow cytometry with a FACS instrument using light and side scatter properties to gate on single, living cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD20 human IgGs can be further tested for reactivity with CD20 antigen by Western blotting. Briefly, cell extracts from cells expressing CD20 can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Phagocytic and Cell Killing Activities of Human Monoclonal Antibodies to CD20

In addition to binding specifically to CD20, human monoclonal anti-CD20 antibodies can be tested for their ability to mediate phagocytosis and killing of cells expressing CD20. The testing of monoclonal antibody activity in vitro will provide an initial screening prior to testing in vivo models. Briefly, polymorphonuclear cells (PMNs), NK cells, monocytes or other effector cells, from healthy donors can be purified by Ficoll Hypaque density centrifugation, followed by lysis of contaminating erythrocytes. Washed PMNs, can be suspended in RPMI supplemented with 10% heat-inactivated fetal calf serum and mixed with $^{51}Cr$ labeled cells expressing CD20, at various ratios of effector cells to tumor cells (-effector cells:tumor cells). Purified human anti-CD20 IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}Cr$ release into the culture supernatant. Anti-CD20 monoclonal antibodies can also be tested in combinations with each other to determine whether cytolysis is enhanced with multiple monoclonal antibodies.

Human monoclonal antibodies which bind to CD20 also can be tested in an in vivo model (e.g., in mice) to determine their efficacy in controlling growth of CD20-expressing tumor cells. These antibodies can be selected, for example, based on the following criteria, which are not intended to be exclusive:

1. binding to live cells expressing CD20;
2. low dissociation rate from CD20;
3. high affinity of binding to CD20;
4. binding to a unique epitope on CD20; and/or binding in a specific orientation to CD20, and/or binding to a specific form of CD20;
5. opsonization of cells expressing CD20;
6. mediation of growth inhibition, phagocytosis and/or killing of cells expressing CD20 in the presence of human effector cells;
7. ability to induce CDC on either CD55/CD59 negative or positive cells;
8. ability to induce homotypic adhesion;
9. ability to induce translocation into lipid rafts upon binding to CD20;
10. ability to induce apoptosis;
11. ability to induce ADCC on cells expressing CD20;
12. ability to deplete cells which express CD20; and/or
13. ability to deplete cells which express low levels of CD20 ($CD20^{low}$ cells).

Preferred human monoclonal antibodies of the invention meet one or more of these criteria.

Human monoclonal anti-CD20 antibodies can be tested for their ability to mediate CDC using a variety of known techniques. For example, serum for complement can be obtained from the blood of healthy subjects which can be centrifuged and harvested. To determine the CDC activity of various mAbs, different methods can be used. $^{51}$Cr release can for example be measured or elevated membrane permeability can be assessed using a propidium iodide (PI) exclusion assay. Briefly, target cells can be washed and resuspended in RPMI-1% BSA at $1\times10^6$/ml. Various concentrations of mAb can be added to the cells and allowed to bind for 10-15 min at room temperature. Serum can then be added to a final concentration of 20% (v/v) and the cells incubated at 37° C. for 45 min. All cells from each sample can be added to the PI solution in a FACS tube. The mixture can then be assessed immediately by flow cytometry using a FACScalibur flow cytometer and analysed using CellQuest pro software (BD Biosciences, Mountain view, Calif.).

To test for the ability to initiate apoptosis, human monoclonal anti-CD20 antibodies can, for example, be incubated with CD20 positive tumor cells, e.g., Daudi at 37° C. for about 20 hours. The cells can be harvested, washed in Annexin-V-FITC binding buffer (BD biosciences), and labeled with Annexin V-FITC (BD biosciences) for 15 min in the dark at 4° C. All cells from each sample can be added to PI solution (10 μg/ml in PBS) in a FACS tube and assessed immediately by flow cytometry (as above).

In a particular embodiment of the invention, the human monoclonal antibodies are used in combination, e.g., as a pharmaceutical composition comprising two or more anti-CD20 monoclonal antibodies. For example, human anti-CD20 monoclonal antibodies having different but complementary activities can be combined in a single therapy to achieve a desired therapeutic or diagnostic effect. In a preferred embodiment, the composition includes an anti-CD20 human monoclonal antibody that mediates CDC combined with another human anti-CD20 monoclonal antibody that induces apoptosis. In another embodiment, the composition includes an anti-CD20 human monoclonal antibody that mediates highly effective killing of target cells in the presence of effector cells, combined with another human anti-CD20 monoclonal antibody that inhibits the growth of cells expressing CD20.

II. Production of Transgenic Non-human Animals which Generate Human Monoclonal Anti-CD20 Antibodies In yet another aspect, the invention provides transgenic and transchromosomal non-human animals, such as transgenic or transchromosomal mice, which are capable of expressing human antibodies that specifically bind to CD20. In a particular embodiment, the invention provides a transgenic or transchromosomal mouse having a genome comprising a human heavy chain transgene, such that the mouse produces human anti-CD20 antibodies when immunized with cells expressing CD20. The human heavy chain transgene can be integrated into the chromosomal DNA of the mouse, as is the case for transgenic, e.g., HuMAb mice, as described in detail herein and exemplified. Alternatively, the human heavy chain transgene can be maintained extrachromosomally, as is the case for transchromosomal (e.g., KM) mice as described in WO 02/43478. Such transgenic and transchromosomal animals are capable of producing multiple isotypes of human monoclonal antibodies to CD20 (e.g., IgG, IgA and/or IgE) by undergoing V-D-J/V-J recombination and isotype switching. The design of a transgenic or transchromosomal non-human animal that responds to foreign antigen stimulation with a heterologous antibody repertoire, requires that the heterologous immunoglobulin transgenes contained within the transgenic animal function correctly throughout the pathway of B cell development. This includes, for example, isotype switching of the heterologous heavy chain transgene. Accordingly, transgenes are constructed so as that isotype switching can be induced and one or more of the following characteristics of antibody genes: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y.

In certain embodiments, the transgenic or transchromosomal non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res*. 15:7305-7316 (1991); Sideras et al., *Intl. Immunol*. 1:631-642 (1989)). For each of the foregoing transgenic animals, functionally rearranged heterologous heavy and light chain immunoglobulin transgenes are found in a significant fraction of the B cells of the transgenic animal (at least 10 percent).

The transgenes used to generate the transgenic non-human animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic animal when exposed to CD20 antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

Preferred transgenic and transchromosomal non-human animals, e.g., mice, will exhibit immunoglobulin production with a significant repertoire, ideally substantially similar to that of a human after adjusting for volume.

The repertoire will ideally approximate that shown in a human when adjusted for volume, usually with a diversity at least about 10% as great, preferably 25 to 50% or more. Generally, at least about a thousand different immunoglobulins (ideally IgG), preferably $10^4$ to $10^6$ or more, will be produced, depending on the number of different V, J and D regions introduced into the mouse genome and driven by the additional diversity generated by V(-D-)J gene segment rearrangements random nucleotide additions at the joining regions. Typically, the immunoglobulins will exhibit an affinity ($K_D$) for preselected antigens of below $10^{-7}$ M, such as of below $10^{-8}$ M, $10^{-9}$ M or $10^{-10}$ M or even lower.

Transgenic and transchromosomal non-human animals, e.g., mice, as described above can be immunized with, for example, cells expressing CD20. Alternatively, the transgenic animals can be immunized with DNA encoding human CD20. The animals will then produce B cells which undergo class-switching via switch recombination (cis-switching) and express immunoglobulins reactive with CD20. The immunoglobulins can be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by a human $V_L$ and $J_L$ or $V_H$, $D_H$ and $J_H$ gene segments, even though other non-germline sequences may be present as a result of somatic mutation and differential V-J and V-D-J recombination joints. The variable regions of each antibody chain are typically at least 80 percent similar to human germline V, J, and, in the case of heavy chains, D, gene segments; frequently at least 85 percent similar to human germline sequences present on the transgene; often 90 or 95 percent or more similar to human germline sequences present on the transgene. However, since non-germline sequences are introduced by somatic mutation and VJ and VDJ joining, the human sequence antibodies will frequently have some variable region sequences which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Another aspect of the invention includes B cells derived from transgenic or transchromosomal non-human animals as described herein. The B cells can be used to generate hybridomas expressing human monoclonal antibodies which bind with high affinity (e.g., a dissociation equilibrium constant ($K_D$) of lower than $10^{-7}$ M) to human CD20. Thus, in another embodiment, the invention provides a hybridoma which produces a human antibody having an affinity ($K_D$) of below $10^{-7}$ M, such as of below $10^{-8}$ M, $10^{-9}$ M or $10^{-10}$ M or even lower when determined by scatchard analysis of CD20 expressing cells using a radio-actively labeled monoclonal antibody or by determination of the half-maximal binding concentration using FACS analysis.

Herein the monoclonal antibody comprises a human sequence light chain composed of (1) a light chain variable region having a polypeptide sequence which is substantially identical to a polypeptide sequence encoded by a human $V_L$ gene segment and a human $J_L$ segment, and (2) a light chain constant region encoded by a human $C_L$ gene segment; and a human sequence heavy chain composed of a (1) a heavy chain variable region having a polypeptide sequence which is substantially identical to a polypeptide sequence encoded by a human $V_H$ gene segment, a D region, and a human $J_H$ segment, and (2) a constant region encoded by a human $C_H$ gene segment.

The development of high affinity human monoclonal antibodies against CD20 can be facilitated by a method for expanding the repertoire of human variable region gene segments in a transgenic non-human animal having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic animal produced by the V repertoire expansion method, wherein the animal expresses an immunoglobulin chain comprising a variable region sequence encoded by a V region gene segment present on the V region transgene and a C region encoded on the human Ig transgene. By means of the V repertoire expansion method, transgenic animals having at least 5 distinct V genes can be generated; as can animals containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a non-human animal germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous. replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic animal having the human Ig transgene(s), and optionally also having a functional YAC having an expanded V segment repertoire. Both $V_H$ and $V_L$ gene segments may be present on the YAC. The transgenic animal may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in three categories:

I. Transgenic animals containing an unrearranged heavy and rearranged light chain immunoglobulin transgene;

II. Transgenic animals containing an unrearranged heavy and unrearranged light chain immunoglobulin transgene; and III. Transgenic animal containing rearranged heavy and an unrearranged light chain immunoglobulin transgene.

Of these categories of transgenic animal, the preferred order of preference is as follows II>I>III where the endogenous light chain genes (or at least the K gene) have been knocked out by homologous recombination (or other method) and I>II>III where the endogenous light chain genes have not been knocked out and must be dominated by allelic exclusion.

III. Bispecific/Multispecific Molecules which Bind to CD20

In yet another embodiment of the invention, human monoclonal antibodies to CD20 can be derivatized or linked to another functional molecule, e.g., another peptide or protein (e.g., an Fab' fragment) to generate a bispecific or multispecific molecule which binds to multiple binding sites or target epitopes. For example, an antibody of the invention can be functionally linked (e.g., by chemical coupling, genetic fusion, noncovalent association or otherwise) to one or more other binding molecules, such as another antibody, peptide or binding mimetic.

Accordingly, the present invention includes bispecific and multispecific molecules comprising at least one first binding specificity for CD20 and a second binding specificity for a second target epitope. In a particular embodiment of the invention, the second target epitope is an Fc receptor, e.g., human FcγRI (CD64) or a human Fcα receptor (CD89), or a T cell receptor, e.g., CD3. Therefore, the invention includes bispecific and multispecific molecules capable of binding both to FcγR, FcαR or FcεR expressing effector cells (e.g., monocytes, macrophages or polymorphonuclear cells (PMNs)), and to target cells expressing CD20. These bispecific and multispecific molecules target CD20 expressing cells to effector cell and, like the human monoclonal antibodies of the invention, trigger Fc receptor-mediated effector cell activities, such as phagocytosis of a CD20 expressing cells, antibody dependent cellular cytotoxicity (ADCC), cytokine release, or generation of superoxide anion.

Bispecific and multispecific molecules of the invention can further include a third binding specificity, in addition to an anti-Fc binding specificity and an anti-CD20 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_C$ receptor or target cell antigen. The "anti-enhancement factor portion" can bind an $F_C$ receptor or a target cell antigen. Alternatively, the anti-enhancement factor portion can bind to an entity that is different from the entity to which the first and second binding specificities bind. For example, the anti-enhancement factor portion can bind a cytotoxic T cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al U.S. Pat. No. 4,946,778. The antibody may also be a binding-domain immunoglobulin fusion protein as disclosed in US 2003/0118592 and US 2003/0133939.

In one embodiment bispecific and multispecific molecules of the invention comprise a binding specificity for an FcγR or an FcαR present on the surface of an effector cell, and a second binding specificity for a target cell antigen, e.g., CD20.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor is a human high affinity FcγRI.

The production and characterization of these preferred monoclonal antibodies are described by Fanger et al. in WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. In other embodiments, the anti-Fcγ receptor antibody is a humanized form of monoclonal antibody 22 (H22). The production and characterization of the H22 antibody is described in Graziano, R. F. et al. (1995) J. Immunol 155 (10):

4996-5002 and WO 94/10332. The H22 antibody producing cell line was deposited at the American Type Culture Collection on Nov. 4, 1992 under the designation HA022CL1 and has the accession No. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al. (1996) Critical Reviews in Immunology 16:423-440). Four FcαRI-specific monoclonal antibodies, identified as A3, A59, A62 and A77, which bind FcαRI outside the IgA ligand binding domain, have been described (Monteiro, R. C. et al. (1992) J. Immunol. 148:1764).

FcαRI and FcγRI are preferred trigger receptors for use in the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

In another embodiment the bispecific molecule is comprised by two human monoclonal antibodies according to the invention which have complementary functional activities, such as one antibody predominately working by inducing CDC and the other antibody predominately working by inducing apoptosis, e.g., 2F2 in combination with 11B8.

In other embodiments, bispecific and multispecific molecules of the invention further comprise a binding specificity which recognizes, e.g., binds to, a target cell antigen, e.g., CD20. In a preferred embodiment, the binding specificity is provided by a human monoclonal antibody of the present invention.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cellular cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets. An effector cell can phagocytose or lyse a target antigen or a target cell.

"Target cell" shall mean any undesirable cell in a subject (e.g., a human or animal) that can be targeted by a composition (e.g., a human monoclonal antibody, a bispecific or a multispecific molecule) of the invention. In preferred embodiments, the target cell is a cell expressing or overexpressing CD20. Cells expressing CD20 typically include B cells and B cell tumors.

While human monoclonal antibodies are preferred, other antibodies which can be employed in the bispecific or multispecific molecules of the invention are murine, chimeric and humanized monoclonal antibodies. Such murine, chimeric and humanized monoclonal antibodies can be prepared by methods known in the art.

Bispecific and multispecific molecules of the present invention can be made using chemical techniques (see e.g., D. M. Kranz et al. (1981) Proc. Natl. Acad. Sci. USA 78:5807), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-CD20 binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohexane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb×Fab, Fab× F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ counter or a scintillation counter or by autoradiography.

IV. Immunoconjugates

In another aspect, the present invention features a human anti-CD20 monoclonal antibody conjugated to a therapeutic moiety, such as a cytotoxin, a drug (e.g., an immunosuppressant) or a radioisotope. Such conjugates are referred to herein as "immunoconjugates". Immunoconjugates which include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies of the present invention also can be conjugated to a radioisotope, e.g., iodine-131, yttrium-90 or indium-111, to generate cytotoxic radiopharmaceuticals for treating a CD20-related disorder, such as a cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

In a further embodiment, the human monoclonal antibodies according to the invention are attached to a linker-chelator, e.g., tiuxetan, which allows for the antibody to be conjugated to a radioisotope.

V. Pharmaceutical Compositions

In another aspect, the present invention provides a composition, e.g., a pharmaceutical composition, containing one or a combination of human monoclonal antibodies of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995. In one embodiment, the compositions include a combination of multiple (e.g., two or more) isolated human antibodies of the invention which act by different mechanisms, e.g., one antibody which predominately acts by inducing CDC in combination with another antibody which predominately acts by inducing apoptosis.

Pharmaceutical compositions of the invention also can be administered in combination therapy, i.e., combined with other agents. For example, the combination therapy can include a composition of the present invention with at least one anti-inflammatory agent or at least one immunosuppressive agent. In one embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin).

In another embodiment, such therapeutic agents include one or more DMARDs, such as methotrexate (Rheumatrex), hydroxychloroquine (Plaquenil), sulfasalazine (Asulfidine), pyrimidine synthesis inhibitors, e.g., leflunomide (Arava), IL-1 receptor blocking agents, e.g., anakinra (Kineret), and TNF-α blocking agents, e.g., etanercept (Enbrel), infliximab (Remicade) and adalimumab.

In another embodiment, such therapeutic agents include one or more immunosuppressive agents, such as cyclosporine (Sandimmune, Neoral) and azathioprine (Imural).

In yet another embodiment, such therapeutic agents include one or more chemotherapeutics, such as doxorubicin (Adriamycin), cisplatin (Platinol), bleomycin (Blenoxane), carmustine (Gliadel), cyclophosphamide (Cytoxan, Procytox, Neosar), and chlorambucil (Leukeran).

In another embodiment, human antibodies of the present invention may be administered in combination with chlorambucil and prednisolone; cyclophosphamide and prednisolone; cyclophosphamide, vincristine, and prednisone; cyclophosphamide, vincristine, doxorubicin, and prednisone; fludarabine and anthracycline; or in combination with other common multi-drugs regimens for NHL, such as disclosed, e.g., in Non-Hodgkin's Lymphomas: Making sense of Diagnosis, Treatment, and Options, Lorraine Johnston, 1999, O'Reilly and Associates, Inc.

In yet another embodiment, the human antibodies may be administered in conjunction with radiotherapy and/or autologous peripheral stem cell or bone marrow transplantation.

In still another embodiment, the human antibodies may be administered in combination with one or more antibodies selected from anti-CD25 antibodies, anti-CD19 antibodies, anti-CD21 antibodies, anti-CD22 antibodies, anti-CD37 antibodies, anti-CD38 antibodies, anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g., natalizumab), and CTLA4-Ig.

In a particular embodiment, the human monoclonal antibodies are administered in combination with an anti-CD25 antibody for the treatment of bullous pemphigoid, e.g., in patients with graft-versus-host disease.

In another particular embodiment, the human monoclonal antibodies are administered in combination with one or more antibodies selected from anti-CD19 anti-bodies, anti-CD21 antibodies, anti-CD22 antibodies, anti-CD37 antibodies, and anti-CD38 antibodies for the treatment of malignant diseases.

In still another particular embodiment, the human antibodies are administered in combination with one or more antibodies selected from anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g natalizumab), and CTLA4-Ig for the treatment of inflammatory diseases.

In yet a further embodiment, the human antibodies may be administered in combination with an anti-C3b(i) antibody in order to enhance complement activation.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In one embodiment the human monoclonal antibodies of the invention are administered in crystalline form by subcutaneous injection, cf. Yang et al., (2003) *PNAS*, 100(12): 6934-6939

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

In one embodiment, the human monoclonal antibodies according to the invention may be administered by infusion in a weekly dosage of 10 to 500 mg/m$^2$, such as 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

In another embodiment, the human monoclonal antibodies are administered by slow continuous infusion over a long period, such as more than 24 hours, in order to reduce toxic side effects.

In still another embodiment the human monoclonal antibodies are administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage can be determined or adjusted by measuring the amount of circulating monoclonal anti-CD20 antibodies upon administration in a biological sample by using anti-idiotypic antibodies which target the anti-CD20 antibodies.

In yet another embodiment, the human monoclonal antibodies are administered by maintenance therapy, such as, e.g., once a week for a period of 6 months or more.

In still another embodiment, the human monoclonal antibodies according to the invention may be administered by a regimen including one infusion of a human monoclonal antibody against CD20 followed by an infusion of a human monoclonal antibody against CD20 conjugated to a radioisotope. The regimen may be repeated, e.g., 7 to 9 days later.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol*. 29:685). Exemplary targeting moieties include folate or biotin (see, e.g., U.S. Pat. No. 5,416,016 to Low et al.); mannosides (Umezawa et al., (1988) *Biochem. Biophys. Res. Commun*. 153:1038); antibodies (P. G. Bloeman et al. (1995) *FEBS Lett*. 357:140; M. Owais et al. (1995) *Antimicrob. Agents Chemother*. 39:180); surfactant protein A receptor (Briscoe et al. (1995) *Am. J. Physiol*. 1233:134), different species of which may comprise the formulations of the inventions, as well as components of the invented molecules; p120 (Schreier et al. (1994) *J. Biol. Chem*. 269:9090); see also K. Keinanen; M. L. Laukkanen (1994) *FEBS Lett*. 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

In a further embodiment, human monoclonal antibodies of the invention can be formulated to prevent or reduce their transport across the placenta. This can be done by methods known in the art, e.g., by PEGylation of the antibodies or by use of F(ab)2' fragments. Further references can be made to "Cunningham-Rundles C, Zhuo Z, Griffith B, Keenan J. (1992) Biological activities of polyethylene-glycol immunoglobulin conjugates. Resistance to enzymatic degradation. *J. Immunol Methods*. 152:177-190; and to "Landor M. (1995) Maternal-fetal transfer of immunoglobulins, *Ann Allergy Asthma Immunol* 74:279-283. This is particularly relevant when the antibodies are used for treating or preventing recurrent spontaneous abortion.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. Alternatively, this property of a composition can be evaluated by examining the ability of the compound to inhibit cell growth or apoptosis by in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A "therapeutically effective dosage" for rheumatoid arthritis preferably will result in an ACR20 Preliminary Definition of Improvement in the patients, more preferred in an ACR50 Preliminary Definition of Improvement and even more preferred in an ARC70 Preliminary Definition of Improvement.

ACR20 Preliminary Definition of Improvement is defined as: ≧20% improvement in: Tender Joint Count (TCJ) and Swollen Joint Count (SWJ) and ≧20% improvement in 3 of following 5 assessments: Patient Pain Assessment (VAS), Patient Global assessment (VAS), Physician Global Assessment (VAS), Patent Self-Assessed Disability (HAQ), Acute Phase Reactant (CRP or ESR).

ACR50 and ACR70 are defined in the same way with ≧50% and ≧70% improvements, respectively. For further details see Felson et al. in American College of Rheumatology Preliminary Definition of Improvement in Rheumatoid Arthritis; Arthritis Rheumatism (1995) 38: 727-735.

The composition must be sterile and fluid to the extent that the composition is deliverable by syringe. In addition to water, the carrier can be an isotonic buffered saline solution; ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VI. Uses and Methods of the Invention

The human antibodies (including immunoconjugates, bispecifics/multispecifics, compositions and other derivatives described herein) of the present invention have numerous in vitro and in vivo diagnostic and therapeutic utilities involving the diagnosis and treatment of disorders involving cells expressing CD20. For example, the antibodies can be administered to cells in culture, e.g., in vitro or ex vivo, or to human subjects, e.g., in vivo, to treat, prevent and to diagnose a variety of disorders. As used herein, the term "subject" is intended to include human and non-human animals which respond to the human antibodies against CD20. Preferred subjects include human patients having disorders that can be corrected or ameliorated by inhibiting or controlling B cells (normal or malignant).

For example, in one embodiment, human antibodies of the present invention can be used to treat a subject with a tumorigenic disorder, e.g., a disorder characterized by the presence of tumor cells expressing CD20 including, for example, B cell lymphoma, e.g., NHL. Examples of tumorigenic diseases which can be treated and/or prevented include B cell lymphoma, e.g., NHL, including precursor B cell lymphoblastic leukemia/lymphoma and mature B cell neoplasms, such as B cell chronic lymhocytic leukemia(CLL)/small lymphocytic lymphoma (SLL), B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, post-transplant lymphoproliferative disorder, Waldenström's macroglobulinemia, and anaplastic large-cell lymphoma (ALCL).

Further examples of B cell non-Hodgkin's lymphomas are lymphomatoid granulomatosis, primary effusion lymphoma, intravascular large B cell lymphoma, mediastinal large B cell lymphoma, heavy chain diseases (including γ, μ, and α disease), lymphomas induced by therapy with immunosuppressive agents, such as cyclosporine-induced lymphoma, and methotrexate-induced lymphoma.

In a further embodiment, the human antibodies of the present invention can be used to treat Hodgkin's lymphoma.

Examples of immune disorders in which CD20 expressing B cells are involved which can be treated and/or prevented include autoimmune disorders, such as psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behcet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, HIV, and herpes virus associated diseases. Further examples are severe acute respiratory distress syndrome and choreoretinitis. Furthermore, other diseases and disorders include those caused by or mediated by infection of B-cells with virus, such as Epstein-Barr virus (EBV).

Further examples of inflammatory, immune and/or autoimmune disorders in which autoantibodies and/or excessive B lymphocyte activity are prominent and which can be treated and/or prevented, include the following:

vasculitides and other vessel disorders, such as microscopic polyangiitis, Churg-Strauss syndrome, and other ANCA-associated vasculitides, polyarteritis nodosa, essential cryoglobulinaemic vasculitis, cutaneous leukocytoclastic angiitis, Kawasaki disease, Takayasu arteritis, giant cell arthritis, Henoch-Schönlein purpura, primary or isolated cerebral angiitis, erythema nodosum, thrombangiitis obliterans, thrombotic thrombocytopenic purpura (including hemolytic uremic syndrome), and secondary vasculitides, including cutaneous leukocytoclastic vasculitis (e.g., secondary to hepatitis B, hepatitis C, Waldenström's macroglobulinemia, B-cell neoplasias, rheumatoid arthritis, Sjögren's syndrome, or systemic lupus erythematosus); further examples are erythema nodosum, allergic vasculitis, panniculitis, Weber-Christian disease, purpura hyperglobulinaemica, and Buerger's disease;

skin disorders, such as contact dermatitis, linear IgA dermatosis, vitiligo, pyoderma gangrenosum, epidermolysis bullosa acquisita, pemphigus vulgaris (including cicatricial pemphigoid and bullous pemphigoid), alopecia areata (including alopecia universalis and alopecia totalis), dermatitis herpetiformis, erythema multiforme, and chronic autoimmune urticaria (including angioneurotic edema and urticarial vasculitis);

immune-mediated cytopenias, such as autoimmune neutropenia, and pure red cell aplasia;

connective tissue disorders, such as CNS lupus, discoid lupus erythematosus, CREST syndrome, mixed connective tissue disease, polymyositis/dermatomyositis, inclusion body myositis, secondary amyloidosis, cryoglobulinemia type I and type II, fibromyalgia, phospholipid antibody syndrome, secondary hemophilia, relapsing polychondritis, sarcoidosis, stiff man syndrome, and rheumatic fever; a further example is eosinophil fasciitis;

arthritides, such as ankylosing spondylitis, juvenile chronic arthritis, adult Still's disease, and SAPHO syndrome; further examples are sacroileitis, reactive arthritis, Still's disease, and gout;

hematologic disorders, such as aplastic anemia, primary hemolytic anemia (including cold agglutinin syndrome), hemolytic anemia secondary to CLL or systemic lupus erythematosus; POEMS syndrome, pernicious anemia, and Waldemström's purpura hyperglobulinaemica; further examples are agranulocytosis, autoimmune neutropenia, Franklin's disease, Seligmann's disease, μ-chain disease, paraneoplastic syndrome secondary to thymoma and lymphomas, and factor VIII inhibitor formation;

endocrinopathies, such as polyendocrinopathy, and Addison's disease; further examples are autoimmune hypoglycemia, autoimmune hypothyroidism, autoimmune insulin syndrome, de Quervain's thyroiditis, and insulin receptor antibody-mediated insulin resistance;

hepato-gastrointestinal disorders, such as celiac disease, Whipple's disease, primary biliary cirrhosis, chronic active hepatitis, and primary sclerosing cholangiitis; a further example is autoimmune gastritis;

nephropathies, such as rapid progressive glomerulonephritis, post-streptococcal nephritis, Goodpasture's syndrome, membranous glomerulonephritis, and cryoglobulinemic nephritis; a further example is minimal change disease;

neurological disorders, such as autoimmune neuropathies, mononeuritis multiplex, Lambert-Eaton's myasthenic syndrome, Sydenham's chorea, tabes dorsalis, and Guillain-Barré's syndrome; further examples are myelopathy/tropical spastic paraparesis, myasthenia gravis, acute inflammatory demyelinating polyneuropathy, and chronic inflammatory demyelinating polyneuropathy;

cardiac and pulmonary disorders, such as fibrosing alveolitis, bronchiolitis obliterans, allergic aspergillosis, cystic fibrosis, Löffler's syndrome, myocarditis, and pericarditis; further examples are hypersensitivity pneumonitis, and paraneoplastic syndrome secondary to lung cancer;

allergic disorders, such as bronchial asthma and hyper-IgE syndrome; a further example is amaurosis fugax;

ophthalmologic disorders, such as idiopathic chorioretinitis;

infectious diseases, such as parvovirus B infection (including hands-and-socks syndrome); and gynecological-obstretical disorders, such as recurrent abortion, recurrent fetal loss, and intrauterine growth retardation; a further example is paraneoplastic syndrome secondary to gynaecological neoplasms;

male reproductive disorders, such as paraneoplastic syndrome secondary to testicular neoplasms; and transplantation-derived disorders, such as allograft and xenograft rejection, and graft-versus-host disease.

In one embodiment, the disease is an inflammatory, immune and/or autoimmune disorder selected from ulcerative colitis, Crohn's disease, juvenile onset diabetes, multiple sclerosis, immune-mediated thrombocytopenias, such as acute idiopathic thrombocytopenic purpura and chronic idiopathic thrombocytopenic purpura, hemolytic anemia (including autoimmune hemolytic anemia), myasthenia gravis, systemic sclerosis, and pemphigus vulgaris.

In another embodiment, human antibodies of the invention can be used to detect levels of CD20, or levels of cells which contain CD20 on their membrane surface, which levels can then be linked to certain disease symptoms. Alternatively, the antibodies can be used to deplete or interact with the function of CD20 expressing cells, thereby implicating these cells as important mediators of the disease. This can be achieved by contacting a sample and a control sample with the anti-CD20 antibody under conditions that allow for the formation of a complex between the antibody and CD20. Any complexes formed between the antibody and CD20 are detected and compared in the sample and the control.

Human antibodies of the invention can be initially tested for binding activity associated with therapeutic or diagnostic use in vitro. For example, the antibodies can be tested using flow cytometric assays described in the Examples below. Moreover, activity of the antibodies in triggering at least one effector-mediated effector cell activity, including inhibiting the growth of and/or killing of cells expressing CD20, can be assayed. For example, the ability of the antibodies to trigger CDC and/or apoptosis can be assayed. Protocols for assaying for CDC, homotypic adhesion, molecular clustering or apoptosis are described in the Examples below.

Human antibodies of the invention also have additional utility in therapy and diagnosis of a variety of CD20-related diseases. For example, the human antibodies can be used to elicit in vivo or in vitro one or more of the following biological activities: to inhibit the growth of and/or differentiation of a cell expressing CD20; to kill a cell expressing CD20; to mediate phagocytosis or ADCC of a cell expressing CD20 in the presence of human effector cells; to mediate CDC of a cell expressing CD20 in the presence of complement; to mediate apoptosis of a cell expressing CD20; to induce homotypic adhesion; and/or to induce translocation into lipid rafts upon binding CD20.

In a particular embodiment, the human antibodies are used in vivo to treat, prevent or diagnose a variety of CD20-related diseases. Examples of CD20-related diseases include, among others, B cell lymphoma, e.g., NHL, and immune diseases, e.g., autoimmune diseases, such as those listed above.

In a particular embodiment, the antibodies of the invention are used to treat or to prevent NHL, as the antibodies deplete the CD20 bearing tumor cells).

Non-Hodgkin's lymphoma is a type of B cell lymphoma. Lymphomas, e.g., B cell lymphomas, are a group of related cancers that arise when a lymphocyte (a blood cell) becomes malignant. The normal function of lymphocytes is to defend the body against invaders: germs, viruses, fungi, even cancer. There are many subtypes and maturation stages of lymphocytes and, therefore, there are many kinds of lymphomas. Like normal cells, malignant lymphocytes can move to many parts of the body. Typically, lymphoma cells form tumors in the lymphatic system: bone marrow, lymph nodes, spleen, and blood. However, these cells can migrate to other organs. Certain types of lymphoma will tend to grow in locations in which the normal version of the cell resides. For example, it's common for follicular NHL tumors to develop in the lymph nodes.

CD20 is usually expressed at elevated levels on neoplastic (i.e., tumorigenic) B cells associated with NHL. Accordingly, CD20 binding antibodies of the invention can be used to deplete CD20 bearing tumor cells which lead to NHL and, thus, can be used to prevent or treat this disease.

Human antibodies (e.g., human monoclonal antibodies, multispecific and bispecific molecules) of the present invention also can be used to block or inhibit other effects of CD20. For example, it is known that CD20 is expressed on B lymphocytes and is involved in the proliferation and/or differentiation of these cells. Since B lymphocytes function as immunomodulators, CD20 is an important target for antibody mediated therapy to target B lymphocytes, e.g., to inactivate or kill B lymphocytes, involved in autoimmune disorders. Such autoimmune disorders include, for example, the above listed diseases Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition. Furthermore, tumor load can be determined and used to calculate suitable dosages.

As previously described, human anti-CD20 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin, cisplatin, bleomycin, carmustine, chlorambucil, and cyclophosphamide. Co-administration of the human anti-CD20 antibodies of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$ to $10^9$ but will vary depending on the therapeutic purpose. In general, the amount will be sufficient to obtain localization at the target cell, e.g., a tumor cell expressing CD20, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-CD20 antibodies linked to anti-Fc-γRI or anti-CD3 may be used in conjunction with IgG- or IgA-receptor specific binding agents.

Bispecific and multispecific molecules of the invention can also be used to modulate FcγR or FcαR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately. Binding of the compositions of the present invention to target cells causes translocation of the CD20 antigen-antibody complex into lipid rafts of the cell membrane. Such translocation creates a high density of antigen-antibody complexes which may efficiently activate and/or enhance CDC.

Also within the scope of the present invention are kits comprising the antibody compositions of the invention (e.g., human antibodies and immunoconjugates) and instructions for use. The kit can further contain one or more additional reagents, such as an immunosuppressive reagent, a cytotoxic agent or a radiotoxic agent, or one or more additional human antibodies of the invention (e.g., a human antibody having a complementary activity).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcα receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of the invention can also be used to target cells expressing FcγR or CD20, for example for labeling such cells. For such use, the binding agent can be linked to a molecule that can be detected. Thus, the invention provides methods for localizing ex vivo or in vitro cells expressing Fc receptors, such as FcγR, or CD20. The detectable label can be, e.g., a radioisotope, a fluorescent compound, an enzyme, or an enzyme co-factor.

In a particular embodiment, the invention provides methods for detecting the presence of CD20 antigen in a sample, or measuring the amount of CD20 antigen, comprising contacting the sample, and a control sample, with a human monoclonal antibody which specifically binds to CD20, under conditions that allow for formation of a complex between the antibody or portion thereof and CD20. The formation of a complex is then detected, wherein a difference complex formation between the sample compared to the control sample is indicative the presence of CD20 antigen in the sample. In other embodiments, the invention provides methods for treating a disorder involving cells expressing CD20 in a subject, e.g., non-Hodgkin's lymphoma or rheumatoid arthritis, by administering to the subject the human antibodies described above. Such antibodies and derivatives thereof are used to inhibit CD20 induced activities associated with certain disorders, e.g., proliferation and/or differentiation. By contacting the antibody with CD20 (e.g., by administering the antibody to a subject), the ability of CD20 to induce such activities is inhibited and, thus, the associated disorder is treated.

Accordingly, in another embodiment, the present invention provides a method for treating or preventing a tumorigenic disorder involving CD20 expressing cells, e.g., NHL. The method involves administering to a subject an antibody composition of the present invention in an amount effective to treat or prevent the disorder. The antibody composition can be administered alone or along with another therapeutic agent, such as a cytotoxic or a radiotoxic agent which acts in conjunction with or synergistically with the antibody composition to treat or prevent the diseases involving CD20 expressing cells. In a particularly preferred embodiment, the present invention provides a method for treating non-Hodgkin's lymphoma.

In another embodiment, the present invention provides a method for treating or preventing an autoimmune disorder involving human CD20 expressing cells, e.g., those diseases as listed above. The method involves administering to a subject an antibody composition of the present invention in an amount effective to treat or prevent the disorder. The antibody composition can be administered alone or along with another therapeutic agent, such as an immunosuppressant which acts in conjunction with or synergistically with the antibody composition to treat or prevent the disease involving cells expressing CD20.

In still another embodiment, the invention provides a method for detecting the presence or quantifying the amount of CD20-expressing cells in vivo or in vitro. The method comprises (i) administering to a subject a composition (e.g., a multi-or bispecific molecule) of the invention conjugated to a detectable marker; (ii) exposing the subject to a means for detecting said detectable marker to identify areas containing CD20-expressing cells. In yet another embodiment, immunoconjugates of the invention can be used to target compounds (e.g., therapeutic agents, labels, cytotoxins, radiotoxins immunosuppressants, etc.) to cells which have CD20 expressed on their surface by linking such compounds to the antibody. Thus, the invention also provides methods for localizing ex vivo or in vitro cells expressing CD20, such as Reed-Stemberg cells (e.g., with a detectable label, such as a radioisotope, a fluorescent compound, an enzyme, or an enzyme co-factor). Alternatively, the immunoconjugates can be used to kill cells which have CD20 expressed on their surface by targeting cytotoxins or radiotoxins to CD20.

The present invention is further illustrated by the following examples which should not be construed as further limiting.

EXAMPLES

| B-cell lines used in the examples | | |
| --- | --- | --- |
| Cell line | Origin | Obtained from |
| Daudi | Negroid Burkitt's Lymphoma | ECACC (85011437) |
| ARH-77 | IgG plasma cell leukemia | DSMZ (ACC 512) |
| DOHH | Refractory immunoblastic B cell lymphoma | DSMZ (ACC 47) |
| Raji | Negroid Burkitt's Lymphoma | ECACC (85011429) |
| SU-DHL-4 | B-NHL, diffuse histiocytic lymphoma | DSMZ (ACC 495) |
| Ramos-EHRB | Burkitt's Lymphoma | ECACC (85030804) |
| Tanoue | Human B-cell leukemia | DSMZ (ACC 399) |

Daudi, ARH-77, DOHH, Raji, Ramos-EHRB, and Tanoue B-cell lines were cultured in RPMI 1640 culture medium supplemented with 10% fetal calf serum (FCS) (Optimum C241, Wisent Inc., st. Bruno, Canada), 2 mM L-glutamine, 100 IU/ml penicillin, 100 μg/ml streptomycin, and 1 mM sodium pyruvate (all Gibco BRL, Life Technologies, Paisley, Scotland).

SU-DHL-4 B-cell line was cultured in the same medium but without sodium pyruvate.

Cultures were maintained at 37° C. in a humidified 5% $CO_2$ incubator, split and harvested at 80-90% confluence. Medium was refreshed twice a week. At this time cells were split and seeded out to $1$-$1.5 \times 10^6$ cells/ml to ensure viability and optimal growth.

Example 1

Production of Human Antibodies Against CD20

HCo7 and KM Mice: Fully human monoclonal antibodies to CD20 were prepared using HCo7 and KM mice which express human antibody genes. In the KM mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. This mouse strain carries a human kappa light chain transgene, KCo5, as described in Fishwild et al. (1996) *Nature Biotechnology* 14:845-851. This mouse strain also carries a human heavy chain transchromosome composed of chromosome 14 fragment hCF (SC20) as described in WO 02/43478.

The HCo7 mice have a JKD disruption in their endogenous light chain (kappa) genes (as described in Chen et al. (1993) *EMBO J.* 12: 821-830), a CMD disruption in their endogenous heavy chain genes (as described in Example 1 of WO 01/14424), a KCo5 human kappa light chain transgene (as described in Fishwild et al. (1996) *Nature Biotechnology* 14:845-851), and a HCo7 human heavy chain transgene (as described in U.S. Pat. No. 5,770,429).

HCo7 and KM Mice Immunizations: HCo7 and KM mice were immunized with human CD20 transfected NS/0 cells. For the first immunization, per mouse, $1 \times 10^7$ cells in 150 μl PBS were mixed 1:1 with Complete Freunds Adjuvant and injected intra-peritoneally (i.p.). Subsequent i.p. immunizations were done using a similar amount of cells without adjuvant. Three and two days prior to fusion the mice were intravenously boosted with $0.5 \times 10^7$ cells suspended in PBS.

The presence of antibodies directed against human CD20 in the serum of the mice was monitored by flow cytometry using FACS analysis, using human CD20 transfected NS/0 cells as well as CD20 negative parental NS/0 cells.

Generation of hybridomas Producing Human Monoclonal Antibodies to CD20: The mouse splenocytes were isolated from the HCo7 and KM mice and fused with PEG to a mouse myeloma cell line based upon standard protocols. The resulting hybridomas were then screened for human IgG,κ production by ELISA and for CD20 specificity using human CD20 transfected NS/0 and SKBR3 cells by FACS analysis. Single cell suspensions of splenic lymphocytes from immunized mice were fused to one-fourth the number of SP2/0 nonsecreting mouse myeloma cells (ATCC, CRL 1581) with 50% PEG (Sigma). Cells were plated at approximately $1 \times 10^5$/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by flow cytometry for human anti-CD20 monoclonal IgG antibodies. Once extensive hybridoma growth occurred, medium was monitored usually after 10-14 days. The antibody secreting hybridomas were replated, screened again and, if still positive for human IgG, anti-CD20 monoclonal antibodies were subcloned by limiting dilution. The stable subclones were then cultured in vitro to generate small amounts of antibody in tissue culture medium for characterization. One clone from each hybridoma, which retained the reactivity of parent cells (by FACS), was chosen. 5-10 vial cell banks were generated for each clone and stored in liquid nitrogen.

Selection of Human Monoclonal Antibodies Binding to CD20/Primary Screens: To determine the isotype of antibodies, an isotype ELISA was performed. Wells of microtiter plates were coated with 1 μg/ml of mouse anti-human kappa light chain, 50 μl/well in PBS incubated 4° C. overnight. After blocking with 5% chicken serum, the plates were reacted with supernatant and purified isotype control. Plates were then incubated at ambient temperature for 1-2 hours. The wells were then reacted with either human IgG1, IgG2, IgG3 or IgG4-specific Horseradish peroxidase—conjugated probes. Plates were developed and analyzed as described above.

Four hybridoma cell lines were generated, three from fusion of KM mouse and one from fusion of HCo7 mouse, expressing the following antibodies:

2F2: a human monoclonal IgG1,κ antibody with the nucleotide sequences: SEQ ID NOs: 1 and 3 and the amino acid sequences: SEQ ID NOs: 2 and 4.

4C9: a human monoclonal IgG1,κ antibody with exactly the same amino acid sequences as 2F2: SEQ ID NOs: 2 and 4.

7D8: a human monoclonal IgG1,κ antibody with the nucleotide sequences: SEQ ID NOs: 5 and 7 and the amino acid sequences: SEQ ID NOs: 6 and 8.

11B8: a human monoclonal IgG3, κ antibody with the nucleotide sequences: SEQ ID NOs: 9 and 11 and the amino acid sequences: SEQ ID NOs: 10 and 12.

The term "2F2" is used herein to designate both the antibody derived from hybridoma clone 2F2 and the identical antibody derived from hybridoma clone 4C9.

The antibodies of the invention can be switched to other isotypes as determined by the transgenic or transchromosomal non-human animal from which they are derived. In one embodiment of the invention, the 11B8 human monoclonal IgG3,κ antibody can be switched to a human monoclonal IgG1,κ isotype having exactly the same $V_H$ and $V_L$ sequences. In another embodiment, the 2F2 IgG1,κ antibody or 7D8 IgG1,κ antibody can be switched to a human monoclonal IgG2, IgG4, IgA1, IgA2 or IgE isotype having exactly the same $V_H$ and $V_L$ sequences.

Example 2

Antibody Sequencing of Human Antibodies Against CD20

Sequencing of the $V_L$ and $V_H$ Regions

RNA preparation: Total RNA was prepared from $5 \times 10^6$ cells of all HuMAb CD20 hybridoma cell lines (2F2, 7D8 and 11B8) with RNeasy kit (Qiagen, Westburg, Leusden, Netherlands) according to the manufacturer's protocol.

cDNA preparation of 2F2 and 7D8: 5'-RACE-Ready Complementary DNA (cDNA) of RNA was prepared from 1 μg total RNA, using the SMART RACE cDNA Amplification kit (Clonetech), following the manufacturer's protocol.

$V_H$ and $V_L$ regions were amplified using an advantage HF 2 PCR Kit (Clonetech, BD) and using the following primers:

```
V_K RACE2 5' GCA GGC ACA CAA CAG AGG CAG TTC CAG ATT TCanneals in C-kappa
             (SEQ ID NO:31)

V_H RACE2 5' GCT GTG CCC CCA GAG GTG CTC TTG GAG G     anneals in C_H1
             (SEQ ID NO:32)
``` cDNA preparation of 11B8: Complementary DNA (cDNA) of RNA from 11B8 cells was prepared from 3 μg total RNA with AMV Reverse Transcriptase with buffer (Roche Diagnostics GmbH, Mannheim, Germany), oligo d(T)$_{15}$ (Promega, Madison, Wis., USA), dNTP (Roche Diagnostics GmbH, Mannheim, Germany) and RNAsin (Promega) according to the manufacturer's protocol (2000, version 3).

PCR primers used to amplify $V_H$ and $V_L$ regions for cloning:

```
Primer pairs used:

V_H: FR1 5' primers
```

```
Primer pairs used:

AB62              CAg gTK CAg CTg gTg CAg TC         (SEQ ID NO:33)

AB63              SAg gTg CAg CTg KTg gAg TC         (SEQ ID NO:34)

AB65              gAg gTg CAg CTg gTg CAg TC         (SEQ ID NO:35)

V_H leader 5' primers

AB85              ATg gAC Tgg ACC Tgg AgC ATC        (SEQ ID NO:36)

AB86              ATg gAA TTg ggg CTg AgC Tg         (SEQ ID NO:37)

AB87              ATg gAg TTT ggR CTg AgC Tg         (SEQ ID NO:38)

AB88              ATg AAA CAC CTg Tgg TTC TTC        (SEQ ID NO:39)

AB89              ATg ggg TCA ACC gCC ATC CT         (SEQ ID NO:40)

V_H 3' primer
    AB90              TgC CAg ggg gAA gAC CgA Tgg        (SEQ ID NO:41)
    V_K: FR1 5' primers
    AB8               RAC ATC CAg ATg AYC CAg TC         (SEQ ID NO:42)

AB9               gYC ATC YRg ATg ACC CAg TC         (SEQ ID NO:43)

AB10              gAT ATT gTg ATg ACC CAg AC         (SEQ ID NO:44)

AB11              gAA ATT gTg TTg ACR CAg TC         (SEQ ID NO:45)

AB12              gAA ATW gTR ATg ACA CAg TC         (SEQ ID NO:46)

AB13              gAT gTT gTg ATg ACA CAG TC         (SEQ ID NO:47)

AB14              gAA ATT gTg CTg ACT CAg TC         (SEQ ID NO:48)

V_K leader 5' primers
    AB123             CCC gCT Cag CTC CTg ggg CTC CTg    (SEQ ID NO:49)

AB124             CCC TgC TCA gCT CCT ggg gCT gC     (SEQ ID NO:50)

AB125             CCC AgC gCA gCT TCT CTT CCT CCT gC (SEQ ID NO:51)

AB126             ATg gAA CCA Tgg AAg CCC CAg CAC AgC(SEQ ID NO:52)

V_K 3' primer
    AB16              Cgg gAA gAT gAA gAC AgA Tg         (SEQ ID NO:53)

wherein K = T or G, S = C or G, R = A or G, Y = C or T, and W = A or T.
```

PCR conditions used to amplify $V_H$ and $V_L$ regions for cloning 2F2 and 7D8: Polymerase chain reactions (PCR) were performed with HF polymerase mix (Clonetech.) on a T1 cycler (Biometra, Westburg).

PCR conditions:

| | |
|---|---|
| 94° C. 30 sec | |
| 72° C. 1 min | 5 cycles |
| 94° C. 30 sec | |
| 70° C. 30 sec | 5 cycles |
| 72° C. 1 min | |
| 94° C. 30 sec | |
| 68° C. 30 sec | 27-30 cycles |
| 72° C. 1 min | |

PCR conditions used to amplify $V_H$ and $V_L$ regions for cloning 11B8: Polymerase chain reactions (PCR) were performed with AmpliTaq polymerase (Perkin Elmer) on a T1 Cycler (Biometra, Westburg, Leusden, Netherlands).

| PCR cycling protocol: | |
|---|---|
| | 94° C. 2 min |
| 11 cycles | 94° C. 30 sec |
| | 65° C. 30 sec, minus 1° C. per cycle |
| | 72° C. 30 sec |
| 30 cycles | 94° C. 30 sec |
| | 55° C. 30 sec |
| | 72° C. 30 sec |
| | 72° C. 10 min |
| cool down to 4° C. | |

Cloning of $V_H$ and $V_L$ in pGEMT-Vector System II (2F2, 7D8, and 11B8): After analysing the PCR products on an agarose gel, the products were purified with the QIAEX II Gel Extraction Kit (Qiagen, Westburg, Leusden, Netherlands). Two independently amplified PCR products of each $V_H$ and $V_L$ region were cloned in pGEMT-Vector System II (Promega) according to manufacturer's protocol (1999, version 6).

After transformation to E. coli JM109, individual colonies were screened by colony PCR using T7 and SP6 primers, 30 annealing cycles at 55° C. Plasmid DNA from colonies was purified using Qiaprep Spin miniprep kit (Qiagen). To further analyse the $V_H$ and $V_L$ regions, a Nco1/Not1 (NE Biolabs, Westburg, Leusden, Netherlands) digestion was performed and analysed on agarose gel.

Sequencing (2F2, 7D8 and 11B8): The V-regions regions were sequenced after cloning in the pGEMT-Vector System II. Sequencing was performed at Baseclear (Leiden, Netherlands). The sequences were analyzed by aligning germline V-gene sequences in Vbase (www.mrc-cpe.cam.ac.uk/imt-doc/public/intro.htm).http://www.mrc-cpe.cam.ac.uk/vbase-ok.php?menu=901.

The sequences obtained are shown in FIGS. 53-58.

Example 3

Recombinant Production of 2F2 and 11B8 in GS-NS/0 Cell Line

2F2T: The heavy chain and light chain variable regions of the 2F2 antibody were amplified, using PCR, from a standard cloning vector, pGem-5Zf (Promega), using primers which included an optimal Kozak sequence and suitable restriction sites to clone the fragments in the GS constant region vectors pCONγ1f and PCONκ (Lonza).

Figure 2:
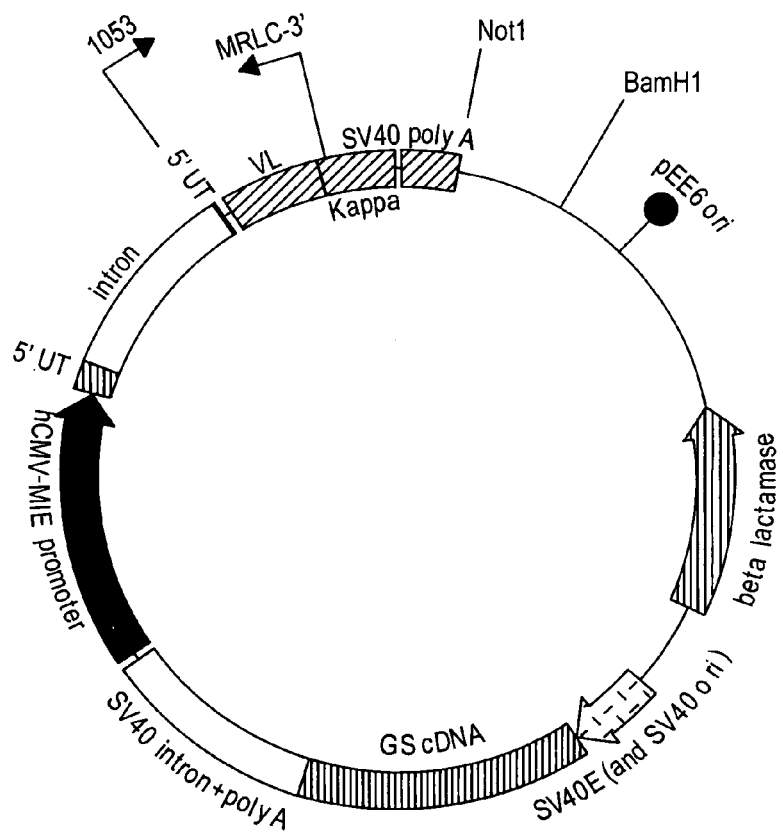
FIG. 2 shows the pCONκ/variable-light vector used for recombinant production of 2F2 and 11B8.

After amplification, the fragments were purified and digested with the restriction enzymes for cloning and ligated in the two vectors. The heavy chain variable fragment was digested with Hind III and Bsi WI and ligated into the pCONγ1f vector which had been digested with Hind III and Bsi WI, and dephosphorylated with alkaline phosphatase. The light chain variable fragment was digested with Hind III and Apa I and ligated into the PCONκ vector which had been digested with Hind III and Apa I, and dephosphorylated with alkaline phosphatase. The pCONγ1f/variable-heavy and PCONκ/variable-light vectors are shown in FIGS. 1 and 2, respectively. Transformed *E. coli* colonies were checked by colony PCR and 2 positive colonies of each the heavy chain (HC) and light chain (LC) construct were grown for plasmid isolation. Isolated plasmid of these 4 clones was sequenced to confirm the sequence. Both of the HC clones and one of the LC clones were found to have the correct sequences.

The two HC and one LC constructs were combined to give two combinations of LC-HC and transiently co-transfected in CHO-K1 cells to check the constructs for proper production of 2F2 antibody. Normal production levels were reached for all combinations in this expression experiment and 1 clone of each of the HC and LC constructs were chosen for construction of a double-gene vector.

Figure 3:
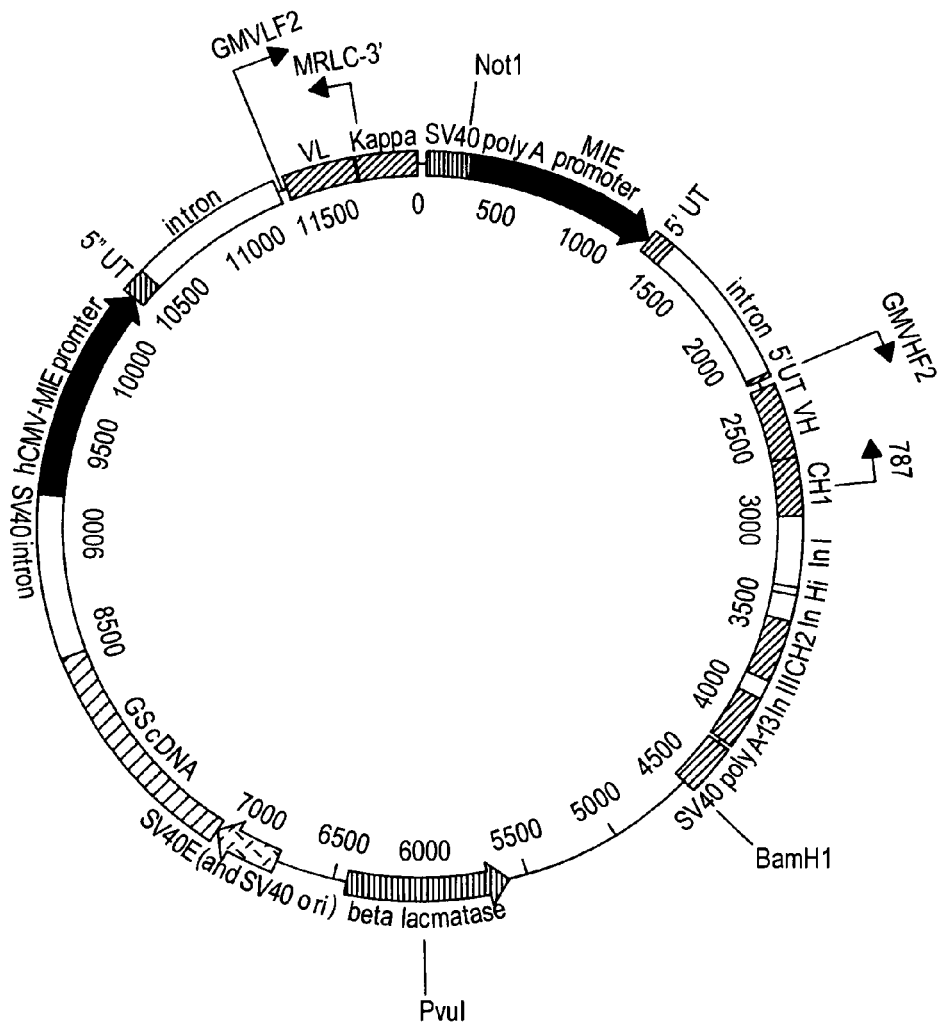
FIG. 3 shows the double-gene cloning vector (pCON-γ1f/κ2F2) used for recombinant production of 2F2 and 11B8.

Standard cloning procedures were used to combine the HC and LC constructs in a double-gene cloning vector, designated pCONγ1f/κ2F2, by ligating the complete expression cassette from the heavy chain vector, pCONγ1f/variable-heavy, into the light chain vector, pCONκ/variable-light. The pCONγ1f/κ2F2 vector is shown in FIG. 3.

This construct was again functionally tested in a transient transfection in CHO-K1 cells and showed normal expression levels.

The variable regions of the pCONγ1f/κ2F2 plasmid were sequenced to reconfirm the correct sequences.

Linear plasmid was prepared for stable transfections by digesting pCONγ1f/κ2F2 with a unique restriction enzyme, Pvu I, cutting outside regions vital for expression. Complete linearization was confirmed by agarose gel electrophoresis and the DNA was purified and stored at −20° C. until use.

Six transfections of NS/0 host cells were performed, by electroporation with plasmid DNA, using the above linear DNA plasmid. Following transfection, the cells were distributed into 96-wells plates and incubated. Selective medium (containing 10% dialysed fetal calf serum (dFCS) and 10 μM of the GS-inhibitor L-methionine sulphoximine but lacking glutamine) was added and the plates were monitored to determine when the non-transfected cells died to leave foci of transfected cells. For further details concerning GS vector systems, see WO 87/04462. The transfected plates were incubated for approximately three weeks to allow colony formation. The resulting colonies were examined microscopically to verify that the colonies were of a suitable size for assay (covering greater than 60% of the bottom of the well), and that only one colony was present in each well. Cell supernatants from 436 transfectants were screened for assembled antibody by IgG,κ-ELISA. Using this data, 111 transfectants were selected for progression and further assessment in static culture. Cultures of the selected cell lines were expanded and adapted to low-serum containing medium (containing bovine serum albumin (BSA) and added 1% dFCS) and a further assessment of productivity in static culture was undertaken (ELISA and measurement of percentage confluence). The 65 highest ranking cell lines were selected for progression. A preliminary assessment of the productivity of the selected cell lines was made in batch shake flask suspension culture in low serum-containing medium (containing BSA and added 1% dFCS). Based upon harvest antibody concentration (by ELISA) and acceptable growth characteristics, 30 cell lines were selected for further evaluation in serum-free medium using a batch shake flask suspension culture. The 10 cell lines that produced the highest antibody concentrations were further evaluated in duplicate fed-batch shake flask suspension cultures in serum-free medium. Product concentrations at harvest were determined by protein A high performance liquid chromatography (HPLC), according to well-known standard methods. All cell lines produced 2F2 antibody (denoted 2F2T) in good yields in the range of from 671-1333 mg/L as determined by protein A HPLC.

11B8T: In a similar way a GS-NS/0 cell line was established for recombinant production of 11B8 (denoted 11B8T) modifying the transfection procedure slightly as follows.

Four transfections of NS/0 host cells were performed, by electroporation with plasmid DNA, using the above linear DNA plasmid. After examining the resulting colonies microscopically to verify that the colonies were of a suitable size for assay (covering greater than 60% of the bottom of the well) and that only one colony was present in each well, cell supernatants from 596 transfectants were screened for assembled antibody by IgG,κ-ELISA. Using this data, 100 transfectants were selected for progression and further assessment in static culture. Cultures of the selected cell lines were expanded and adapted to low-serum containing medium (containing bovine serum albumin (BSA) and added 1% dFCS) and a further assessment of productivity in static culture was undertaken (ELISA and measurement of percentage confluence). The 60 highest ranking cell lines were selected for progression, and an additional 13 cell lines for which productivity data was unavailable were also progressed. A preliminary assessment of the productivity of the selected cell lines was made in batch shake flask suspension culture in low serum-containing medium (containing BSA and added 1% dFCS). Based upon harvest antibody concentration (by ELISA) and acceptable growth characteristics, 10 cell lines were selected for further evaluation in duplicate fed-batch shake flask suspension cultures in low serum-containing medium (containing BSA and added 1% dFCS). Product concentrations at harvest were determined by protein A high performance liquid chromatography (HPLC), according to well-known standard methods. Based on this one of the cell lines was discarded. The resulting 9 cell lines all produced 11B8 antibody (denoted "11B8T") in good yields in the range of from 354-771 mg/L as determined by protein A HPLC.

Example 4

Comparison of Hybridoma-derived 2F2 and Transfectoma-derived Recombinant 2F2T By use of gel electrophoresis (SDS-PAGE and native agarose gel electrophoresis) it was shown that 2F2 and 2F2T are of the same size, and only slightly differ in electric charge.

Furthermore, 2F2 and 2F2T bind to CD20-transfected NS/0 cells and Raji cells with similar affinity as measured by flow cytometry using FACScalibur™ (Becton Dickinson, San Diego, Calif., USA). No binding to non-transfected NS/0 cells was observed demonstrating the specificity of 2F2 and 2F2T. 2F2 and 2F2T also induce CDC in a concentration-dependent manner to the same extent in ARH-77 cells (IgG plasma cell leukemia), Daudi cells, DOHH cells (refractory immunoblastic B cell lymphoma progressed from follicular centroblastic/centrolytic lymphoma, DSMZ, Braunschweig, Germany) and Raji cells, measuring cell lysis (number of PI-positive cells) by flow cytometry (FACScalibur). In a second experiment, the concentrations of 2F2 and 2F2T were kept constant while serum was added in different concentrations. No significant differences between 2F2 and 2F2T were observed.

Finally, 2F2 and 2F2T bound to cell-associated CD20 binds complement factor C1q strongly and to the same extent. The experiment was performed in Daudi cells, DOHH cells, and Raji cells using fluorescein-conjugated anti-C1q polyclonal antibodies for detecting binding of C1q.

Example 5

Binding Characteristics of Human Antibodies Against CD20

Figure 4:
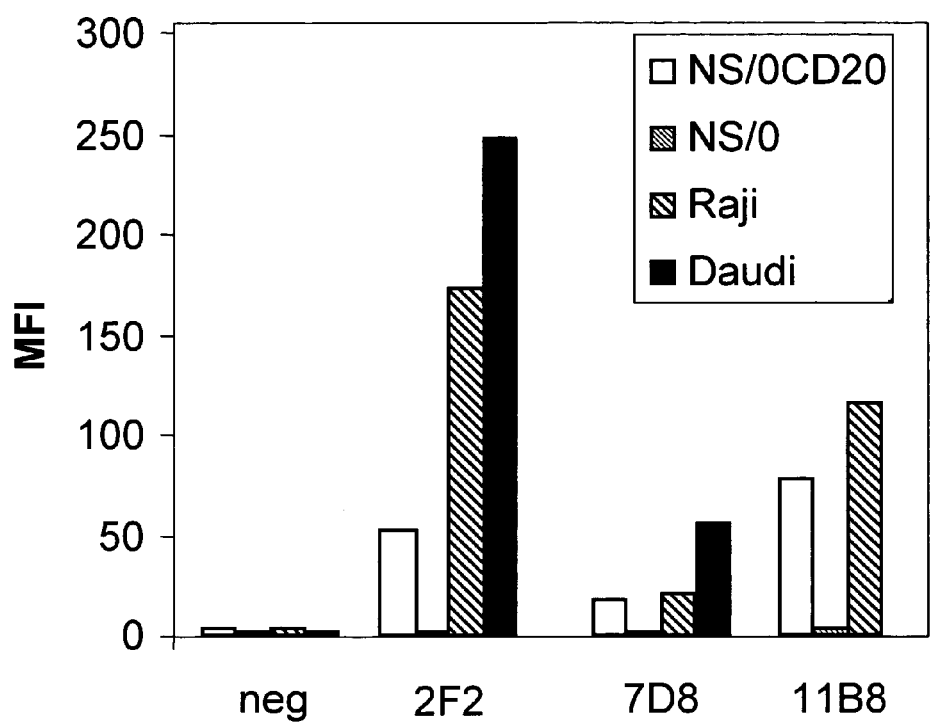
FIG. 4 is a graph comparing the binding of human monoclonal antibodies 2F2, 7D8, and 11B8 to Raji, Daudi, and CD20 transfected NS/0 cells and parental NS/0 cells using flow cytometry.

Binding to different cell lines: NS/0, NS/0 transfected with human CD20, Daudi and Raji cells were incubated for 30 min at 4° C. with culture supernatant containing human antibodies 2F2, 7D8, and 11B8 followed by incubation with FITC-conjugated anti-human IgG Ab. Binding was assessed by flow cytometry using a FACScalibur flow cytometer. Fluorescence intensities were compared with negative control isotype matched samples. As shown in FIG. 4, all three antibodies bound to NS/0 cells transfected with human CD20, whereas no binding was observed to parental, non-transfected NS/0 cells. All three antibodies also bound to the two different Burkitt lymphoma B cell lines (Raji and Daudi) indicating that 2F2, 7D8, and 11B8 are CD20 specific. Supernatant containing 7D8 or 11B8 were tested under non-saturating conditions, therefore, lower mean fluorescence intensities compared to 2F2 are observed.

Figure 5A:
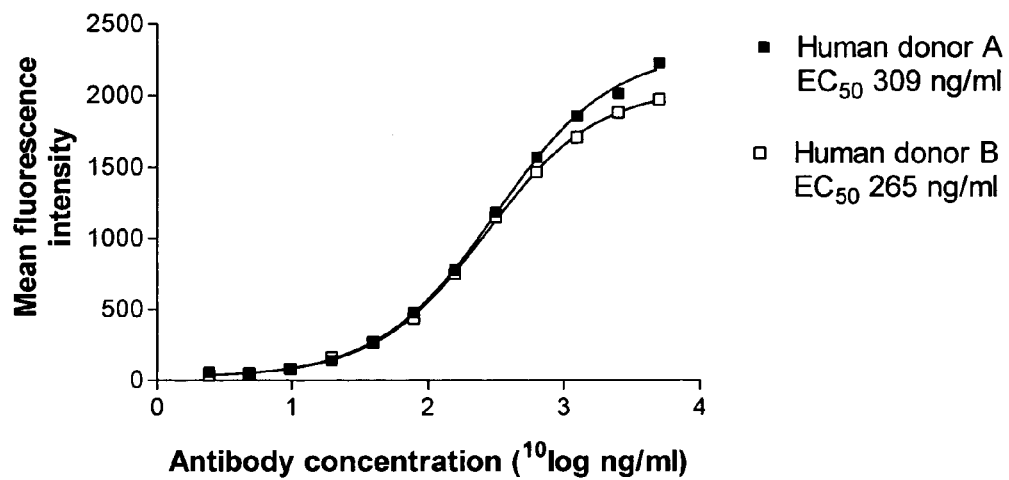
FIGS. 5A and 5B show the binding of 2F2 to PBMCs from three human donors using flow cytometry.
Figure 5B:
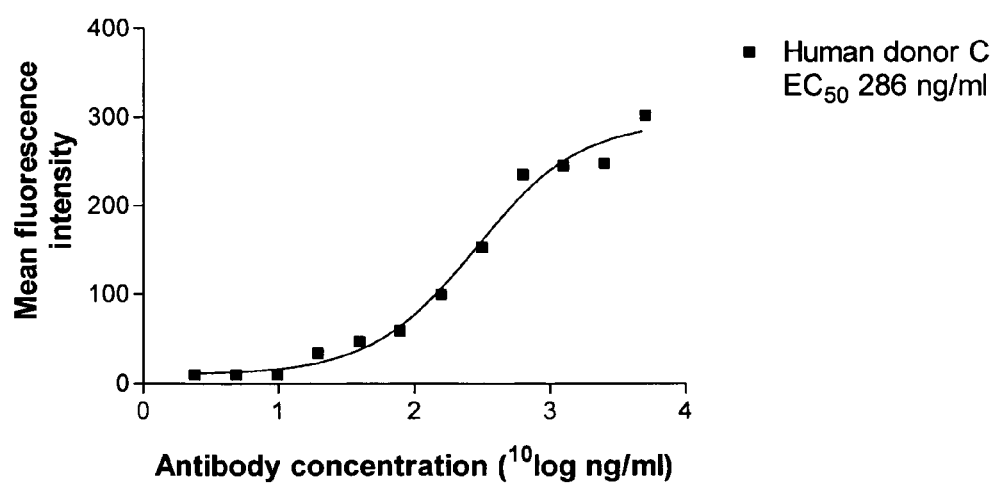
Figure 6:
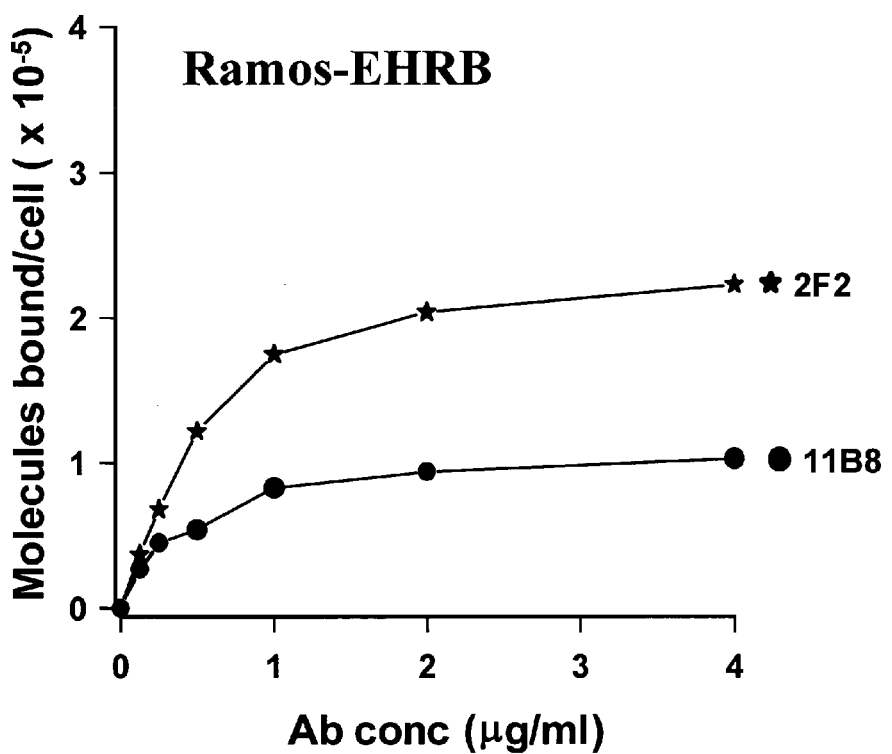
FIG. 6 is a graph comparing the binding affinity of $^{125}$I-labeled 2F2 and $^{125}$I-labeled 11B8 to Ramos-EHRB cells.

$EC_{50}$ value of 2F2 as determined by flow cytometry: In order to determine the apparent affinity of 2F2 for CD20 expressed on human B cells, a binding curve was made of 2F2 using isolated PBMCs from three human donors and gating of CD3-negative cells. The isolated PBMCs were incubated for 1 hour with a concentration range of FITC labeled 2F2 and analysed on FACS, and the mean fluorescence intensity (MFI) determined. The MFI values are shown in FIGS. 5A and 5B as a function of the antibody concentration. The $EC_{50}$ values were calculated by use of Graph Pad Prism 3.02 by non-linear regression. The $EC_{50}$ value of 2F2 in humans was similar for all three donors with a mean (±s.e.m.) of 287±12.7 ng/ml (1.9±0.1 nM).

Binding of $^{125}$I-labeled mAbs to CD20 expressing cells: mAbs were iodinated using Iodobeads (Pierce Chemical Co., Rockford, Ill.). $^{125}$I-labelled mAbs were serially diluted and incubated with Ramos-EHRB (cells for 2 hours at 37° C. in the presence of sodium azide and 2-deoxyglucose to prevent endocytosis. The cell bound and free $^{125}$I labeled mAbs were then separated by centrifugation at 14,000×g for 2 min through a mixture of phthalate oils, allowing rapid separation without disturbing the binding equilibrium. The pelleted cells together with bound antibody were then counted using a gamma counter (Wallac UK Ltd, Milton Keynes, UK).

Figure 7A:
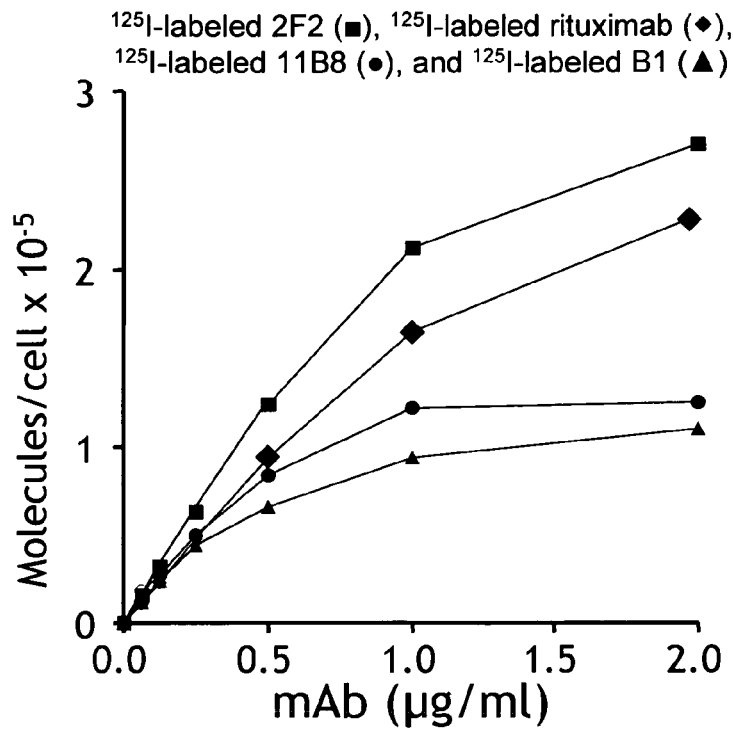
FIGS. 7A and 7B show the binding of $^{125}$I-labeled 2F2 and $^{125}$I-labeled 11B8 compared to $^{125}$I-labeled rituximab (chimeric anti-CD20 antibody, IDEC) and $^{125}$I-labeled B1 (the term B1 corresponds to the unlabeled form of Bexxar™, which is a $^{131}$I-labeled murine anti-human CD20 antibody, Coulter) to Ramos-EHRB cells (A) and Daudi cells (B).
Figure 7B:
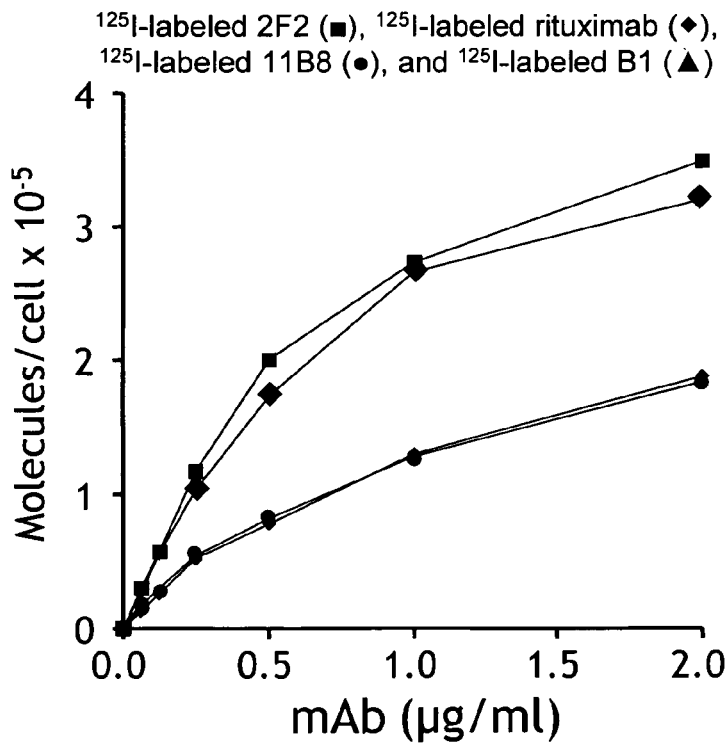

As shown in FIG. 6, 2F2 and 11B8 exhibit similar $K_D$ (or similar saturation points) indicating that both antibodies bind with similar affinity. However, 11B8 saturates at a lower level than 2F2 indicating that it recognized a different form of CD20. This is also in agreement with a further experiment showing that a similar number of 2F2 and rituximab antibody molecules binds to CD20 on Ramos-EHRB cells and Daudi cells, as shown by the similar levels of binding saturation (approximately $2-3 \times 10^5$ antibody molecules per cell). 11B8 and B1, in contrast, saturate at half this level and only about $1-2 \times 10^5$ antibody molecules bind to the Ramos-EHRB cells (FIG. 7A) and Daudi cells (FIG. 7B).

To exclude the possibility that the iodinated antibodies bind via Fc-receptors, binding curves were confirmed by use of anti-CD20 $F(ab')_2$ fragments. Again, similar numbers of 2F2 and rituximab-$F(ab')_2$ fragments bound to both Ramos-EHRB and Daudi cells. Also in these experiments, the number of 2F2 or rituximab antibody molecules bound to Ramos-EHRB cells and Daudi cells saturates at approximately twice the number of 11B8 and B1 molecules bound to the cells.

Figure 8:
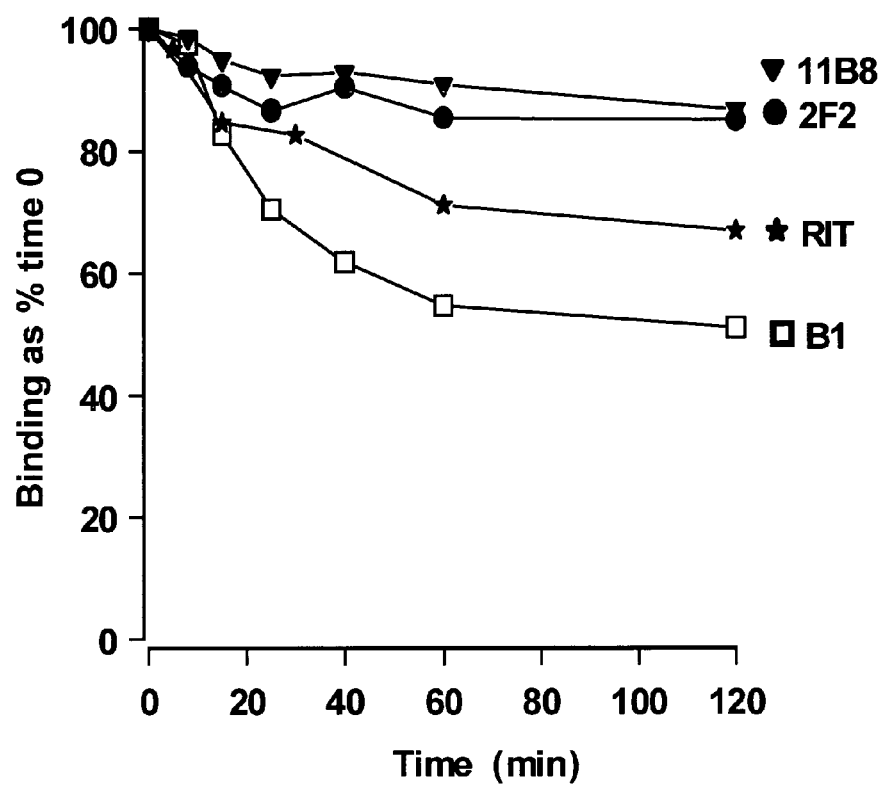
FIG. 8 is a graph comparing the dissociation rates of $^{125}$I-labeled 11B8T, $^{125}$I-labeled 2F2, $^{125}$I-labeled rituximab (RIT), and $^{125}$I-labeled B1.
Figure 9:
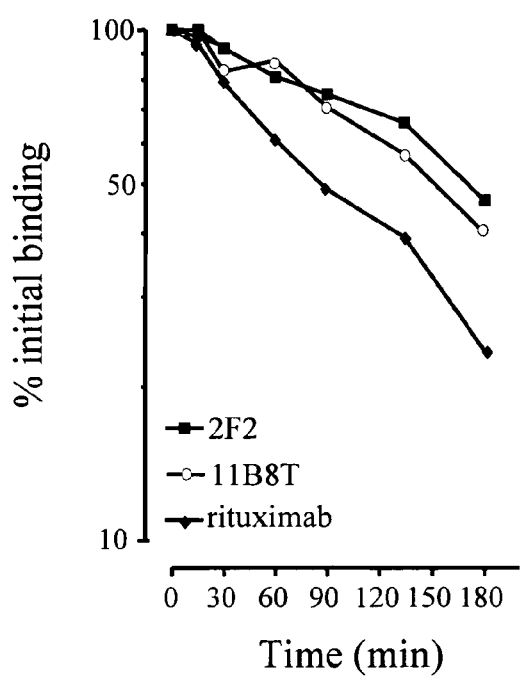
FIG. 9 shows the dissociation rates of the F(ab')$_2$ fragments of 2F2, 11B8T, and rituximab in Ramos-EHRB cells.

Dissociation rate: To determine the dissociation rate of the mAbs, Ramos-EHRB cells (final volume of 1 ml in the presence of azide/2DOG) were incubated for 2 hours at 37° C. with 2 µg/ml $^{125}$I mAbs to achieve maximum binding. Following centrifugation in a microfuge (2000 rpm for 2 min), the supernatant was removed, the pellet quickly resuspended in 1 ml medium, and immediately transferred to 9 ml medium at 37° C. in a 15 ml conical tube. At various times over the next 2 hours, 0.4 ml samples were removed and separated on phthalate oils to determine the level of radiolabeled mAbs remaining on the cell surface. As shown in FIG. 8, both 2F2 and 11B8 dissociated significantly more slowly from CD20 than rituximab or B1.

Dissociation rates of anti-CD20 $F(ab)_2$ fragments: Ramos-EHBR cells were saturated with 2 µg/ml of $^{125}$I-labeled $F(ab)_2$ fragments of 2F2, 11B8, and rituximab, respectively. The Ramos-EHBR cells were washed and incubated in the presence of a high concentration of the unlabeled antibody. The maximal (initial) binding to Ramos-EHRB cells was set at 100%. At several time points over the next 3 hours following loading, 0.4 ml samples were removed and separated on phthalate oil to determine the levels of radiolabeled mAb remaining on the cell surface. As can be seen from FIG. 9, 2F2 and 11B8 dissociated much more slowly from the surface of CD20 than rituximab. At 90 min, approximately 50% of the $F(ab)_2$ rituximab molecules were bound to the cell, whereas half of the $F(ab)_2$ 2F2 molecules were dissociated after 3 hours. The $k_d$ ($k_{off}$) values for 2F2, 11B8T, and rituximab are calculated as follows:

$$F(ab)_2 2F2: k_d = \ln 2 / t_{1/2}(\sec) = \ln 2/10800(\sec) = 6.4 \times 10^{-5} \sec^{-1}$$

Figure 10A:
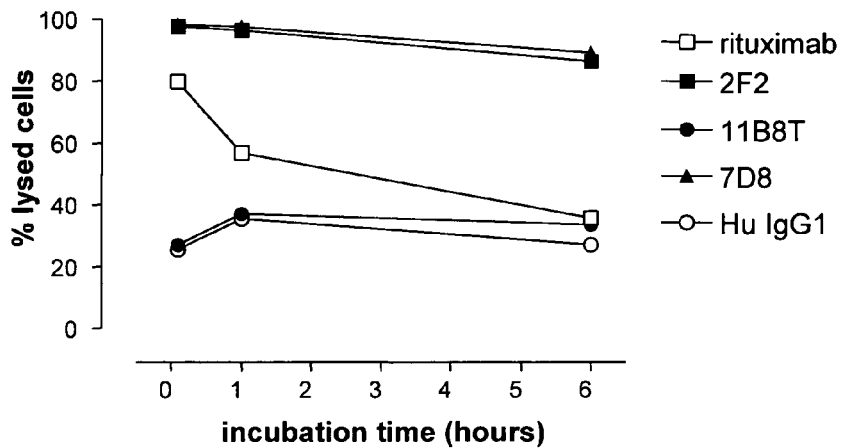
FIGS. 10A and 10B show the CDC by 2F2T, 11B8T, 7D8, rituximab, and an isotype control antibody (HuMab-KLH) of Daudi cells (A) and SU-DHL-4 cells (B) at different time points (functional off-rate) using flow cytometry.
Figure 10B:
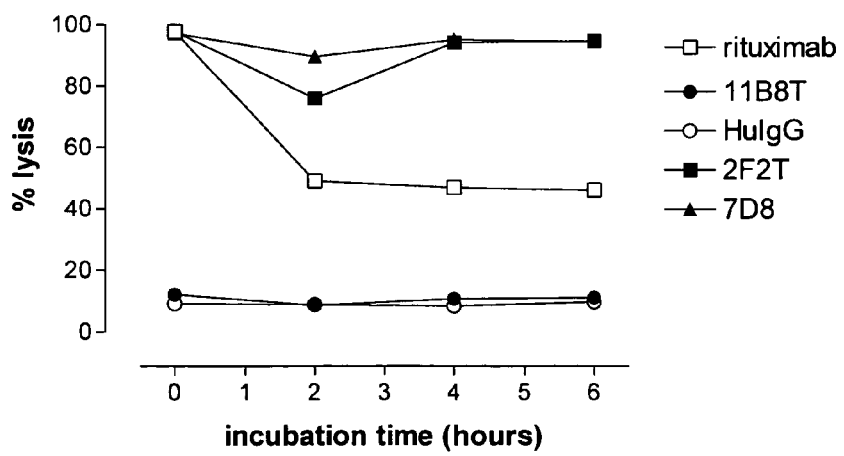

$F(ab)_2 11B8T$: $k_d$=ln 2/$t_{1/2}$(sec)=ln 2/9000(sec)=7.7× $10^{-5}$ sec$^{-1}$ $F(ab)_2$rituximab: $k_d$=ln 2/$t_{1/2}$(sec)=ln 2/5400(sec) =1.3×$10^{-4}$ sec$^{-1}$ Anti-CD20 mAb functional off rates: The impact of the slow 2F2 dissociation rate compared to rituximab was assessed in a functional CDC assay. To this end, Daudi or SU-DHL4 cells were pre-incubated with 10 µg/ml anti-CD20 mAb or an isotype control antibody, washed and incubated in medium for different time points. At these time points after start of the assay, samples were incubated with complement (normal human serum 20 vol/vol %) and then incubated for another 45 min at 37° C. Thereafter, cell lysis was determined on FACS by using PI (propidium iodide) staining method. The % lysed cells (PI-positive cells) are shown in FIG. 10A (Daudi cells) or FIG. 10B (SU-DHL4 cells) as a function of incubation time. 2F2 induced high CDC in both cell lines, and still lysed up to 90% of the cells after 6 hours, indicating that the CD20 saturation of the cells remained sufficiently high to induce complement-mediated lysis of most of the cells. Rituximab, in contrast and in agreement with the above dissociation rate studies, dissociated rapidly from the cells and failed to induce specific lysis following the 6 hour incubation period. 11B8 was used as a control and did not induce CDC.

Example 6

CDC of Human Antibodies Against CD20

Serum preparation: Serum for complement lysis was prepared by drawing blood from healthy volunteers into autosep gel and clot activator vacutainer tubes (BD biosciences, Rutherford, N.J.) which were held at room temperature for 30-60 min and then centrifuged at 3000 rpm for 5 min. Serum was harvested and stored at −80° C.

Flow cytometry: For flow cytometry a FACScalibur flow cytometer was used with CellQuest pro software (BD Biosciences, Mountain view, Calif.). At least 5000 events were collected for analysis with cell debris excluded by adjustment of the forward sideward scatter (FCS) threshold.

Figure 11A:
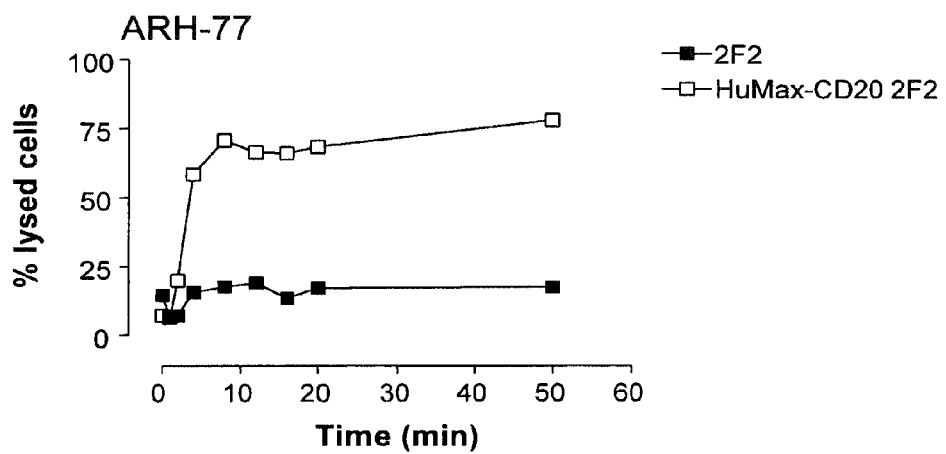
FIGS. 11A-E show the kinetics of CDC induced by 2F2 and rituximab in different cell lines using flow cytometry.
Figure 11B:
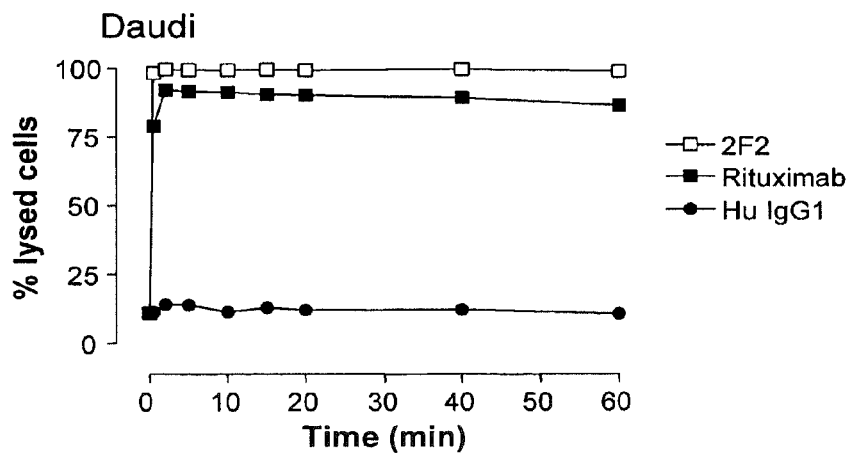
Figure 11C:
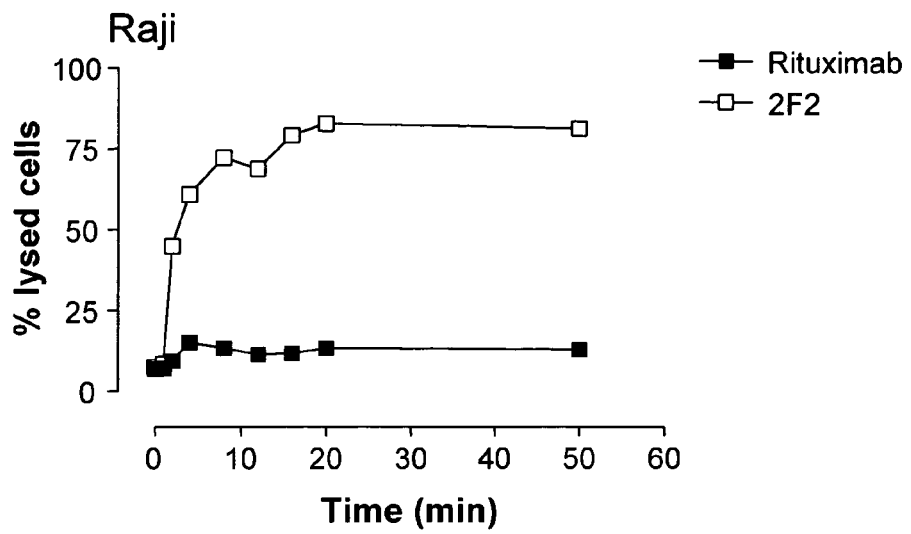
Figure 11D:
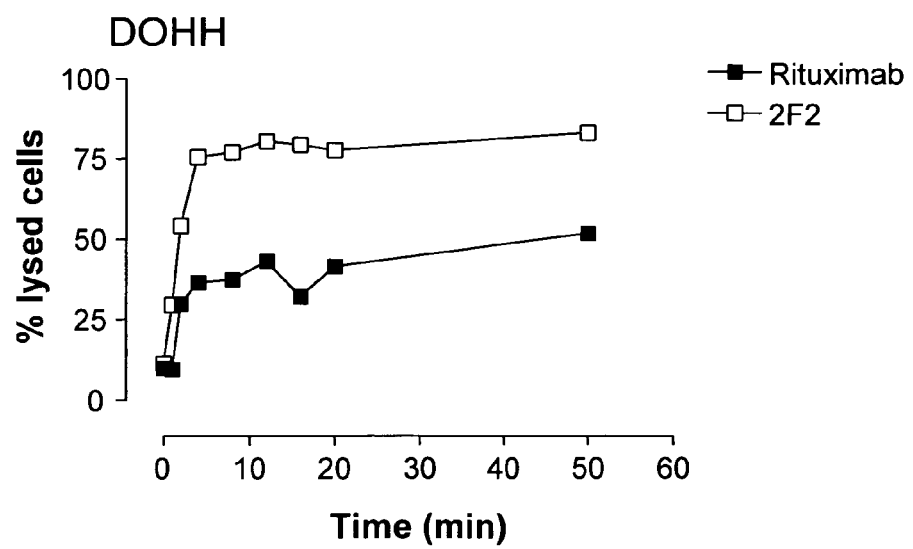
Figure 11E:
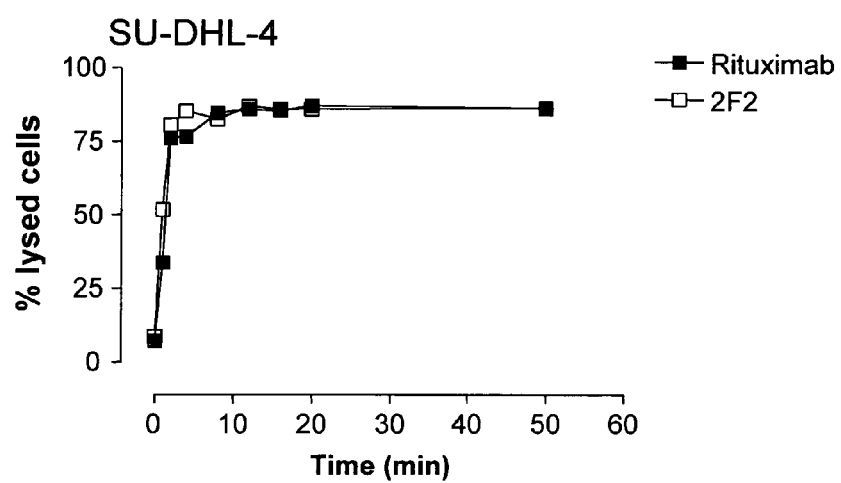

CDC kinetics: In a first set of experiments (n=3) the kinetics of CDC of five different B-cell lines, i.e., Daudi, SU-DHL-4, Raji, DOHH and ARH-77, were determined by adding 10 µg/ml 2F2, rituximab and an IgG control antibody, respectively, for 10 min before human serum was added. At several time intervals (up to one hour) after induction of CDC, the cells were suspended in PI solution and cell lysis (number of PI-positive cells) was measured by flow cytometry. The results are depicted in FIGS. 11A (ARH-77 cells), 11B (Daudi cells), 11C (Raji cells), 11D (DOHH) and 11E (SU-DHL-4). As seen, addition of antibodies induced cell lysis within 5 min. Interestingly, addition of 2F2 resulted in a marked cell lysis of more than 80% in all five B-cell lines. Rituximab induced more than 80% cell lysis only in the SU-DHL-4 and Daudi cell lines, whereas the cell lysis of the DOHH cell line was ~50%, and less than 20% in the ARH-77 and Raji cell lines. No lysis was observed with the IgG control antibody (data only shown in FIG. 11B).

Figure 12A:
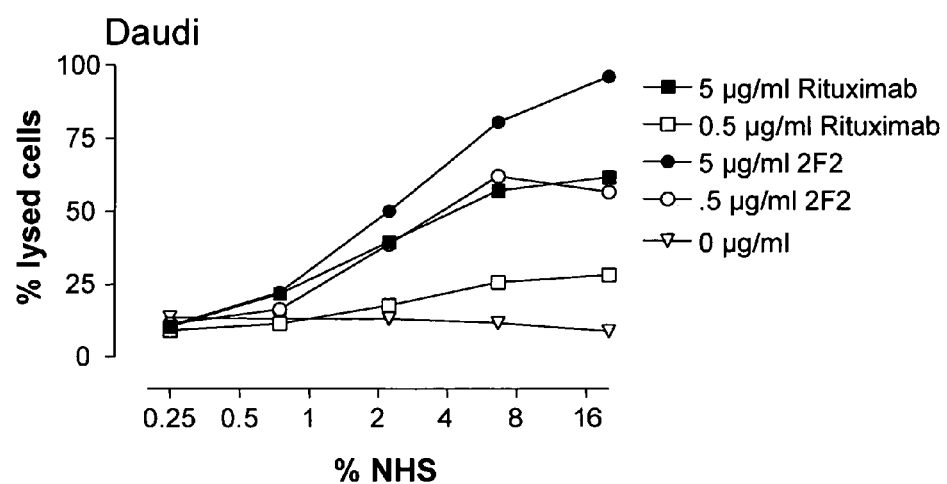
FIGS. 12A-D show CDC induced by 2F2 and rituximab in different cell lines as a function of the concentration of complement (normal human serum (NHS)) at two different antibody concentrations using flow cytometry.
Figure 12B:
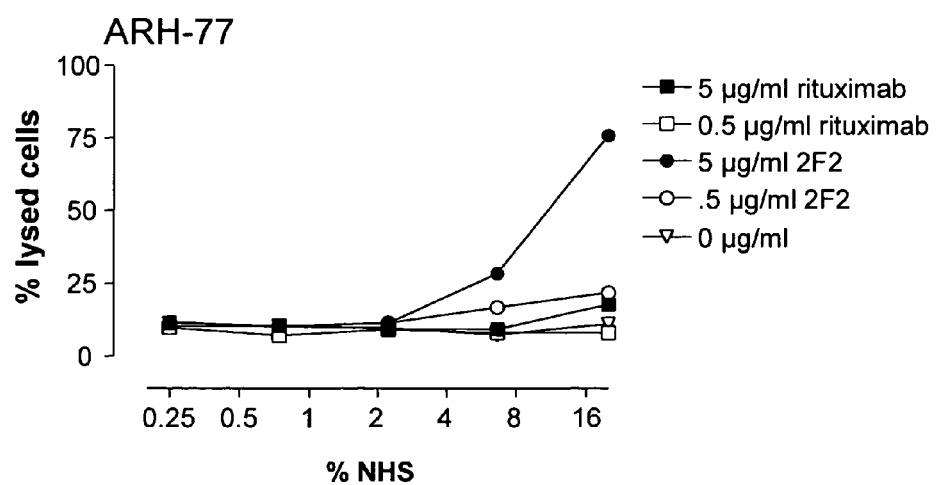
Figure 12C:
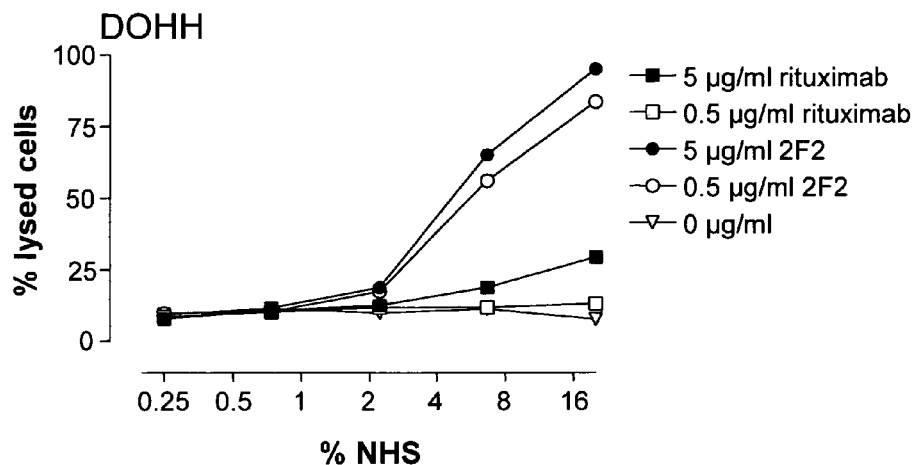
Figure 12D:
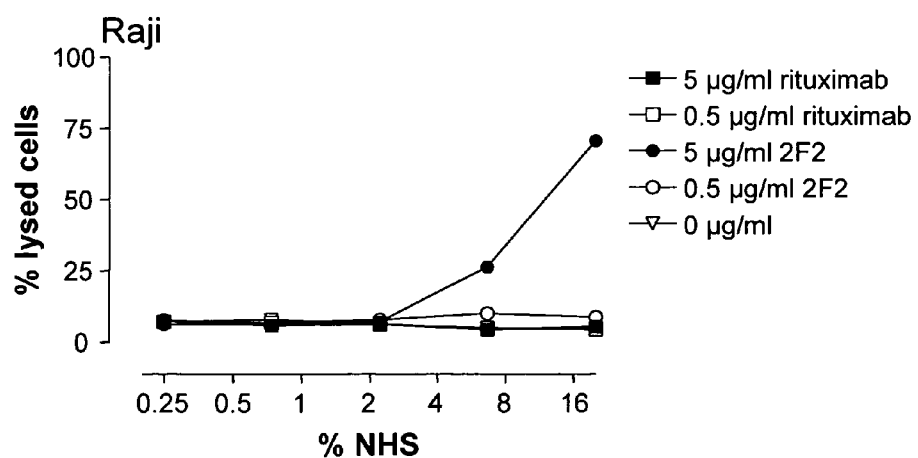

CDC serum titration: In a separate set of experiments (n=5), NHS (normal human serum) was titrated at two different antibody concentrations of 0.5 µg/ml and 5 µg/ml. Cells were pre-incubated with 2F2 or rituximab for 10 min, before a concentration range of NHS was added. At 45 min after induction of CDC, cells were resuspended in PI solution. Cell lysis (number of PI-positive cells) was measured by flow cytometry. FIGS. 12A-D show the percentage of lysed (PI-positive) cells as a function of NHS concentration. FIG. 12A shows cell lysis of Daudi cells, FIG. 12B cell lysis of ARH-77 cells, FIG. 12C cell lysis of DOHH cells, and FIG. 12D cell lysis of Raji cells. Increased lysis of cells was observed with increased NHS concentration. Addition of 2F2 caused maximal lysis of Daudi cells at the highest NHS and antibody concentration. Rituximab induced about 50% cell lysis of Daudi cells at the highest NHS concentration.

In ARH-77 cells, only the highest concentration of NHS and 2F2 led to approximately 75% cell lysis. Lower antibody concentrations were insufficient to induce ARH-77 cell lysis. Rituximab was not able to induce cell lysis of ARH-77 cells in this experiment.

2F2 was able to induce NHS-concentration dependent cell lysis of DOHH cells at both the high and the low concentration, whereas rituximab was not able to induce lysis under these conditions.

Finally, 2F2 induced NHS-concentration-dependent lysis of Raji cells, which was only apparent by use of 5 µg/ml mAb. No lysis was observed with rituximab.

In these experiments, no lysis was observed with the isotype control antibody (data not shown).

Figure 13A:
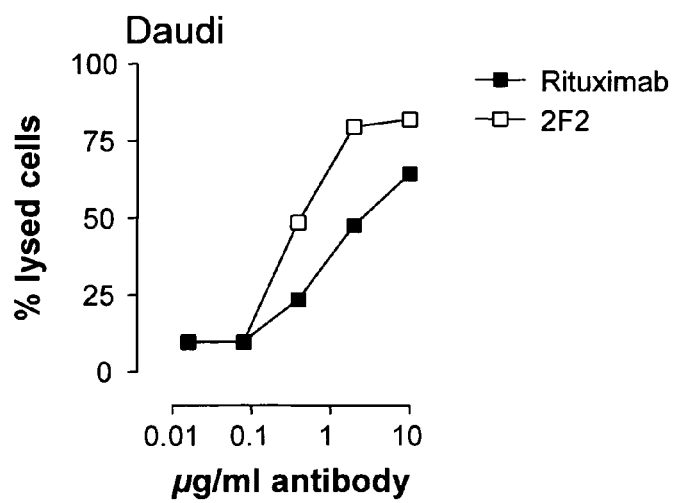
FIGS. 13A-D show concentration-dependent induction of CDC by 2F2 and rituximab in different cell lines using flow cytometry.
Figure 13B:
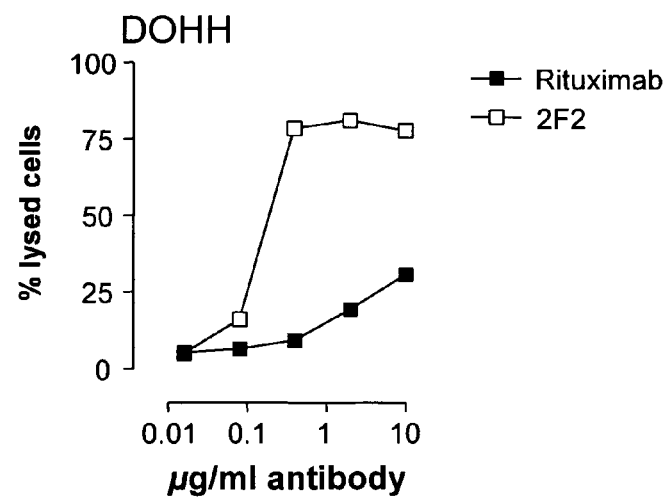
Figure 13C:
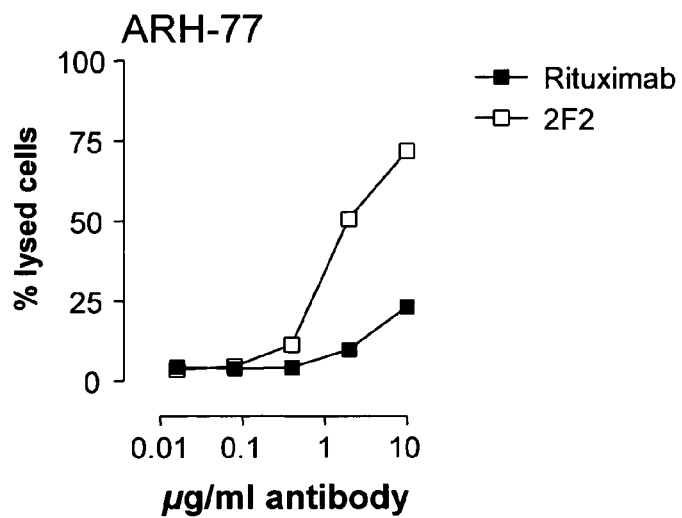

CDC antibody titration: To measure the ability of the anti-CD20 antibodies to induce CDC at low concentrations, an experiment was performed where the antibodies were titrated (n=6). Various cell lines were pre-incubated with a concentration range of 2F2 and rituximab, respectively, for 10 min before NHS was added. After 45 min incubation at 37° C. (when maximal lysis occurs) the cells were resuspended in PI solution and cell lysis (number of PI-positive cells) was measured by flow cytometry. FIGS. 13A (Daudi cells), 13B (DOHH cells), 13C (ARH-77 cells), and 13D (Raji cells) show the percentage of lysed (PI-positive) cells as a function of antibody concentration. Both 2F2 and rituximab induced a concentration-dependent increase in cell lysis. 2F2 induced more than 80% lysis of Daudi cells upon addition of 2 µg/ml, whereas with rituximab this level was not reached even after addition of 10 µg/ml. Furthermore, 2F2 induced more than 80% lysis of DOHH cells at 0.4 µg/ml, whereas minimal lysis was observed with rituximab at this concentration. The maximal lysis of DOHH cells with rituximab (~30% of total cell analyzed) was reached at 10 µg/ml. Induction of lysis of ARH-77 and Raji cells by 2F2 was lower, but still ~70% lysis was reached at an antibody concentration of 10 µg/ml. At its highest concentration, rituximab induced lysis in only ~23% of ARH-77 cells, and in only ~6% of Raji cells.

Figure 14A:
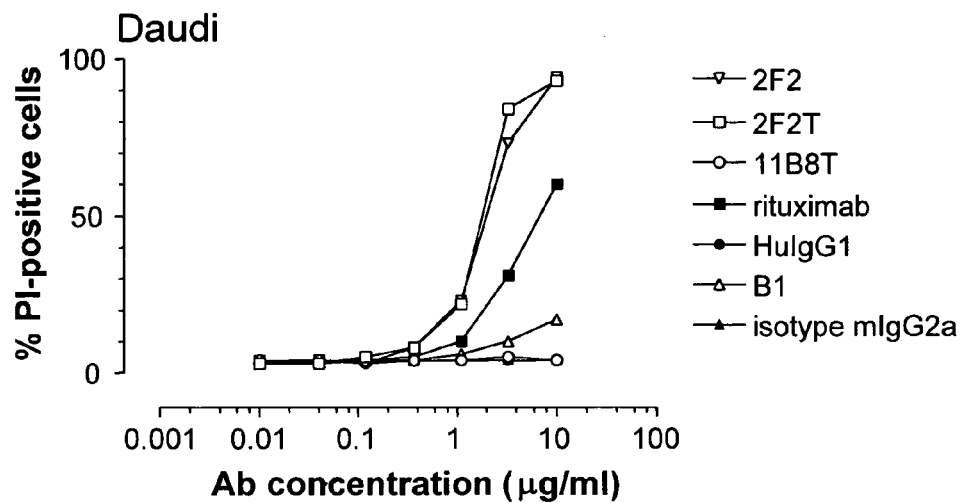
FIGS. 14A and 14B show concentration-dependent induction of CDC by 2F2, 2F2T, 11B8T, B1, and rituximab in Daudi cells (A) and Raji cells (B).
Figure 14B:
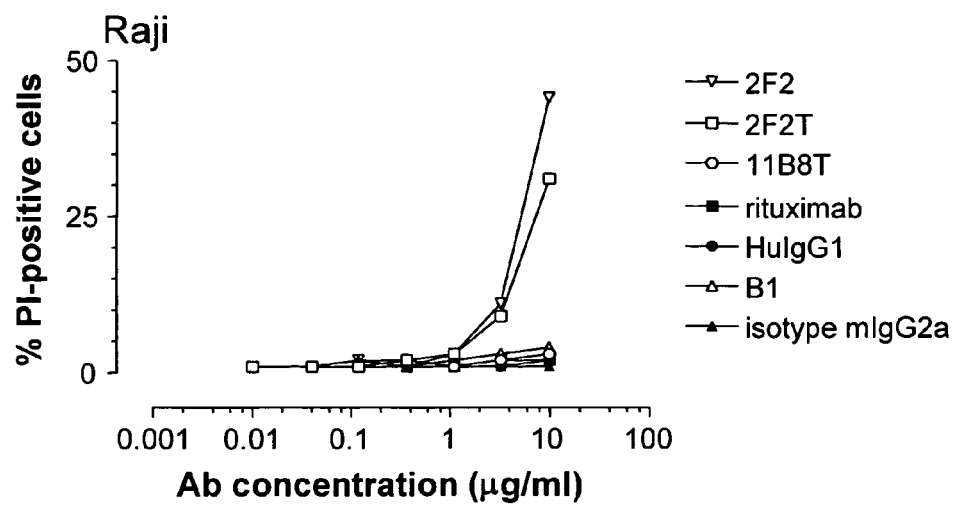

In a similar experiment, 2F2, 2F2T, 11B8T, and rituximab were investigated for their ability to induce CDC of Daudi and Raji cell lines, see FIGS. 14A and 14B. Also in this experiment more than 80% lysis of Daudi cells was observed with (transfectoma-derived) 2F2T at 10 µg/ml, whereas rituximab reached only to 60% lysis even at 10 µg/ml, cf. FIG. 14A. Lysis of Daudi cells with 2F2T was identical to the lysis obtained with hybridoma-derived 2F2.

Figure 13D:
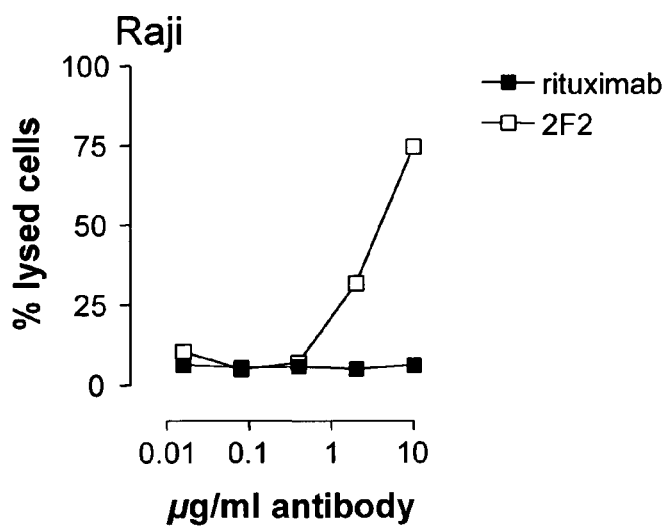

Lysis of Raji cells was more difficult, but again both 2F2 and 2F2T induced lysis of Raji cells to a similar extent (FIG. 14B). Rituximab was not able to induce CDC of Raji cells which is in agreement with the experiment shown in FIG. 13D.

As can be seen from FIGS. 14A and 14B neither Daudi nor Raji cells were susceptible to CDC by 11B8T. B1 induced lysis of Daudi cells, but only to a small extent, and was not able to induce lysis of Raji cells.

CDC activity of anti-CD20 in Daudi cells: To determine the CDC activity of each antibody, elevated membrane permeability was assessed using FACS analysis of propidium iodide (PI)-stained cells. Briefly, the Daudi cells were washed and resuspended in RPMI/1% BSA at $1\times10^6$ cells/ml. Various concentrations of human monoclonal antibodies were added to the Daudi cells and allowed to bind to CD20 on the cells for 10-15 min at room temperature. Thereafter, serum as a source of complement was added to a final concentration of 20% (v/v) and the mixtures were incubated for 45 min at 37° C. The cells were then kept at 4° C. until analysis. Each sample (150 µl) was then added to 10 µl of PI solution (10 µg/ml in PBS) in a FACS tube. The mixture was assessed immediately by flow cytometry. As shown in FIG. 15A, 2F2 and 7D8 showed superior CDC activity compared to rituximab.

Figure 15A:
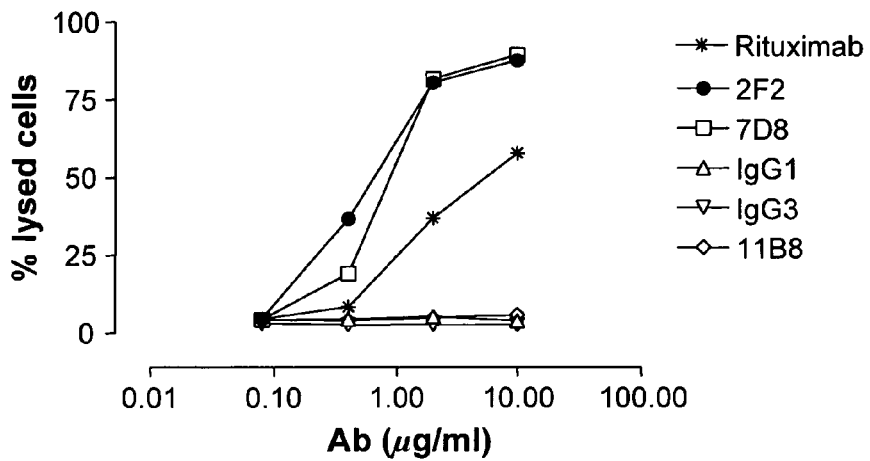
FIGS. 15A and 15B are graphs comparing CDC of Daudi cells (cells expressing low levels of CD55/59) by human monoclonal antibodies 2F2, 7D8, and 11B8 and rituximab; (A) shows percent lysis of unwashed cells and (B) shows percent lysis of cells which were washed before the addition of serum.
Figure 15B:
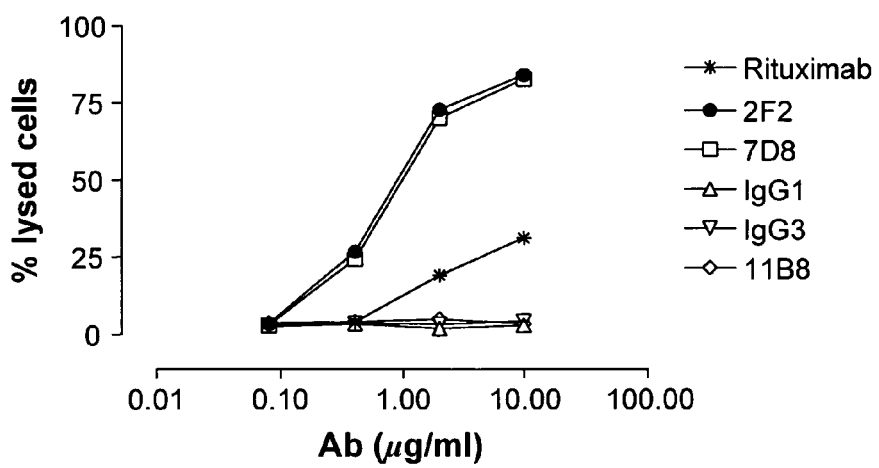

In a second experiment, cells were labeled with human monoclonal antibodies as above, then washed and incubated in PBS for 45 min at 37° C. prior to the addition of human serum. This ensured that only antibody bound to the cell at the time of serum addition was available to activate complement for cell lysis. As shown in FIG. 15B, decreased CDC activity was found for rituximab compared to 2F2 and 7D8 indicating that the human anti-bodies (2F2 and 7D8) are not affected by washing the cells prior to the addition of serum.

Figure 16A:
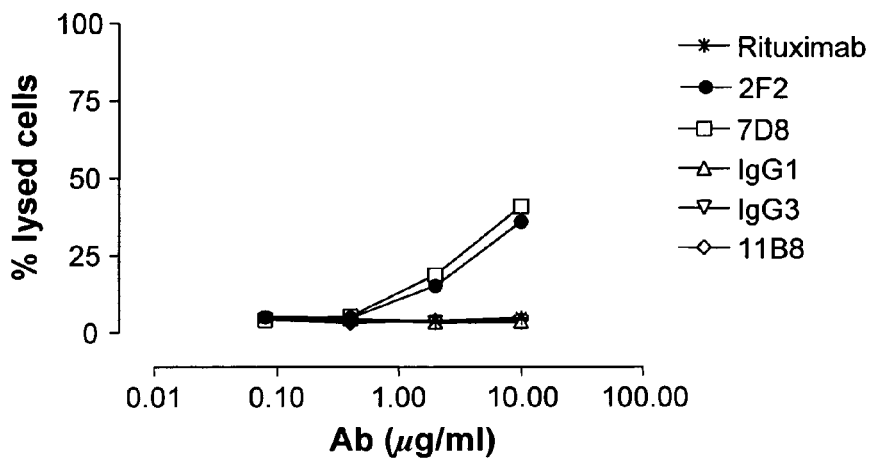
FIGS. 16A and 16B are graphs comparing CDC of Raji cells (cells expressing high levels of CD55/59) by human monoclonal antibodies 2F2, 7D8, and 11B8 and rituximab; (A) shows percent lysis of cells not blocked with anti-CD55 and anti-CD59 antibodies, and (B) shows percent lysis of cells blocked with anti-CD55 and anti-CD59 antibodies.

CDC activity of anti-CD20 in Raji cells: CDC activity was assessed using Raji cells which have relatively high surface expression of CD55 and CD59 and, therefore, are more resistant to complement attack. Human antibodies were added to Raji cells and allowed to bind for 15 min. Human serum (20%) was added and the mixtures incubated for 45 min at 37° C. As shown in FIG. 16A, rituximab was ineffective in mediating CDC of Raji cells whereas significant levels of cell lysis occurred in Raji cells opsonized with 2F2 or 7D8. Accordingly, 2F2 and 7D8 have a unique capacity to lyse CD55/59 positive target cells.

Figure 16B:
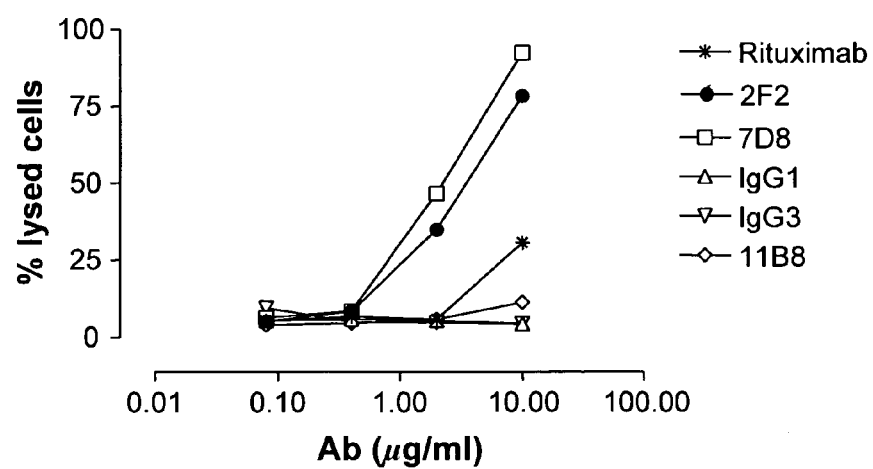

In a separate experiment, Raji cells were pre-incubated with saturating concentrations of anti-CD55 mAb (final concentration of 5 µg/ml) and anti-CD59 mAb (final concentration of 5 µg/ml) to block the effects of these complement defense molecules. Human anti-CD20 antibodies were then added along with serum (20%) as above for 45 min at 37° C. As shown in FIG. 16B, the blockade of CD55 and CD59 molecules resulted in almost 100% lysis of Raji cells with human antibodies 2F2 or 7D8 whereas only a 25% increase in cell lysis was observed using rituximab.

Role of complement inhibitors I—Expression of surface molecules: Since complement inhibitors such as CD55 and CD59 appear to play an important role in susceptibility to rituximab-induced CDC, an experiment was performed to determine the expression of these molecules on the B-cell lines under investigation (Raji, Daudi, DOHH, ARH-77, and SU-DHL-4).

The cells were stained with FITC-conjugated anti-CD55, anti-CD59 and anti-CD20 antibodies and molecules expression was analyzed by flow cytometry. The results are shown in the below Table 1.

TABLE 1

| Expression | CD20 | CD55 | CD59 |
|---|---|---|---|
| ARH-77 | ++ | ++++ | ++ |
| Raji | + | ++ | +++ |
| DOHH | ++ | +++ | ++ |
| SU-DHL-4 | +++ | + | ++ |
| Daudi | ++ | + | + |

Figure 17A:
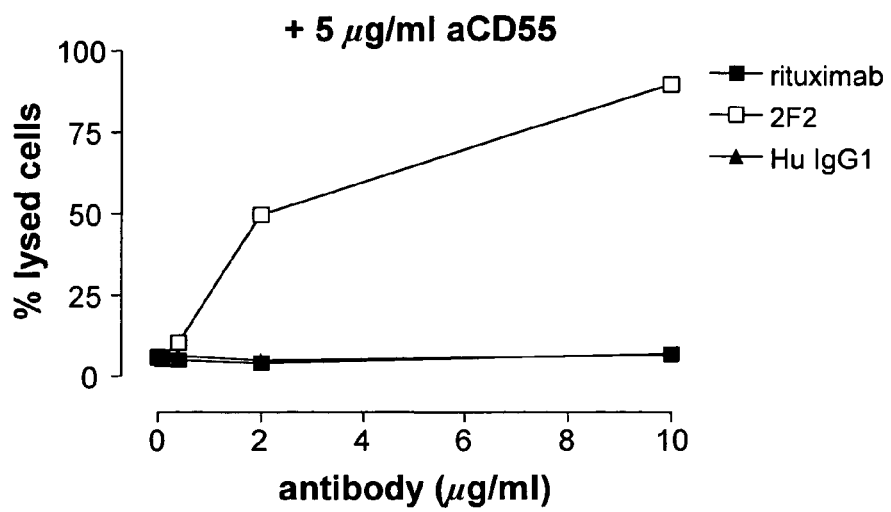
FIGS. 17A-C show the role of CD55 and CD59 in CDC induced by 2F2 and rituximab in Raji cells. (A) shows the percentage of lysed cells upon addition of anti-CD55 antibody, (B) shows the percentage of lysed cells upon addition of anti-CD59 anti-body, and (C) shows the percentage of lysed cells upon addition of both anti-CD55 anti-body and anti-CD59 antibody.
Figure 17B:
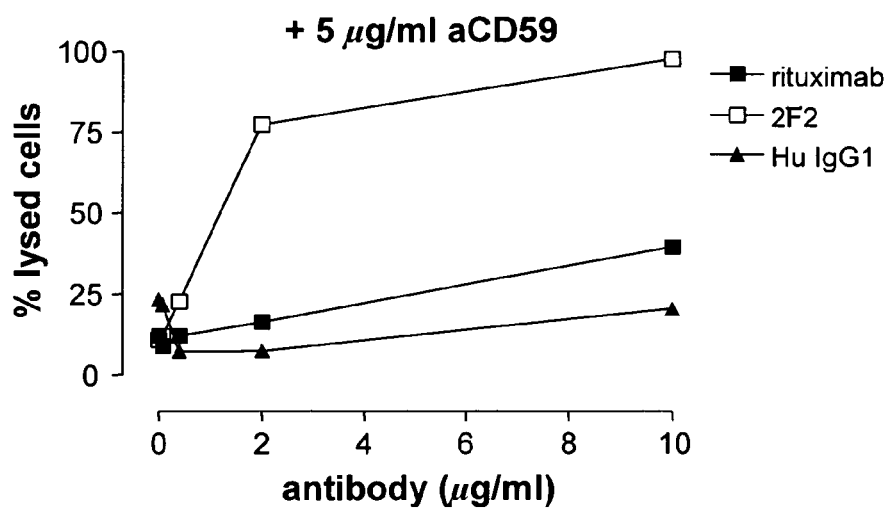
Figure 17C:
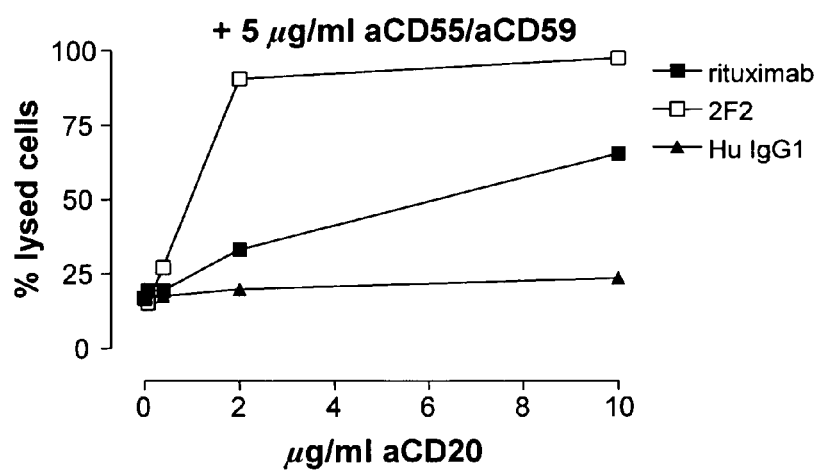

Role of complement inhibitors II—Blockade of CD55 and CD59: To further study the roles of CD55 and CD59 in anti-CD20-induced CDC, both complement inhibitor molecules were blocked by specific antibodies prior to induction of CDC (n=3). Raji cells were used because only partial lysis was induced by 2F2 alone. Raji cells ($1\times10^5$ cells/50 µl) were pre-incubated with a concentration range of 2F2 and rituximab together with anti-CD55 (5 µg/ml) or anti-CD59 (5 µg/ml) antibodies for 10 min, before pooled NHS (20%) was added. At 45 min after induction of CDC, cells were resuspended in PI solution. Cell lysis (number of PI-positive cells) was measured by flow cytometry. FIGS. 17A-C show the percentage of lysed (PI-positive) cells as a function of antibody concentration, and show one experiment which is exemplary of three experiments. FIG. 17A shows incubation of Raji cells with anti-CD55 antibody, FIG. 17B incubation of Raji cells with anti-CD59 antibody, and FIG. 17C incubation of Raji cells with anti-CD55 and anti-CD59 antibodies.

As can be seen in FIG. 17A, addition of anti-CD55 antibody did not influence 2F2 or rituximab-induced CDC. Addition of anti-CD59 antibody increased susceptibility of the cells to both 2F2 and to rituximab with ~30% (FIG. 17B). Addition of both anti-CD55 and anti-CD59 further enhanced anti-CD20-induced lysis of cells with ~30% (FIG. 17C).

Figure 18A:
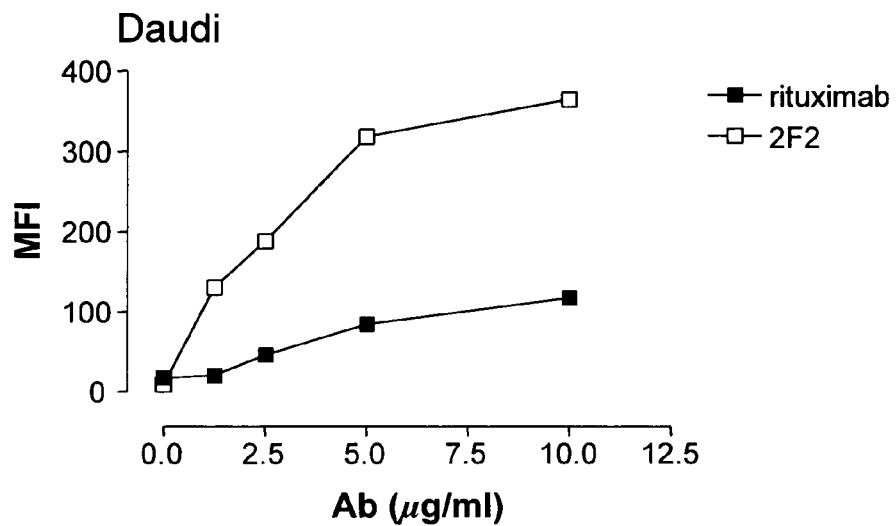
FIGS. 18A-D show the binding of complement factor C1q by 2F2 and rituximab in different cell lines as determined by flow cytometry.
Figure 18B:
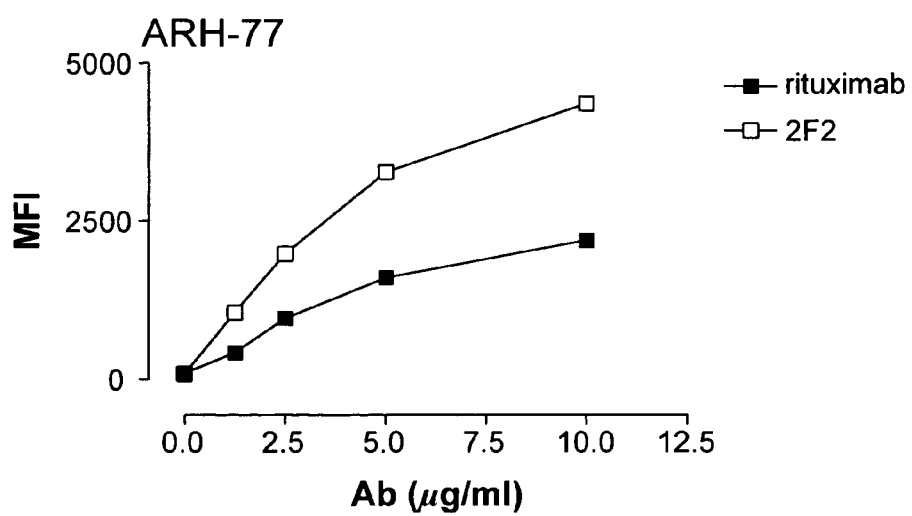
Figure 18C:
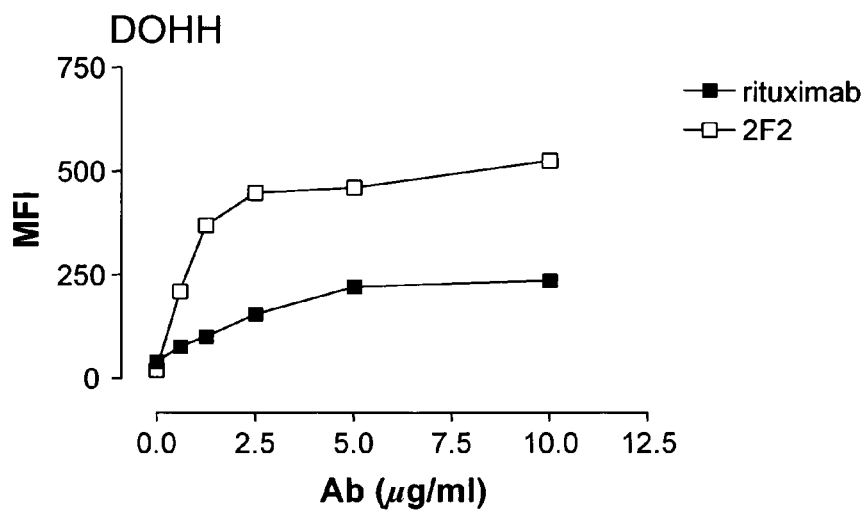
Figure 18D:
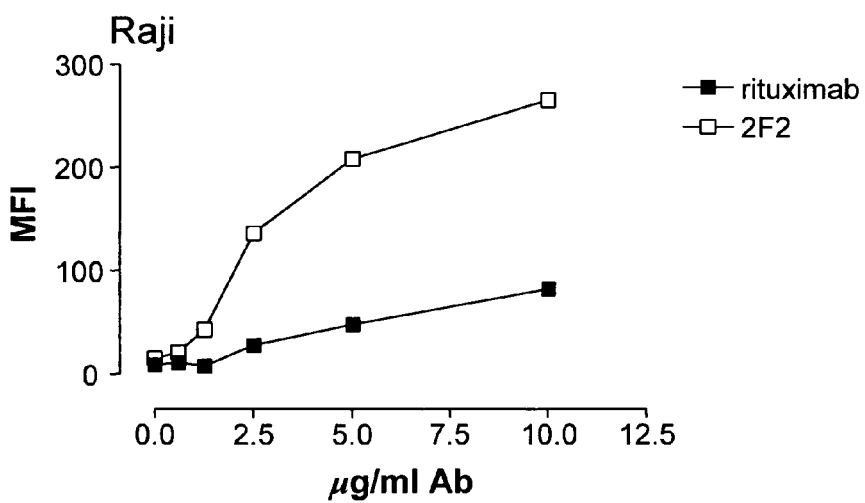

Role of complement factors, as determined by flow cytometry I—C1q binding: Anti-CD20 antibodies (2F2 and rituximab) and an isotype control antibody were added to various B-cell lines. After 10 min incubation, NHS (1 vol/vol %) was added. After further incubation for 10 min at 37° C. and washing of the cells, the supernatant was discarded and the cell pellet was incubated with FITC-conjugated anti-C1q antibody. Data show mean fluorescence intensity of cells stained with C1q and are depicted in FIGS. 18A (Daudi), 18B (ARH-77), 18C (DOHH), and 18D (Raji) (n=6). The results indicated antibody concentration-dependent increase in binding of C1q by 2F2, irrespective of the B-cell line investigated. Moreover, C1q binding by 2F2 was always higher than binding by rituximab, in all cell lines tested. No increase in mean fluorescence was observed with the isotype control antibody (data not shown).

Figure 19A:
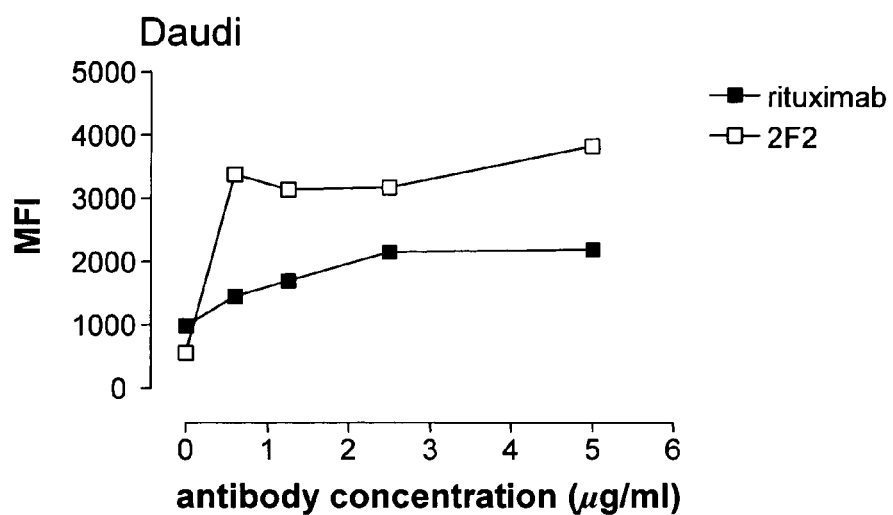
FIGS. 19A-D show the deposition of complement factor fragment C4c by 2F2 and rituximab in different cell lines as determined by flow cytometry.
Figure 19B:
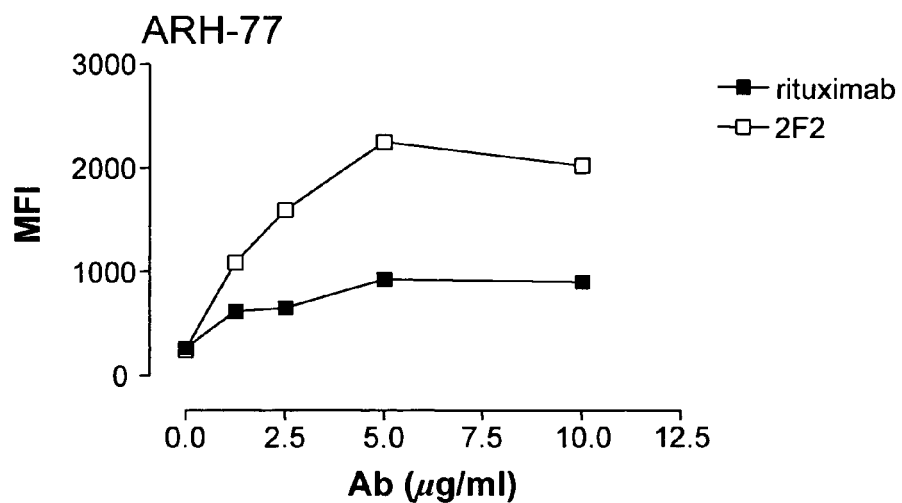
Figure 19C:
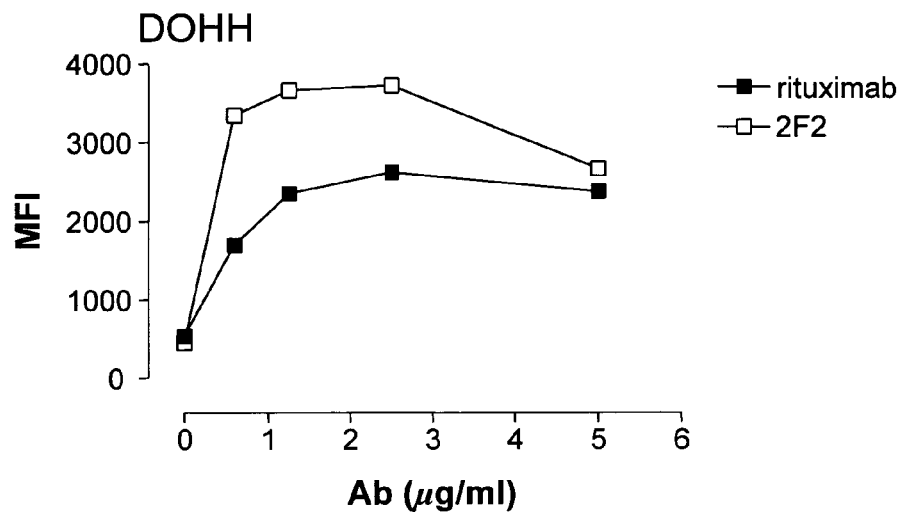
Figure 19D:
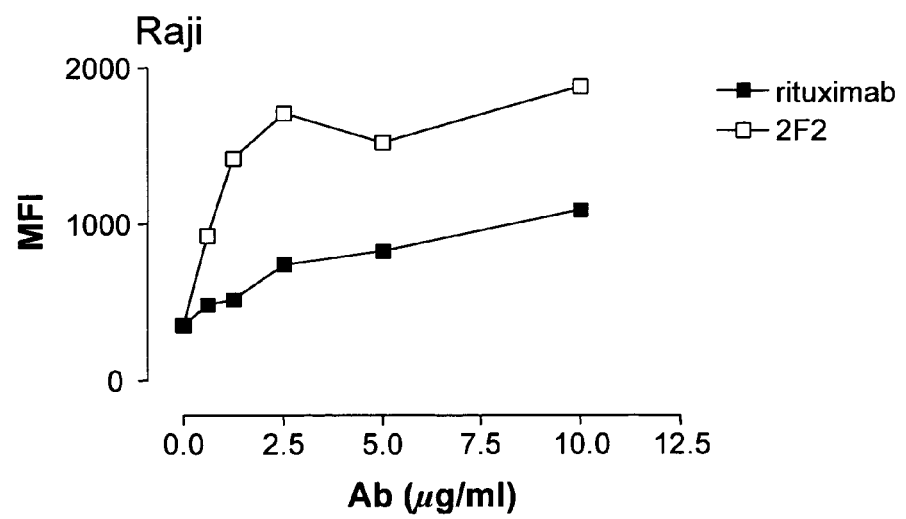

Role of complement factors, as determined by flow cytometry II—Complement activation via the classical route: Fixation of C4c to antibody-coated cells is an indication of activation of complement activation via the classical route. Anti-CD20 antibodies (2F2 and rituximab) and an isotype control antibody were added to various B-cell lines. After 10 min incubation at 37° C., NHS (1 vol/vol %) was added. After further incubation and washing of the cells, the supernatant was discarded and the cell pellet was incubated with FITC-conjugated anti-C4c antibody. Data show mean fluorescence intensity of cells stained with C4c and are depicted in FIGS. 19A (Daudi), 19B (ARH-77), 19C (DOHH), and 19D (Raji) (n=6). Complement factor C4c fixation to 2F2 was demonstrated in all B-cell lines tested (n=3), with a maximum reached at ~1 µg/ml of antibody. Fixation of C4c after 2F2 binding was much higher than after rituximab, irrespective of the cell line tested. No increase in mean fluorescence was observed with the isotype control antibody (data not shown).

CDC in heat-inactivated serum: Cells (Daudi cells, ARH-77 cells or Raji cells) and antibodies (rituximab, 2F2, 2F2T, 11B8, and isotype control antibody HuMab-KLH IgG1) were pre-incubated in a concentration range of anti-CD20 antibodies for 10 min, before NHS (active or heat-inactivated in a water bath at 57° C. at 30 min) was added. At 45 min after induction of CDC, cells were resuspended in PI solution. Cell lysis (number of PI-positive cells) was measured by flow cytometry. No lysis of the cells was observed in the presence of heat-inactivated serum, irrespective of the cell-line and CD20-antibody used, no CDC was observed in the presence of heat-inactivated serum.

Example 7

ADCC of Human Antibodies Against CD20 ADCC Assay I

Enrichment of human neutrophils: Polymorphonuclear cells (neutrophils, PMNs) were enriched from heparinized whole blood. Blood was diluted twice in RPMI 1640 and was layered on Ficoll (Lymphocyte Separation Medium 1077 g/ml, 710 g, RT, 20 min; BioWhittaker, cat. 17-829E, lot no. 0148 32) and centrifuged at 2000 rpm for 20 min. The mononuclear cell layer was removed, and erythrocytes within the pellet containing neutrophils were hypotonically lysed using ice-cold $NH_4Cl$ solution (155 mM $NH_4Cl$, 10 mM $NaHCO_3$, 0.1 mM EDTA, pH 7.4). The remaining neutrophils were washed twice and resuspended in RPMI 1640 supplemented with 10% FCS (RPMI-10).

Enrichment of human peripheral blood mononuclear cells: Human blood was diluted twice in RPMI 1640 and blood cells were layered on Ficoll (Lymphocyte Separation Medium 1077 g/ml, 710 g, RT, 20 min; BioWhittaker, Cambrex Bio Science Verviers, Verviers, Belgium, cat. 17-829E, lot no. 0148 32). Peripheral blood mononuclear cells (MNCs) were collected from the interphase, washed and resuspended in RPMI 1640 culture medium supplemented with 10% FCS, 2 mM L-glutamine, 5 U/ml penicillin, 50 µg/ml streptomycin (all derived from BioWhittaker) to which 25 mM HEPES (BioWhittaker) was added.

ADCC set up: Target B-cells (freshly isolated B-cells or from B-cell lines) were labeled with 20 µCi $^{51}Cr$ (Amersham Biosciences, Uppsala, Sweden) for 2 hours. After extensive washing in RPMI-10, the cells were adjusted to $1 \times 10^5$ cells/ml. Whole blood or isolated effector cells (50 µl; MNCs, PMNs) or plasma (50 µl), sensitizing antibodies (50 µl), and RPMI-10 (50 µl) were added to round-bottom microtiter plates (Greiner Bio-One GmbH, Frickenhausen, Germany). Assays were started by adding target cells (50 µl) giving a final volume of 200 µl. For isolated effector cells, an effector to target (E:T) ratio of 40:1 was used. For whole blood, an amount of 33 vol/vol % was used corresponding to an estimated effector to target ratio of 40:1. After incubation (3 hours, 37° C.), assays were stopped by centrifugation, and $^{51}Cr$ release from triplicates was measured in counts per minute (cpm) in a scintillation counter. Percentage of cellular cytotoxicity was calculated using the following formula:

$$\% \text{ specific lysis} = (\text{experimental cpm} - \text{basal cpm}) / (\text{maximal cpm} - \text{basal cpm}) \times 100$$

with maximal $^{51}Cr$ release determined by adding perchloric acid (3% final concentration) to target cells, and basal release measured in the absence of sensitizing antibodies and effector cells.

Statistics: Data were analyzed by one-way ANOVA, followed by Tukey's multi comparison post-hoc test. Analysis was performed using Graph Pad Prism (version 3.02 for Windows, Graph Pad Software, San Diego, Calif., USA).

Figure 20:
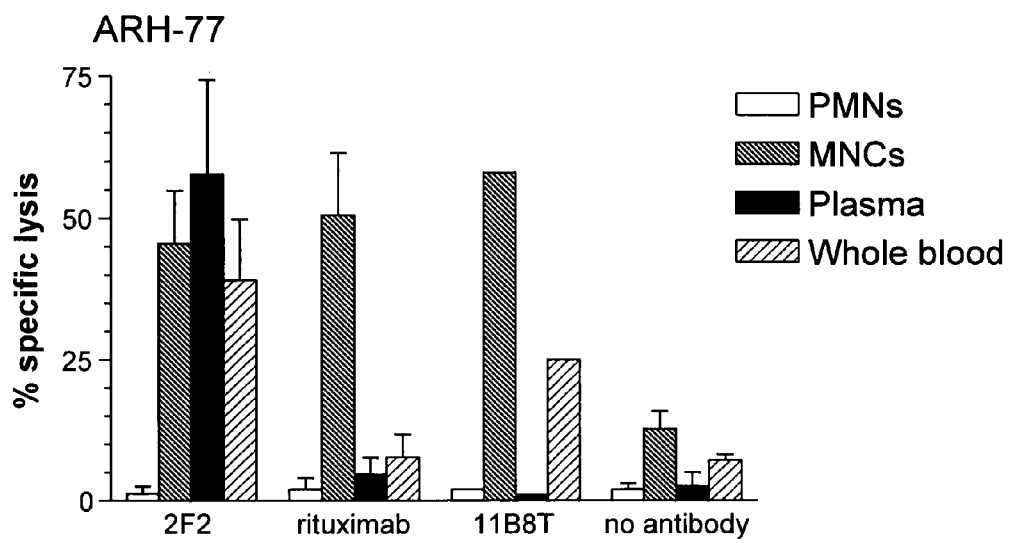
FIG. 20 shows lysis of ARH-77 cells by 2F2, rituximab, and 11B8T in the presence of PMNs, MNCs, plasma or whole blood.

Lysis of ARH-77 cells: In a first set of experiments, ARH-77 cells were used as target cells (FIG. 20). Addition of 2F2 (n=3), rituximab (n=3) or 11B8T (n=1) resulted in MNC-mediated lysis of ARH-77 cells of approximately 50%. No specific lysis was observed in the presence of neutrophils. Addition of plasma (to evaluate the role of complement) induced lysis of ARH-77 cells after incubation with 2F2, but not after incubation with rituximab (p<0.05, 2F2 vs. no antibody, ANOVA) or 11B8T. In the presence of whole blood, lysis of ARH-77 cells increased after incubation with 2F2 (p<0.05, 2F2 vs. rituximab and 2F2 vs. no antibody, ANOVA), but not with rituximab. Specific lysis induced by rituximab was in fact very low in the presence of whole blood. 11B8T induced cell lysis of approximately 25% (n=1) in the presence of whole blood. In the absence of antibody non-specific lysis of 10-15% was observed.

Figure 21:
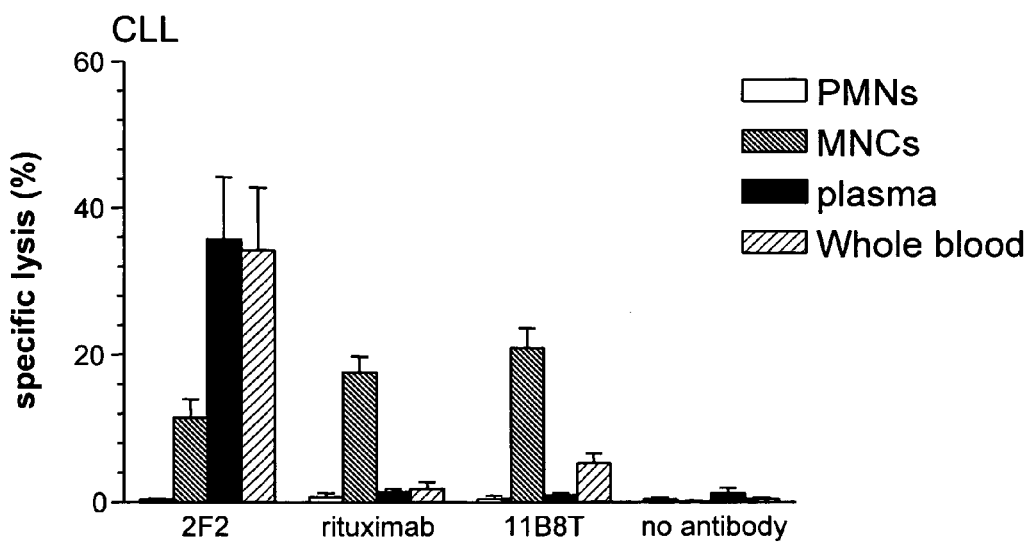
FIG. 21 shows lysis of B-CLL cells by 2F2, rituximab, and 11B8T in the presence of PMNs, MNCs, plasma or whole blood.

Lysis of B-CLL cells: In a second set of experiments, chronic B-lymphocytic leukaemia (B-CLL) cells obtained from B-CLL patients (n=12) were subcloned for 5 rounds and then used as target cells in the experiment (FIG. 21). In the absence of antibody, no specific lysis was observed, but addition of 2F2, 11B8T or rituximab (10 µg/ml) increased MNC-mediated specific lysis to 10-20% (p<0.001, ANOVA). Incubation of target cells with plasma and 2F2 induced specific lysis of B-CLL cells, whereas no specific lysis was observed with 11B8T or rituximab (p<0.001, ANOVA). Moreover, 2F2 mediated specific lysis of B-CLL cells after incubation in whole blood. No specific lysis of B-CLL cells by whole blood was observed with 11B8T (p<0.01, ANOVA) or rituximab (p<0.001, ANOVA). No specific lysis was observed in the presence of neutrophils.

Because rituximab was able to mediate effective ADCC but not CDC of the tumor cells tested, it is likely that whole blood-induced B-cell lysis by 2F2 is mediated via complement.

Figure 22:
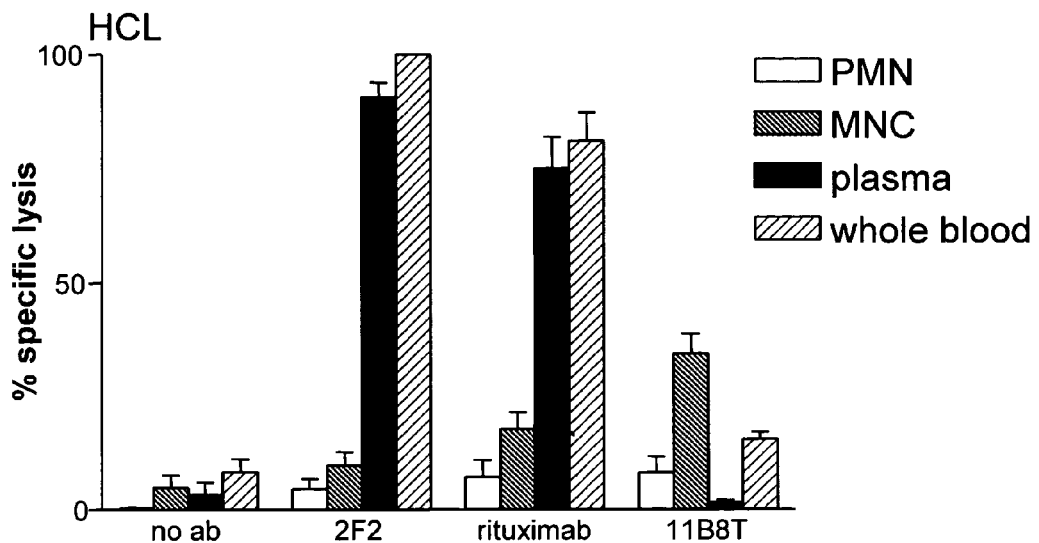
FIG. 22 shows lysis of HCL (hairy cell leukemia) cells by 2F2, rituximab, and 11B8T in the presence of PMNs, MNCs, plasma or whole blood.

Lysis of hairy cell leukaemia (HCL) cells: In a third set of experiments lysis of HCL cells by 2F2, 11B8T, and rituximab by ADCC or in the presence of plasma or whole blood was determined. Data are shown in FIG. 22. Whereas neutrophils could not mediate ADCC irrespective of the mAb used, 11B8T was able to induce MNC-mediated lysis of HCL cells more efficiently than 2F2 (p<0.001, ANOVA) or rituximab (p<0.05, ANOVA). 2F2 and rituximab were not able to induce MNC-mediated lysis of HCL cells. Plasma-mediated lysis of the cells was strongly enhanced with 2F2, as compared to rituximab (p<0.05, ANOVA), 11B8T (p<0.01, ANOVA) or without antibody (p<0.001, ANOVA). When lysis induced by anti-CD20 in the presence of whole blood was studied, 2F2 induced complete lysis of cells, and was superior to rituximab (p<0.01, ANOVA), 11B8T or no antibody added (p<0.001, ANOVA).

Figure 23:
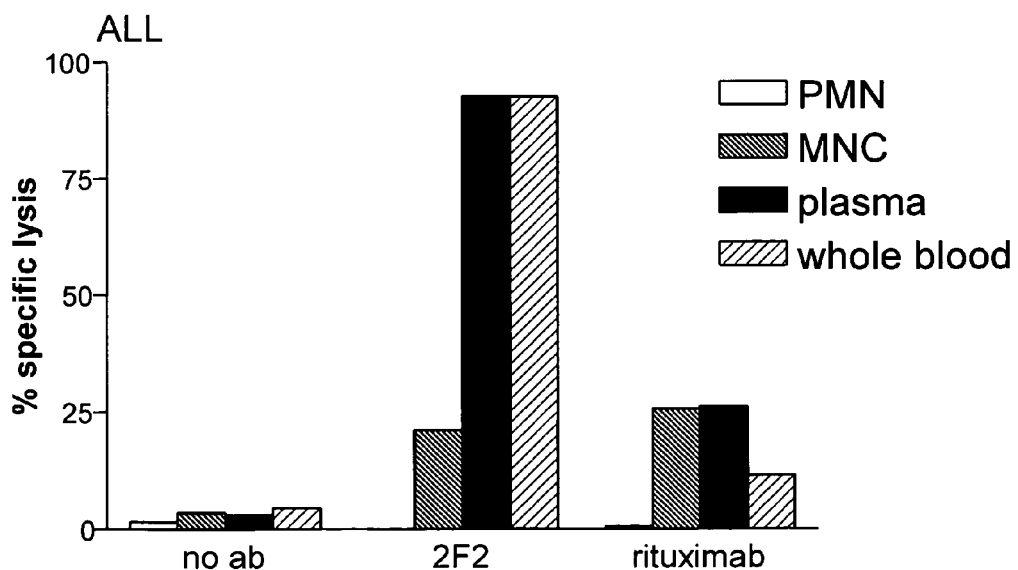
FIG. 23 shows lysis of B-ALL cells by 2F2, and rituximab, in the presence of PMNs, MNCs, plasma or whole blood.

Lysis of B-ALL cells: Using cells from two patients the ability of 2F2 and rituximab to induce lysis B-ALL cells by ADCC or complement was investigated (FIG. 23). As was observed in the previous experiments, 2F2 and rituximab induced MNC-mediated ADCC of B-ALL cells to a similar extent. But again 2F2 was able to induce plasma- and whole blood-mediated lysis of B-ALL cells, whereas rituximab was not.

Figure 24:
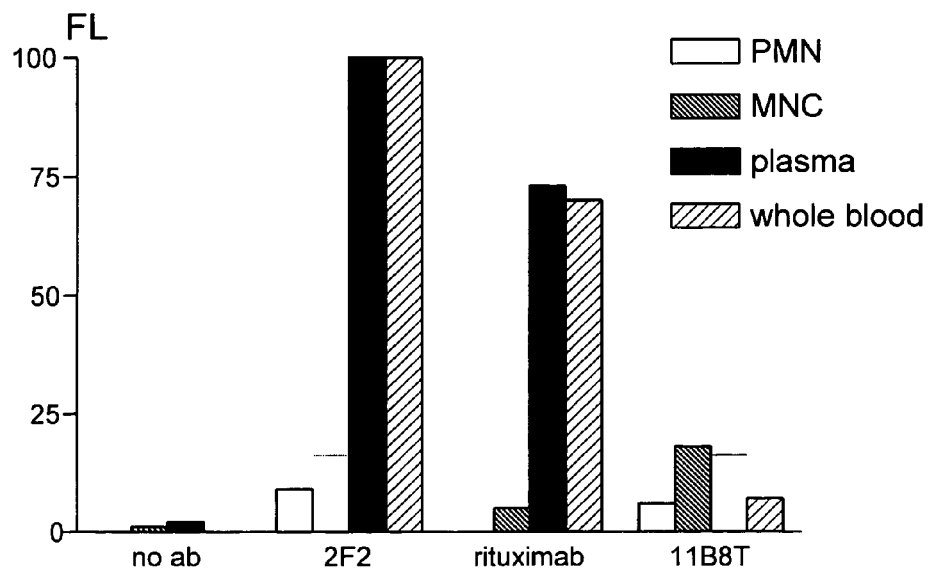
FIG. 24 shows lysis of follicular lymphoma (FL) cells by 2F2, rituximab, and 11B8T in the presence of PMNs, MNCs, plasma or whole blood.

Lysis of follicular lymphoma cells: When lysis of follicular lymphoma cells (n=2) was investigated, a different picture emerged (FIG. 24). A minor PMN-mediated lysis of cells with 2F2 was observed, and both 2F2 and rituximab were not able to induce MNC-mediated ADCC. 11B8T was still able to induce MNC-mediated lysis of approximately 20%. Although a relatively high plasma-mediated lysis was induced by. rituximab, complete plasma-mediated lysis was observed with 2F2. Also with whole blood, complete lysis was observed with 2F2, whereas 70% lysis with rituximab. Minimal plasma- or whole blood-mediated lysis by 11B8T was observed.

Figure 25:
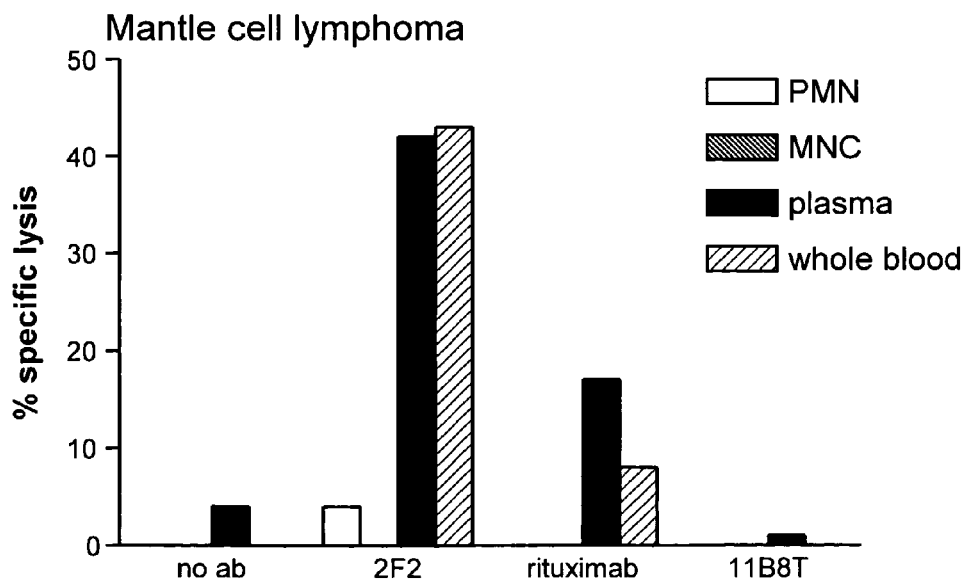
FIG. 25 shows lysis of mantle cell lymphoma cells by 2F2, rituximab, and 11B8T in the presence of PMNs, MNCs, plasma or whole blood.

Lysis of primary mantle cell lymphoma cells: Specific lysis of mantle cell lymphoma cells was more difficult to induce (n=1, FIG. 25). Minimal or no lysis by 2F2, 11B8T or rituximab was observed after addition of PMN or MNC and CD20 mAbs. However, 2F2 was still able to induce approximately 40% lysis by plasma or whole blood, whereas with rituximab only 10-20% of the cells were lysed. 11B8T was not able to induce lysis of primary mantle cell lymphoma cells.

Figure 26:
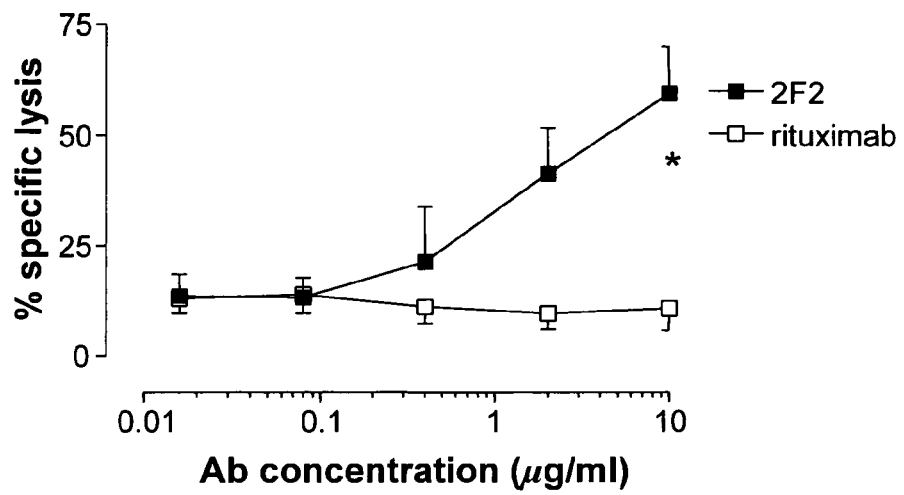
FIG. 26 shows concentration dependent lysis of ARH-77 cells by 2F2 and rituximab in the presence of whole blood.

Antibody concentration-dependent lysis of ARH-77 cells in whole blood: In a further experiment (n=4) dose-dependency regarding the induction of ADCC on ARH-77 cells in the presence of whole blood was analyzed. As can be seen in FIG. 26, titration of 2F2 induced a dose-dependent increase in the percentage of specific lysis (p<0.05: treatment-effect, two-way ANOVA) of ARH-77 cells. No specific lysis of ARH-77 cells was observed with rituximab.

ADCC Assay II

Preparation $^{51}$Cr-labeled target cells: ARH-77 cells and Raji cells were collected ($3 \times 10^6$ cells) in RPMI++, spun down (1500 rpm; 5 min), resuspended in 140 µl $^{51}$Cr (Chromium-51; CJS11-1 mCi, batch 12; 140 µl is about 100 µCi) and incubated (37° C. water bath; 1 hour). After washing cells (1500 rpm, 5 min, in PBS, 3×), cells were resuspended in RPMI++ and counted by trypan blue exclusion. Cells were brought at concentration of $2 \times 10^4$ cells/ml.

Preparation of effector cells: Fresh peripheral blood mononuclear cells (MNC) were isolated from 40 ml of heparin blood by Ficoll (Bio Whittaker; lymphocyte separation medium, cat 17-829E) via manufacturer's instructions. After resuspension of cells in RPMI++, cells were counted by trypan blue exclusion and adjusted to a concentration of $1 \times 10^6$ cells/ml.

ADCC set up: 50 µl RPMI++ was pipetted into 96 wells plates, and 50 µl of $^{51}$Cr-labeled targets cells were added. Thereafter, 50 µl of antibody was added, diluted in RPMI++ (final concentrations 10, 1, 0.1, 0.01 µg/ml). Cells were incubated (RT, 10 min), and 50 µl effector cells were added, resulting in an effector to target ratio of 50:1 (for determination of maximal lysis, 50 µl 5% Triton-X-100 was added instead of effector cells). Cells were spun down (500 rpm, 5 min), and incubated:(37° C., 5% $CO_2$, 4 hours). After spinning down the cells (1500 rpm, 5 min), 100 µl of supernatant was harvested into micronic tubes, and counted in a gamma counter. The percentage specific lysis was calculated as follows:

% specific lysis=(cpm sample−cpm target cells only)/ (cpm maximal lysis−cpm target cells only)×100

Statistics: Data were analyzed by one-way ANOVA, followed by Tukey's multi comparison post-hoc test. Analysis was performed using Graph Pad Prism (version 3.02 for Windows, Graph Pad Software, San Diego, Calif., USA).

Antibody concentration-dependent lysis of ARH-77 and Raji cells: 2F2T and 11B8T were tested for their ability to induce ADCC of ARH-77 and Raji cells (n=3) in comparison with rituximab.

Figure 27:
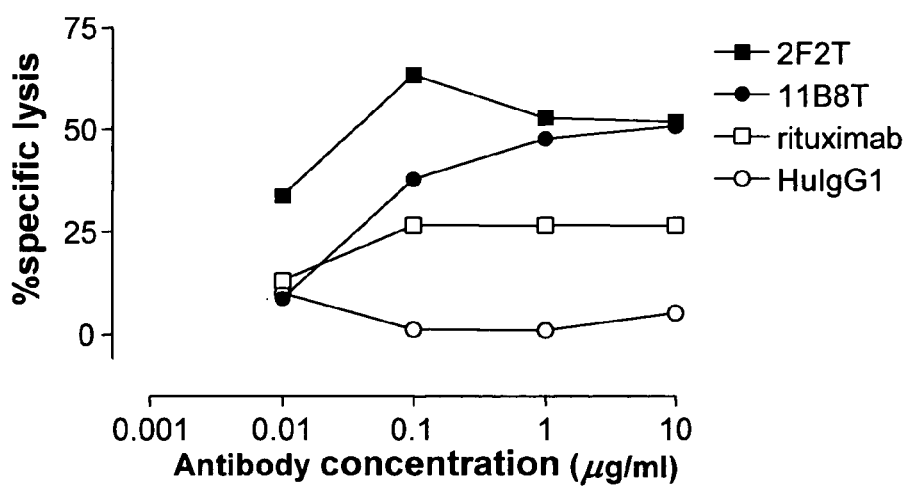
FIG. 27 shows MNC-mediated lysis of ARH-77 cells by 2F2T, 11B8T, and rituximab.

A dose-effect relation with CD20 mAbs was observed in ADCC of ARH-77 cells using MNC as effector cells (FIG. 27). Both 2F2T and 11B8T induced specific lysis of ARH-77 cells which was maximal (50%) at 10 µg/ml of mAb. Rituximab induced only 25% lysis of target cells. Addition of the isotype control antibody (HuMab-KLH) did not induce ADCC. No specific lysis was observed without addition of MNCs (data not shown).

Figure 28:
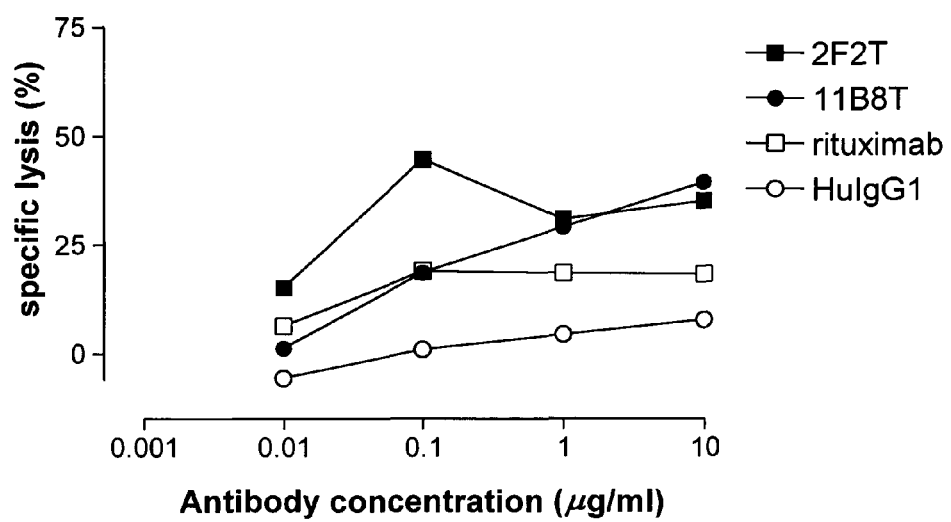
FIG. 28 shows MNC-mediated lysis of Raji cells by 2F2T, 11B8T, and rituximab.

When Raji cells were used as target cells, a similar picture as with ARH-77 cells emerged (FIG. 28). Both 2F2T and 11B8T induced MNC-mediated lysis of Raji cells, albeit that 2F2T seemed more potent than 11B8T at low concentrations. The maximum lysis reached with 2F2T and 11B8T was approximately 35%. Rituximab induced MNC-mediated lysis of Raji cells, although only 20% of target cells were susceptible to rituximab. Addition of the isotype control antibody (HuMab-KLH) did not induce ADCC. No specific lysis was observed without addition of MNCs (data not shown).

Example 8

FRET and Triton-X Insolubility Analysis

Preparation of Cy3- and Cy5-conjugated mAb for fluorescence resonance energy transfer (FRET): Monoclonal antibodies were directly conjugated to bifunctional NHS-ester derivatives of Cy3 and Cy5 (Amserham Biosciences UK Ltd) as described in the manufacturer's instructions. Briefly, mAb were dialyzed against 0.1 M carbonate/bicarbonate buffer (pH 9). Thereafter, dye was dissolved in $H_2O$, immediately added to 1 mg of the mAb, and incubated at room temperature in the dark for 45 min. The labeled mAbs were separated from the unconjugated dye by gel chromatography using a PD10-Sephadex G25 column equilibrated in PBS. Molar ratios of coupling were determined spectrophotometrically from $\epsilon_{552}$=150/mM/cm for Cy3, $\epsilon_{650}$=250/mM/cm for Cy5, and $\epsilon_{628}$=170/mM/cm for protein, and ranged from 5- to 8-fold excess dye:protein.

FRET analysis: Daudi cells were resuspended at $5 \times 10^6$ cells/ml in PBS/0.1% BSA, and equimolar donor (Cy3)-conjugated and acceptor (Cy5)-conjugated mAb were combined and added to the cell suspension (final concentration 10 µg/ml). Cells were incubated for 30 min in the dark, at 4° C. or 37° C. Each experiment included cells labeled with donor- and acceptor-conjugated mAb after pre-incubation with a 20-fold molar excess of unconjugated mAb, and cells labeled with donor- or acceptor-conjugated mAb in the presence of equimolar unlabeled mAb. To assess the association of labeled antigens, flow cytrometric FRET measurement was carried out using a FACScalibur (BD Biosciences). The fluorescence intensities at 585 nm (FL2) and 650 nm (FL3), both excited at 488 nm, and the fluorescence intensities at 661 nm (FL4), excited at 635 nm, were detected and used to calculate FRET according to the equitation below, where A is acceptor (Cy5), and D is donor (Cy3). All values obtained were corrected for autofluoresence using the following formula:

$$FRET=FL3(D,A)-FL2(D,A)/a-FL4(D,A)/b$$

where a=FL2(D)/FL3(D), and b=FL4(A)/FL3(A)

Correction parameters were obtained using data collected from single-labeled cells, and side angle light scattering was used to gate out debris and dead cells. FRET between donor and acceptor mAb derivatives on dually labeled cells is expressed in terms of acceptor sensitized emission at 488 nm. Larger FRET values indicate closer physical association of the donor- and acceptor labeled antibodies or a higher density of acceptor-labeled mAb in the vicinity of donor-labeled mAb.

Assessment of raft associated antigen by Triton X-100 (TX) insolubility: As a rapid assessment of the presence of antigen in raft microdomains, a flow cytometry method based on Triton X-100 (TX) insolubility at low temperatures was used, as described previously. In brief, Daudi cells were washed in RPMI/1% BSA and resuspended at $2.5 \times 10^6$/ml. The cells (100 µl) were then incubated with 10 µg/ml of FITC conjugated mAb for 15 min at 37° C., washed in cold PBS/1% BSA/20 mM sodium azide (PBS-BS), and the sample was divided in half. All samples were kept on ice throughout the remainder of the assay. One half was maintained on ice to allow calculation of 100% surface antigen levels, whilst the other was treated with 0.5% TX for 15 min on ice to determine to proportion of antigens remaining in the insoluble raft fraction. Cells were then maintained at 4° C. throughout the remainder of the assay, washed once in PBS-BS, resuspended in PBS-BS and assessed by flow cytometry. To determine the constitutive level of raft association of the target antigens, cells were first treated with 0.5% TX for 15 min on ice and washed in PBS-BS prior to binding of FITC-labeled mAb.

Figure 29A:
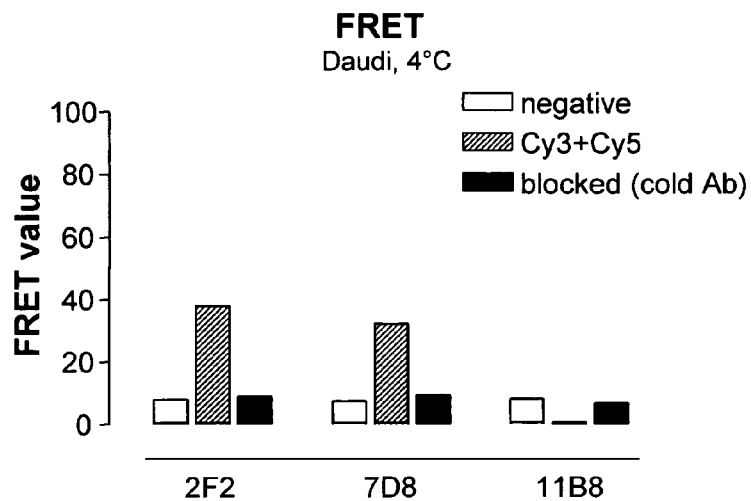
FIGS. 29A, B, and C are graphs showing clustering of CD20 in the lipid rafts upon incubation with 2F2, 7D8, or 11B8 using FRET analysis and Triton-X insolubility assay.
Figure 29B:
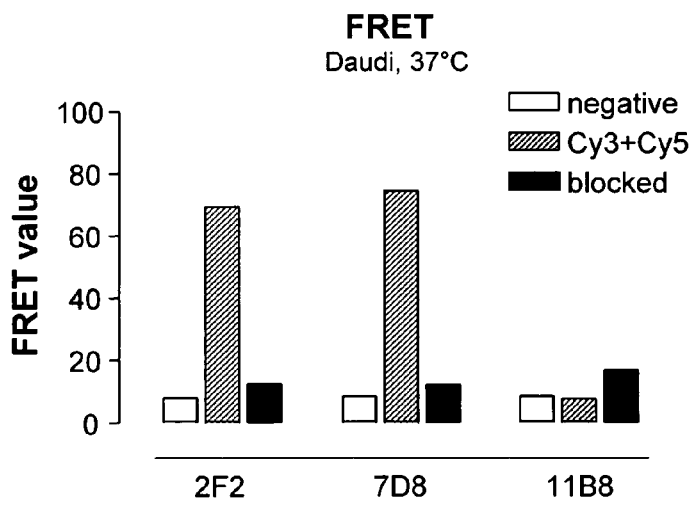
Figure 29C:
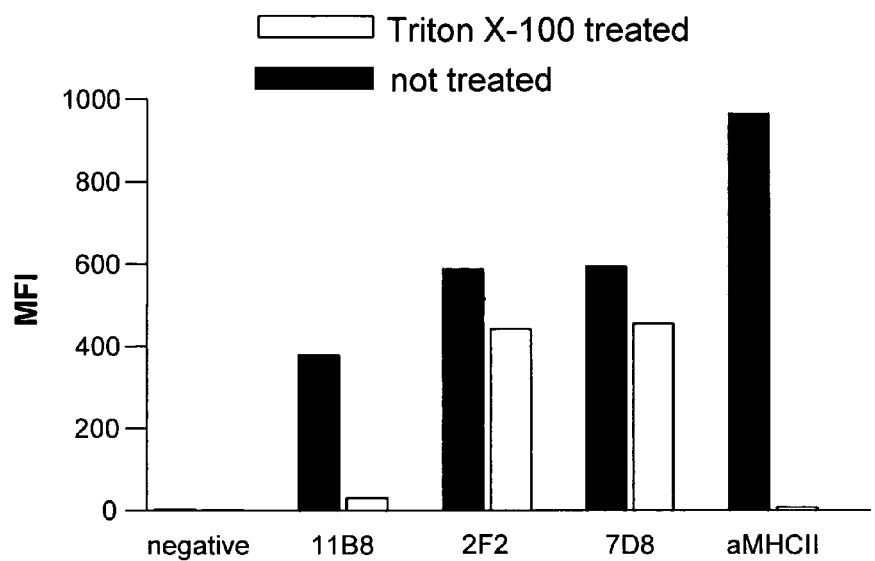

As shown in FIGS. 29A, 29B, and 29, fluorescence resonance energy transfer (FRET) analysis indicates clustering of CD20 upon incubation with 2F2 or 7D8. No such clustering was observed upon incubation with 11B8. These results are consistent with the TX treatment data, cf. FIG. 29C, (i.e., 2F2 and 7D8, unlike 11B8 remain with the insoluble fraction of the cell following binding) and support the concept that 2F2 and 7D8, upon binding, translocate CD20 into lipid raft compartment of the B cell membrane.

Figure 30:
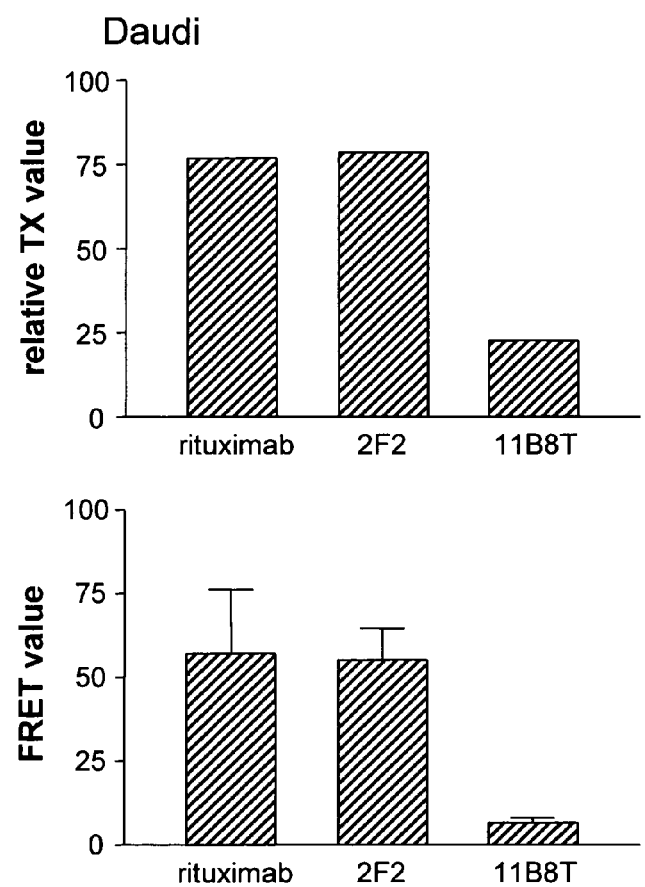
FIG. 30 shows clustering of CD20 in the lipid rafts upon incubation with 2F2, rituximab, or 11B8T using FRET analysis.
Figure 31:
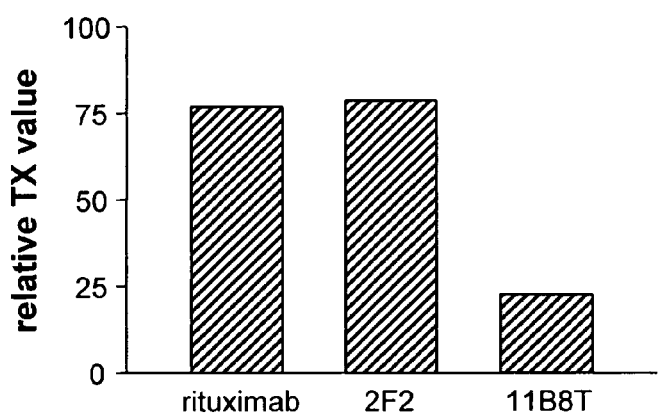
FIG. 31 shows the proportion of CD20 remaining in the insoluble raft fraction after treatment with Triton X-100 (TX) and incubation with 2F2, rituximab, or 11B8T.

As shown if FIG. 30 (FRET values and s.e.m. of three experiments using one-way ANOVA followed by Tukey's multi comparison post-hoc test) the FRET analysis indicates clustering of rituximab and 2F2, whereas no clustering was observed with 11B8T. These data are in agreement with the data obtained after treatment with 0.5% TX prior to binding of FITC-labeled mAbs as shown in FIG. 31 (n=2).

Preparation of lipid raft fractions and Western blotting: Another way to examine the association of CD20 with lipid rafts, is to investigate the distribution of CD20 between the raft and non-raft membrane fractions using the sucrose gradient fractionation method as disclosed by Deans, J. P., et al., *J. Biol. Chem.*, 1998. 273(1): pp 344-348, except that Optiprep (Sigma) was used instead of sucrose. Monoclonal antibodies directed against CD20 (10 μg/ml) were allowed to bind to Daudi cells ($1 \times 10^7$) for 20 min at 37° C. Following this incubation, the cells were pelleted, washed twice with PBS and lysed in ice-cold lysis buffer (1.0% TX in MES-buffered saline (25 mM MES, pH 6.5, 150 mM NaCl, 1 mM phenylmethylsulfonyl fluoride, 5 μg/ml aprotinin, 5 μg/ml leupeptin, 10 mM EDTA)). The cell pellet was resuspended thoroughly and incubated for 20 min on ice. Thereafter, the lysate was mixed with 400 μl cold 60% Optiprep (Sigma). The sample was overlaid with a 600 μl step of each 35%, 30%, 25%, 20%, 0% Optiprep in lysis buffer. The gradients were spun at 40.000 rpm at 4° C. for 18 hours. Six fractions from the top were collected, resolved on a 4-15% SDS-PAGE gel, transferred onto nitrocellulose membranes and incubated with primary antibody (mouse anti-CD20 polysera; Serotec, UK), followed by HRP-conjugated secondary antibody (rabbit anti mouse-HRP; Jackson, Bar Harbor, Me., USA). Blots were visualised using Supersignal West Dura extended duration substrate (Pierce, Woburn, Mass., USA).

Figure 32:
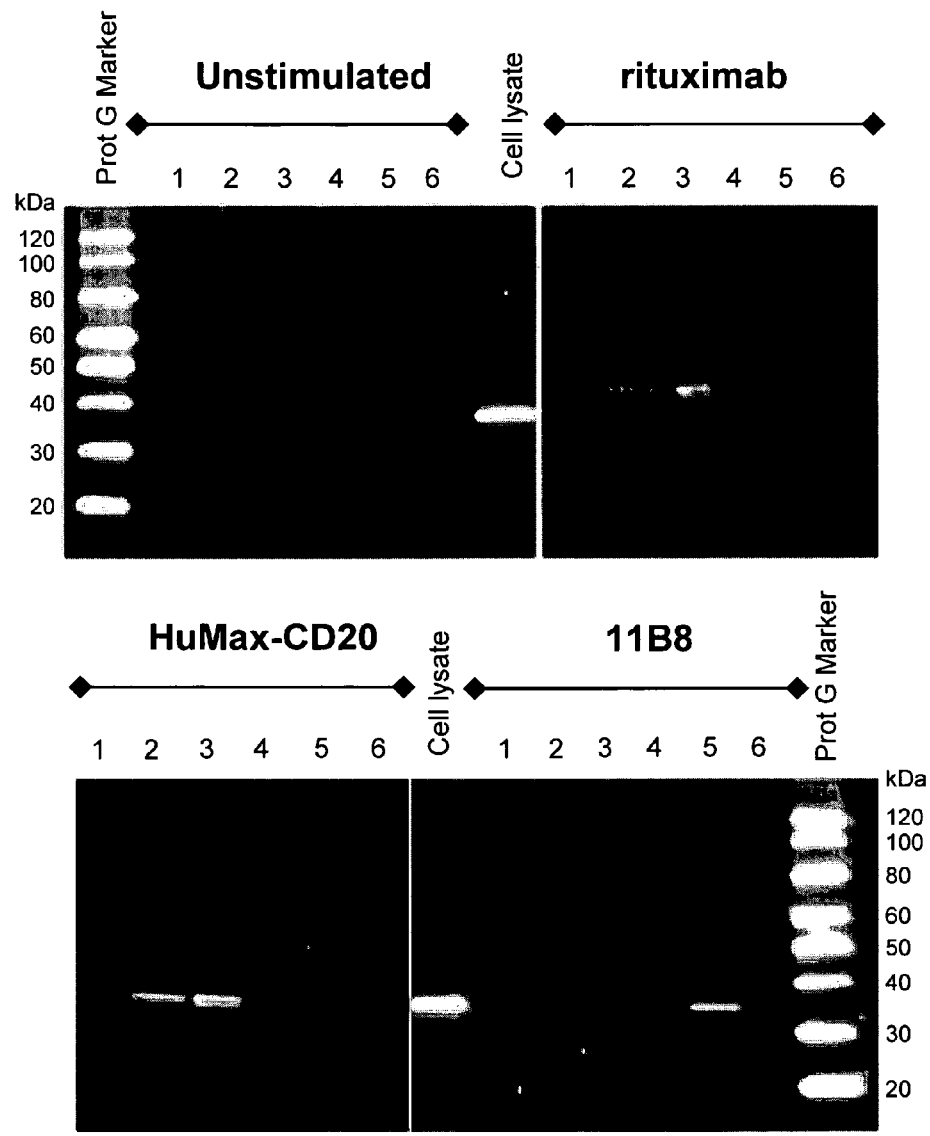
FIG. 32 shows the distribution of CD20 between the raft and non-raft membrane fractions upon stimulating Daudi cells with 2F2, rituximab, or 11B8T.
Figure 33A:
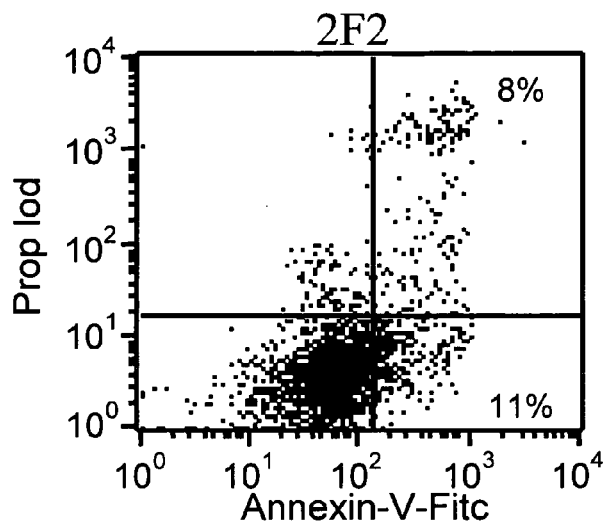
FIGS. 33A-G show apoptosis of Daudi cells by 2F2, 7D8, and 11B8 using flow cytometry.
Figure 33B:
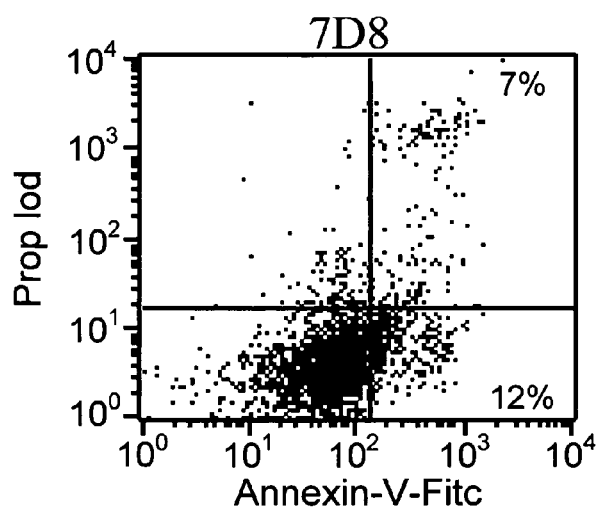
Figure 33C:
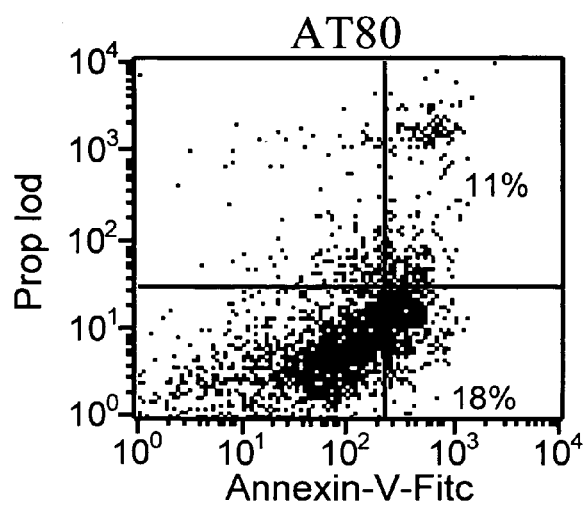
Figure 33D:
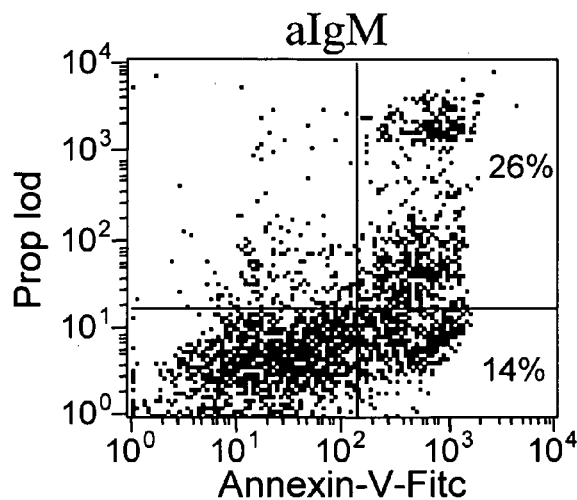
Figure 33E:
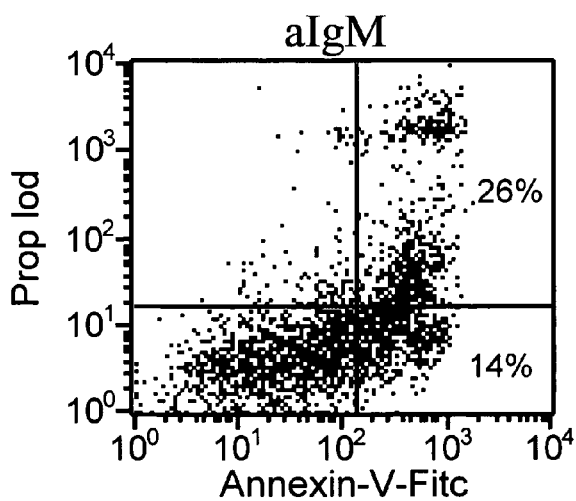
Figure 33F:
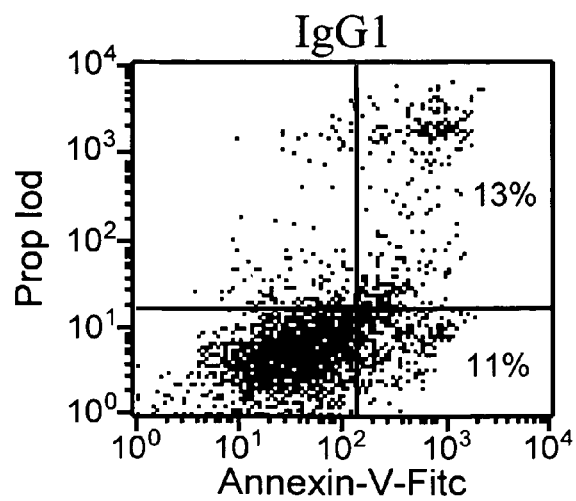
Figure 33G:
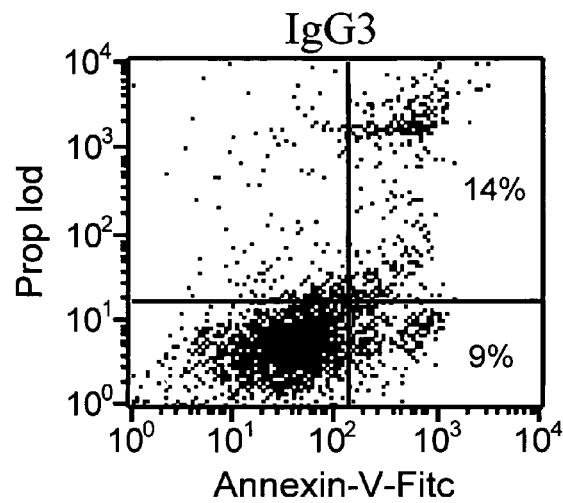

The results are shown in FIG. 32. As it can be seen, CD20 molecules are confined to the high-density fraction 5 (untreated cells). Cells treated with rituximab showed a distinct shift in CD20 distribution with a significant proportion in the lower density membrane fractions 2 and 3, coincident with the fraction where membrane rafts are expected to sediment. Cells treated with 2F2 also showed this shift to fractions 2 and 3. In contrast, cells treated with 11B8T for 20 min showed a similar distribution to untreated cells, with CD20 molecules in fraction 5. In conclusion binding to 2F2 and rituximab induces a shift of CD20 molecules to the lower density membrane fractions, whereas binding to 11B8T does not.

Example 9

Apoptosis of Burkitt Cell Lines with Human Antibodies Against CD20

Apoptosis: Daudi cells, $0.5 \times 10^6$ in 1 ml tissue culture medium, were placed into 24-well flat-bottom plates with 1 or 10 μg/ml mAb or control antibodies, and incubated at 37° C. After 20 hours, cells were harvested, washed in Annexin-V-FITC binding buffer (BD biosciences) and labeled with Annexin V-FITC (BD biosciences) for 15 min in the dark at 4° C. The cells were kept at 4° C. until analysis. Each sample (150 μl) was added to 10 μl of PI solution (10 μg/ml in PBS) in a FACS tube. The mixture was assessed immediately by flow cytometry using a FACScalibur flow cytometer with CellQuest pro software (BD Biosciences, Mountain view, Calif.). At least 10,000 events were collected for analysis.

Induction of apoptosis in Daudi cells: Daudi cells were incubated for 20 hours in the presence of human antibodies against CD20 (1 μg/ml) (without the addition of a secondary cross-linking antibody). Induction of apoptosis was assessed by AnnexinV/PI staining using flow cytometry.

As shown in FIGS. 33A-G, 11B8 shows clear evidence of inducing apoptosis (similar to that induced by an anti-IgM antibody). 2F2 and 7D8 did not induce apoptosis of Daudi cells. An apoptosis-inducing mouse anti-CD20 antibody, AT80, was used as a control.

Figure 34:
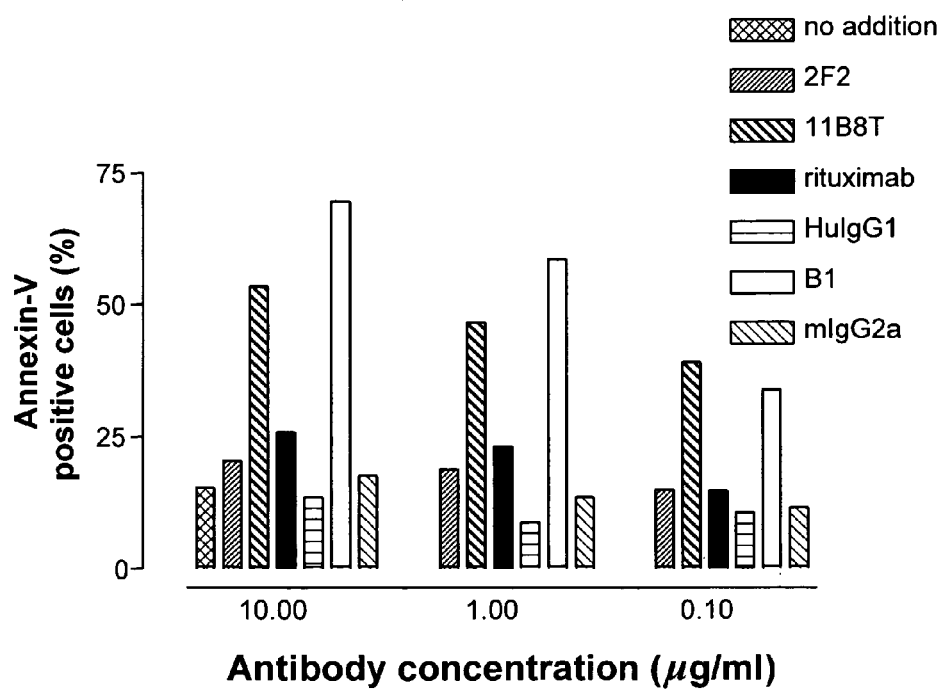
FIG. 34 shows induction of apoptosis of Raji cells by 2F2, 11B8T, rituximab, or B1 using flow cytometry.

Induction of apoptosis in Raji cells: Induction of apoptosis of Raji cells was tested with a concentration range of CD20 mAbs. FIG. 34 shows the percentage of annexin-V-positive cells. As can be seen from FIG. 34, the positive control mouse anti-human CD20-mAb, B1, induced a concentration-dependent increase in apoptosis of Raji cells with a maximum of approximately 70% at 10 μg/ml mAb. Also 11B8 was a strong inducer of apoptosis, resulting in apoptosis of Raji cells with a maximum of 53.4% at 10 μg/ml mAb. On the other hand, 2F2 and rituximab were very poor in inducing apoptosis of Raji cells, with slightly elevated levels of apoptosis compared to negative control levels.

Figure 35A:
FIG. 35A shows induction of apoptosis of Daudi cells by 2F2T, 11B8T, rituximab, or B1 using flow cytometry.
Figure 35B:
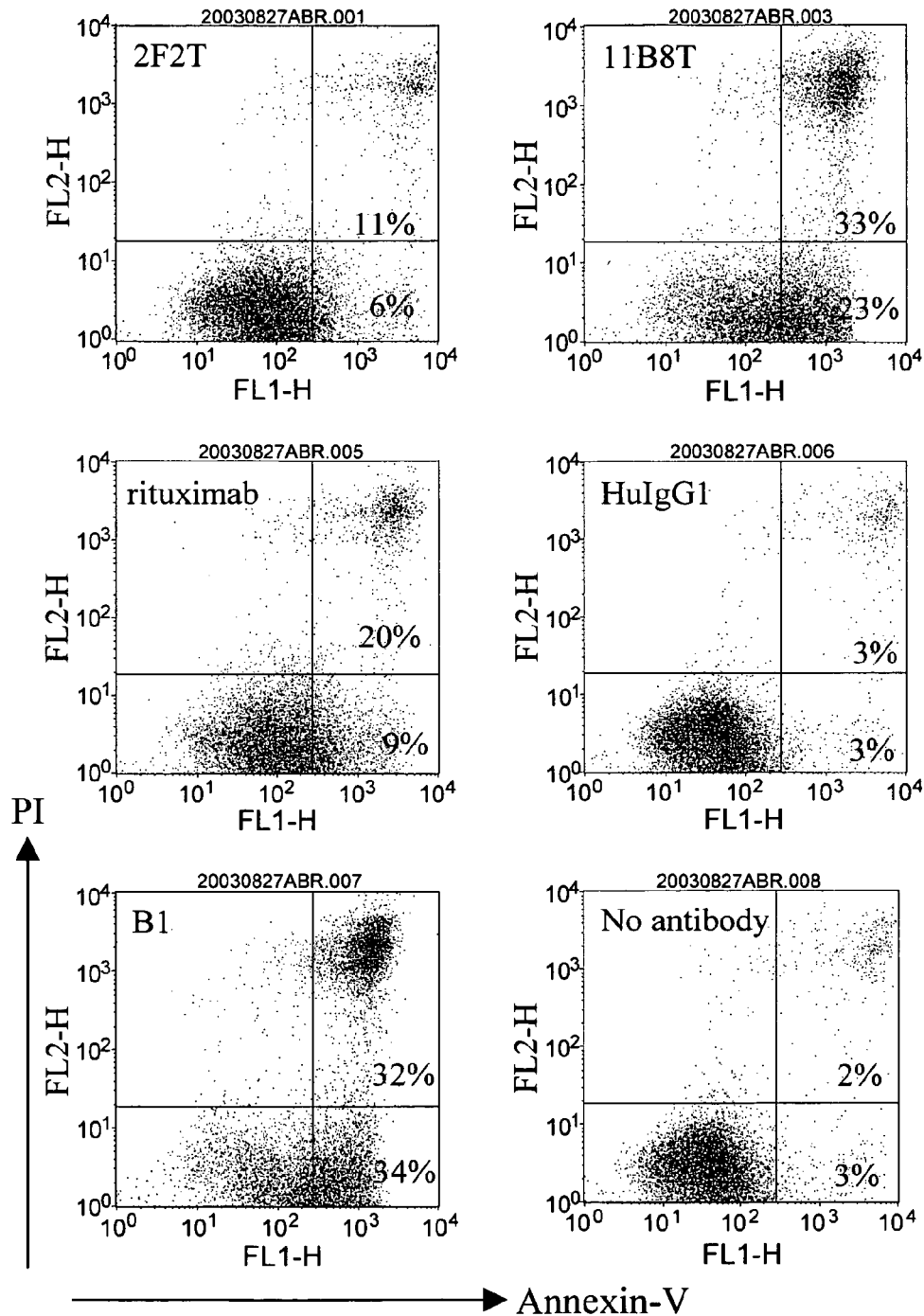
FIG. 35B shows early stage and late stage apoptosis of Daudi cells by human monoclonal antibodies 2F2T, 11B8T, rituximab, and B1 using flow cytometry.
Figure 36A:
FIGS. 36A-E show homotypic adhesion of Ramos-EHRB cells by 2F2, 7D8, and 11B8 using light microscopy.
Figure 36B:
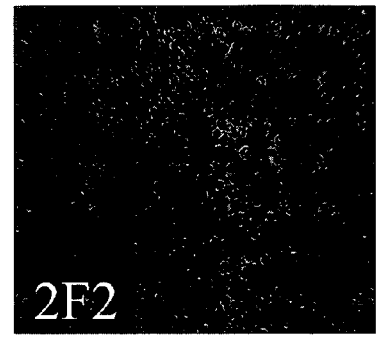
Figure 36C:
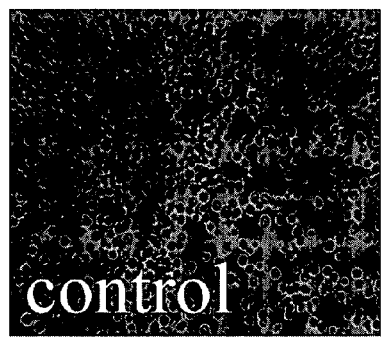
Figure 36D:
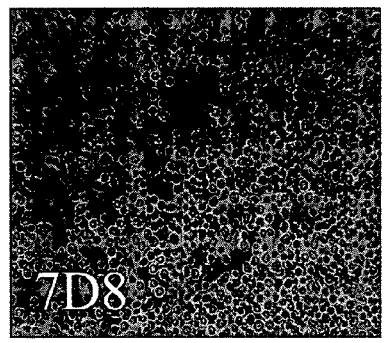
Figure 36E:
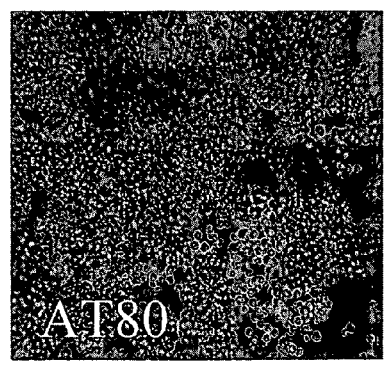

Induction of apoptosis in Daudi cells: The same picture emerged when Daudi cells were used as target cells, after addition of 1.0 μg/ml CD20 mAb (FIGS. 35A and 35B). Data in FIG. 35A show the total of annexin-V positive cells, and data in FIG. 35B (the X-axis showing annexin-V, and the Y-axis showing PI) show the percentages of Daudi cells in early apoptosis (annexin-V positive and PI negative) and late apoptosis (annexin-V positive and PI positive). Again, Both B1 (65.9%) and 11B8T (56.3%) were strong inducers of apoptosis (FIG. 36), when used at a concentration of 1.0 μg/ml. Addition of 2F2T resulted in a low level of apoptotic Daudi cells (17%). Addition of rituximab resulted in approximately 29% apoptosis of Daudi cells. Addition of isotype control antibody HuMab-KLH did not induce apoptosis of Daudi cells (6%).

Example 10

Homotypic Adhesion of Cells with Human Antibodies Against CD20

Homotypic aggregation correlates with induction of apoptosis. Therefore, the ability of the anti-CD20 mAbs to induce homotypic aggregation of B cells was investigated Homotypic aggregation of Ramos-EHRB cells: Ramos-EHRB cells ($0.5 \times 10^6$ in 1 ml tissue culture medium) were incubated at 37° C. for 4 hours in the presence of anti-CD20 antibodies 11B8, 2F2, or 7D8 (without cross-linking) and induction of homotypic adhesion was assessed by light microscopy (as described above).

As shown in FIGS. 36A-E, 11B8 caused extensive aggregation of Ramos-EHRB cells (similar to the aggregation caused by murine anti-CD20 antibody, AT80). 2F2, and 7D8 did not induce homotypic aggregation of Ramos cells.

Figure 37:
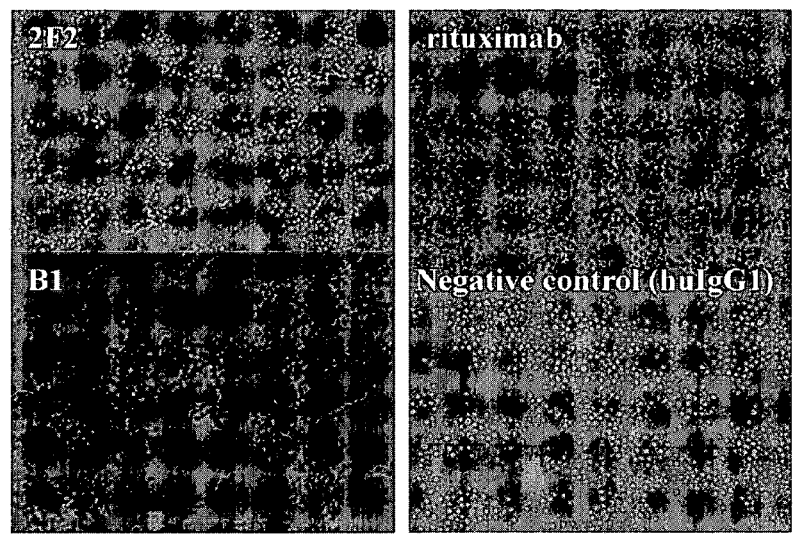
FIG. 37 show homotypic adhesion of Daudi cells by 2F2, rituximab, and B1 using light microscopy.

Homotypic aggregation of Daudi cells: Daudi cells were placed into 24-well flat-bottom plates with 1 or 10 µg/ml anti-CD20 mAbs or control antibody, and incubated at 37° C. for 4 hours. The extent of homotypic aggregation was determined by light microscopy. As can be seen from FIG. 37, 2F2 hardly induced homotypic aggregation of Daudi cells, with 1.0 µg/ml (and 10 µg/ml, data not shown). Rituximab gave little homotypic aggregation of Daudi cells. In contrast, the B1 antibody was a strong inducer of homotypic aggregation.

Example 11

Immunotherapy Using Human Antibodies Against CD20

Figure 38:
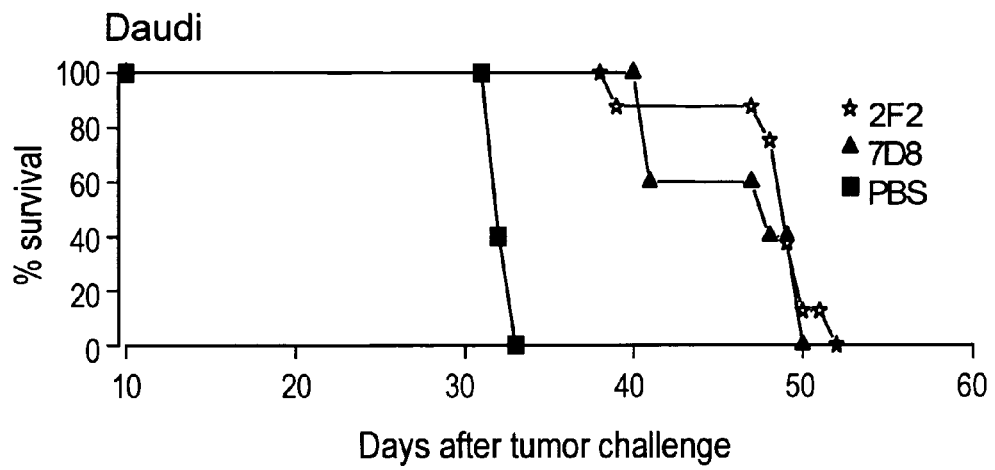
FIG. 38 is a graph showing the percent survival of SCID mice injected with Daudi cells and treated with 2F2 or 7D8.

Therapy with high dose (100 µg) 2F2 and 7D8 of SCID mice challenged with Daudi cells: The SCID mice were obtained from Harlan UK Ltd., Blackthorn, Oxon, UK, and bred and maintained under pathogen free conditions. Daudi cells ($2.5 \times 10^6$) were injected i.v. into the tail vein of cohorts of 12-16 weeks old SCID mice, followed 7 days later by injection of 100 µg of 2F2 or 7D8 via the same route. Animals were sacrificed upon presentation of limb paralysis, according to the instructions of the animal ethics committee. As shown in FIG. 38, survival of the mice is prolonged after treatment with 2F2 or 7D8.

Figure 39:
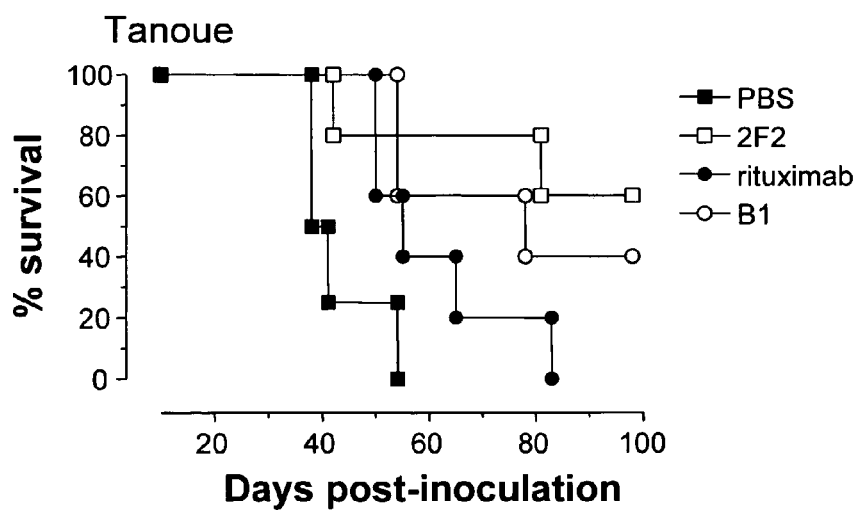
FIG. 39 shows the percent survival of SCID mice injected with Tanoue cells and treated with 2F2, rituximab, or B1.

Therapy with high dose (100 µg) 2F2 and rituximab of SCID mice challenged with Tanoue cells: Tanoue cells ($2.5 \times 10^6$ in 200 µl PBS) were injected i.v. into the tail vein of cohorts of 12-16 week old SCID mice (Harlan UK Ltd., Blackthorn, Oxon, UK) followed 7 days later by the injection of 100 µg (in 200 µl PBS) of anti-CD20 mAb via the same route. In this experiment, 2F2 was compared to rituximab and B1. Animals were sacrificed upon presentation of rear-limb paralysis. The results are shown in FIG. 39. At day 39, the first two control mice died, and death within this group was complete at day 54. Only one mouse died within this time interval following 2F2 treatment and survival was considerably increased for the other mice in this group. One mouse died 81 days following injection of the tumor cells and the remaining mice (60% of the total number) survived beyond the termination of the experiment at 100 days post tumor challenge. Rituximab in contrast only increased survival for 2 out of 5 mice (dying at 66 and 83 days post challenge) and none of the mice survived until the end of the experiment. In the B1-group, the survival of SCID mice was similar to that in the 2F2 group, with two mice dying on day 48, and one mouse on day 76. In this group, forty percent was alive at the time the experiment was terminated.

Dose response of 2F2 and rituximab treatment of SCID mice challenged with Daudi cells: To assess the efficacy of 2F2 in comparison to rituximab in protection against tumorigenesis, a dose titration was performed in therapy of SCID mice challenged with Daudi tumor cells. Daudi cells express more CD20 than Tanoue cells and are more sensitive to killing in vitro. 10 groups of SCID mice (4 per group) and 1 control group (5 SCID mice) were injected with $2.5 \times 10^6$ Daudi cells (in 200 µl PBS) i.v. on day 0, and then treated with 20, 5, 2, 0.5 or 0.1 µg (in 200 µl PBS) rituximab, 2F2 or PBS (control) i.v. on day 7. Animals were sacrificed upon presentation of rear-limb paralysis. The results are shown in FIG. 40.

In the control group, all mice died within the time interval of 26-29 days. However, a clear dose-effect relation was observed with 2F2 (FIG. 40, upper graph). Whereas no effect was observed with doses of 0.1 µg and 0.5 µg 2F2, as little as 2 µg 2F2 substantially extended survival until day 41, 5 µg 2F2 extended survival until day 47, and 20 µg 2F2 extended survival even until day 50.

Figure 40:
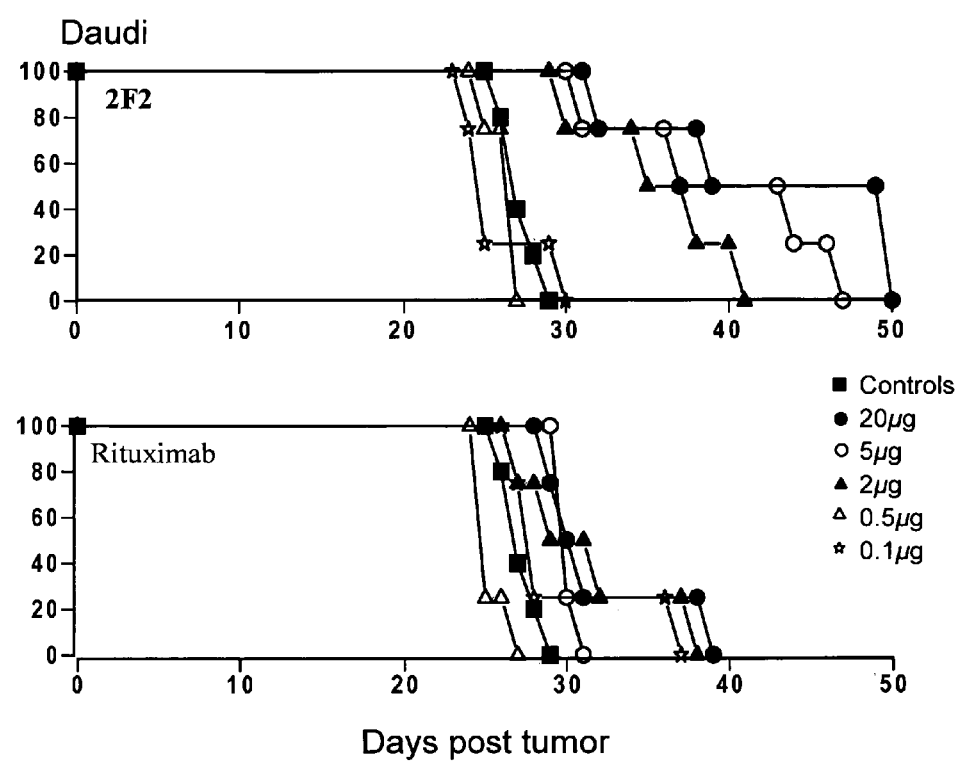
FIG. 40 shows the percent survival of SCID mice injected with Daudi cells and treated with different concentrations of 2F2 or rituximab.

In contrast, rituximab even tested at the highest dose of 20 µg only slightly increased survival and no dose-effect relation was therefore observed at the lower concentrations tested (FIG. 40, lower graph).

Figure 41:
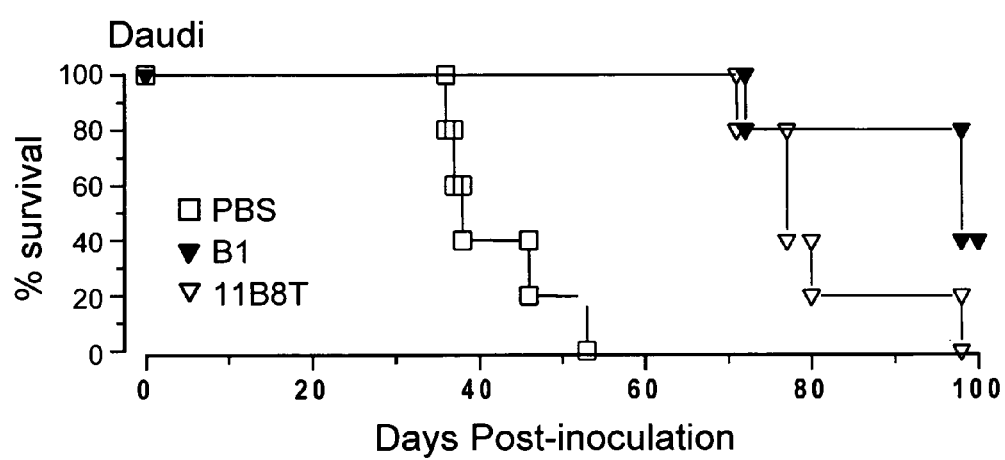
FIG. 41 shows the percent survival of SCID mice injected with Daudi cells and treated with 11B8T or B1.

Therapy of SCID mice with Daudi tumors by 11B8T and B1: Daudi cells ($2.5 \times 10^6$) in 200 µl PBS were injected i.v. into the tail vein of cohorts of 12-16 week old SCID mice, followed 7 days later by the injection of 100 µg 11B8 or B1 in 200 µl PBS via the same route. Animals were sacrificed upon presentation of rear-limb paralysis. In control mice treated with PBS, all mice died within a time interval of 35-53 days (FIG. 41). 11B8T treatment strongly protected the mice, with mice dying between 72 and 98 days post tumor challenge. In the B1-treatment group, most mice survived until day 98 and 40% of the mice survived beyond the end of the experiment, i.e., day 100.

Example 12

Evaluation of Anti-CD20 Antibodies in a Daudi-luc Xenograft Model Using SCID Mice The therapeutic efficacy of anti-CD20 antibodies was evaluated in a mouse model in which disseminated outgrowth of human B-cell tumor cells is followed using external optical imaging. In this model tumor cells are transfected with firefly luciferase. Upon administration of luciferin (Molecular Probes, Leiden, The Netherlands) to the mice the labeled cells can be detected in vivo by bioluminescent imaging using a highly sensitive CCD camera, cf. Wetterwald et al. (2002) *American Journal of Pathology*, 160(3):1143-1153.

Daudi cells were transfected with gWIZ luciferase from Gene Therapy Systems (San Diego, Calif.) and cultured in RPMI with 10% FCS, Pen/Strep, Sodium Pyruvate and 1 µg/ml puromycin (Sigma). Cells were analysed for luciferase expression (expressed in $RLU/1 \times 10^5$ cells) in a luminometer and for CD20 expression by FACS. $2.5 \times 10^6$ luciferase-transfected Daudi cells/mouse were injected i.v. into SCID mice. Eight days after inoculation, the mice received a single dose (10 µg) treatment of 2F2T, 11B8T, rituximab, B1 or isotype control antibody (huIgG1) (6 mice per treatment group). For imaging, mice were anesthetized by i.p. injection of a mixture of ketamine/xylazine/atropine. Synthetic D-Luciferin (sodium salt, Molecular Probes) was given i.p. at a dose of 25 mg/ml. Mice were then placed in a light tight box and after 3 min, imaging was started using a VersArray 1300B liquid nitrogen cooled CCD detector (Roper Scientific). Photons emitted from the luciferase were counted over an exposure period of 5 min. Under illumination black and white images were made for reference. MetaVue software (Universal Imaging Corp) was used for data collection and image analysis. Statistical significance of differences between groups was established using one-way analysis of variance with a Newman-Keuls post test using GraphPad PRISM version 3.02 (Graphpad Software Inc).

Figure 42:
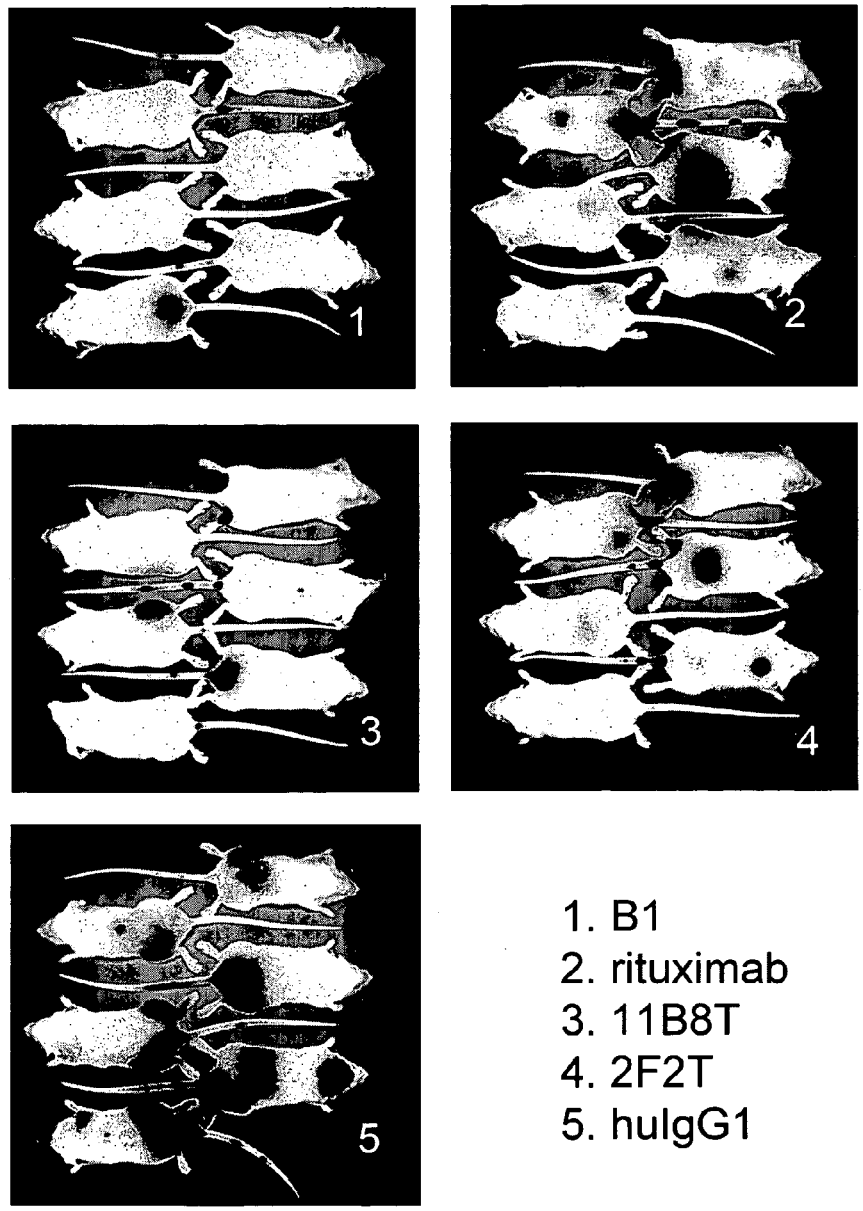
FIG. 42 shows bioluminescence imaging of tumor cells in SCID mice on day 39 (31 days after treatment with 10 µg of B1, rituximab, 11B8T, 2F2T, or huIgG1). The bioluminescence is represented in red color (the dark areas in the mice) (light intensity >50 photons per 5 min) as overlay on the black and white body image of the mice.

Imaging from the back side was performed at one-week intervals. On day 8, the day of treatment, light emission was only detected at the inoculation sites in the tail. Tumor formation at distant sites was detected on day 14 in all mice from the isotype control group (huIgG1) and in one mouse from the rituximab group. In the following weeks light emission steadily increased. FIG. 42 gives the images of all mice made on day 39 (31 days after treatment), in which bioluminescence is represented in red color (the dark areas in the mice)

Figure 43:
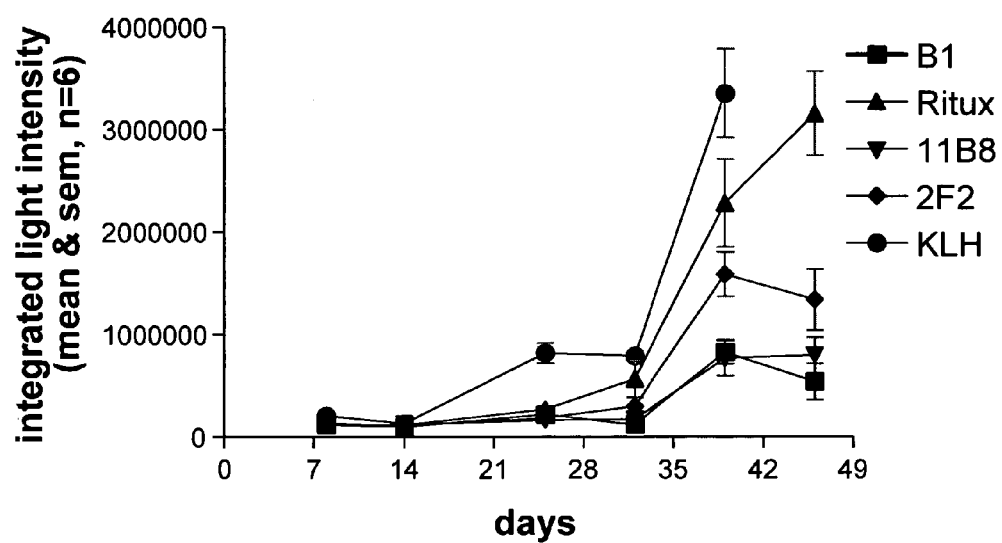
FIG. 43 shows the tumor mass in each mouse quantified on day 25, 32, 39, and 46 following administration, on day 8, of 10 µg of B1, rituximab, 11B8T, 2F2T, or huIgG1 by integrating the light signals over the body surface.

(light intensity>50 photons per 5 min) as overlay on the black and white body image of the mice. The tumor mass in each mouse was quantified on day 25, 32, 39, and 46 by integrating the light signals over the body surface, cf. FIG. 43. The fastest tumor growth was observed in the isotype control group. Treatment with rituximab gave significant inhibition of tumor growth. However, tumor growth inhibition by 2F2T, 11B8T and B1 was significantly more potent (see below Table 2 for significance levels.

TABLE 2

Significance levels of differences in integrated light intensity between groups at different time points

|  | Day 25 | Day 32 | Day 39 | Day 46 |
|---|---|---|---|---|
| B1 vs. rituximab | $P > 0.05$ | $P < 0.05$ | $P < 0.01$ | $P < 0.001$ |
| B1 vs. 11B8T | $P > 0.05$ | $P > 0.05$ | $P > 0.05$ | $P > 0.05$ |
| B1 vs. 2F2T | $P > 0.05$ | $P > 0.05$ | $P > 0.05$ | $P > 0.05$ |
| B1 vs. huIgG1 | $P < 0.001$ | $P < 0.001$ | $P < 0.001$ |  |
| rituximab vs. 11B8T | $P > 0.05$ | $P < 0.05$ | $P < 0.01$ | $P < 0.001$ |
| rituximab vs. 2F2T | $P > 0.05$ | $P > 0.05$ | $P > 0.05$ | $P < 0.001$ |
| rituximab vs. huIgG1 | $P > 0.05$ | $P > 0.05$ | $P < 0.05$ |  |
| 11B8T vs. 2F2T | $P > 0.05$ | $P > 0.05$ | $P > 0.05$ | $P > 0.05$ |
| 11B8T vs. huIgG1 | $P < 0.001$ | $P < 0.001$ | $P < 0.001$ |  |
| 2F2T vs. huIgG1 | $P < 0.001$ | $P < 0.01$ | $P < 0.01$ |  |

Example 13

Pilot and Pharmacokinetic Study in Cynomolgus Monkeys

The objective was to determine the pharmacokinetic pattern and pharmacological effects of 2F2 in cynomolgus monkeys (approximately 2 years old; weight range of 2.1-2.6 kg) following once daily intravenous infusion administrations (via the saphenous vein) for 4 consecutive days. The study also compared the pharmacological effects of rituximab in order to determine its equivalent potential. For this purpose, 6 male and 6 female cynomolgus monkeys were assigned to 6 dose groups that received 2F2 or rituximab at dose levels of 1.25, 6.25 and 12.5 mg/kg/day at a constant dose volume of 10 ml/kg for 4 consecutive days, in total 5, 25 and 50 mg/kg, respectively. On completion of the last dose administration, the animals were retained for a post dose observation period of 130 days. The practices and procedures adopted during this study were consistent with the OECD Principles of Good Laboratory Practice as set forth by the United Kingdom Department of Health. All animals were observed at regular intervals for signs of ill health or reaction to treatment and were subjected to a physical examination. Laboratory investigations of haematology, coagulation, clinical chemistry and urine analysis were performed during the study. Blood samples and lymph node biopsies were obtained (from the superficial lymph nodes) for flow cytometry analysis throughout the dosing and post dose observation periods. The following cell phenotypes were analysed by flow cytometry: CD3, CD4, CD8, CD20 and CD21. On completion of the post dose observation period the animals were sacrificed and subjected to a detailed necropsy.

Figure 44A:
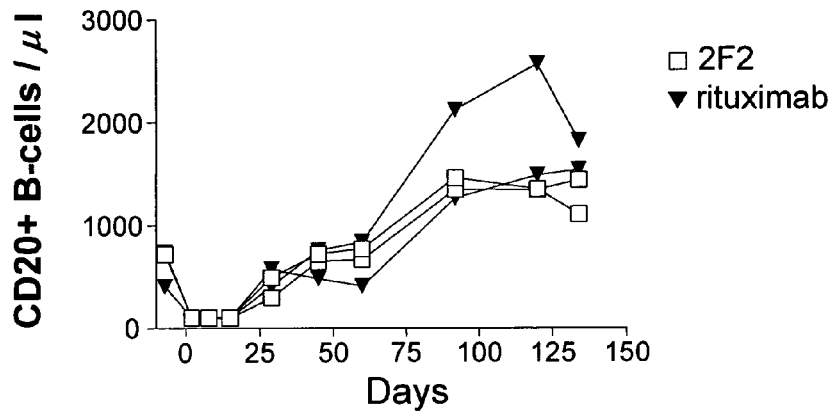
FIGS. 44A-C show flow cytometric analysis of CD20$^+$ cells in peripheral blood of cynomolgus monkeys following intravenous administration of 2F2 or rituximab at different dosages, 4×1.25 mk/kg (A), 4×6.25 mg/kg (B), or 4×12.50 mg/kg (C).
Figure 44B:
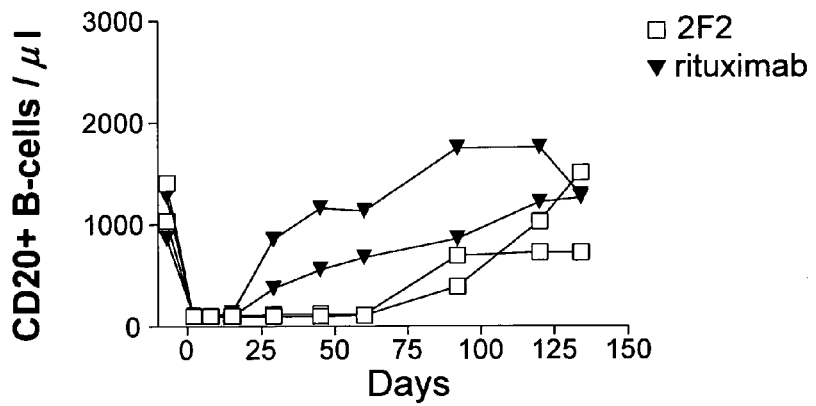
Figure 44C:
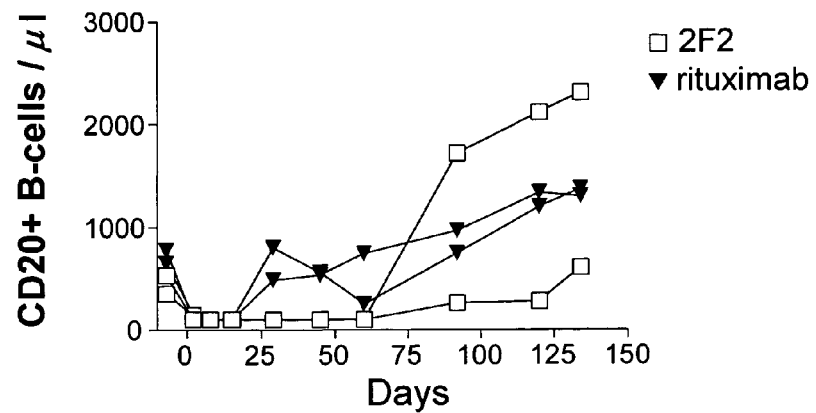
Figure 45A:
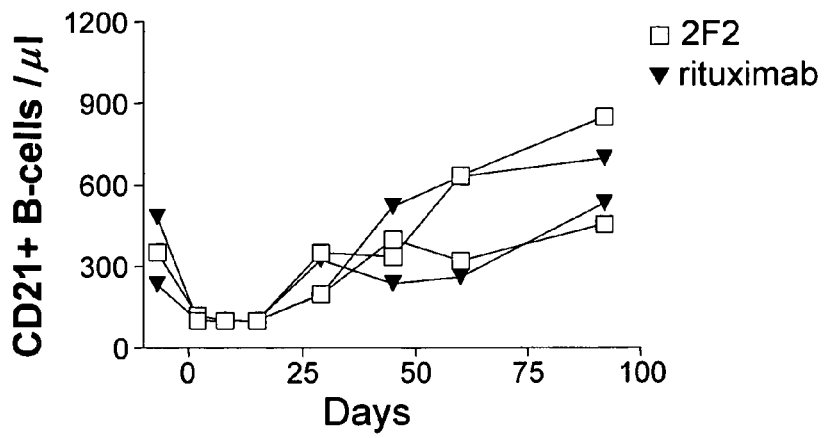
FIGS. 45A-C show flow cytometric analysis of $CD21^{30}$ cells in peripheral blood of cynomolgus monkeys following intravenous administration of 2F2 or rituximab at different dosages, 4×1.25 mk/kg (A), 4×6.25 mg/kg (B), or 4×12.50 mg/kg (C).
Figure 45B:
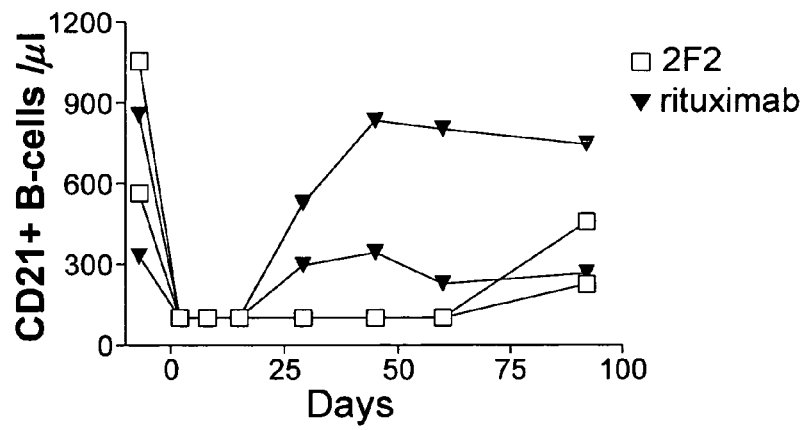
Figure 45C:
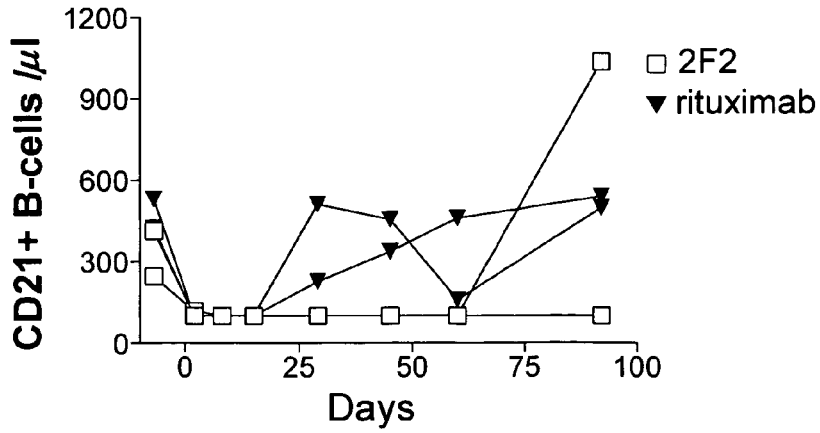
Figure 46A:
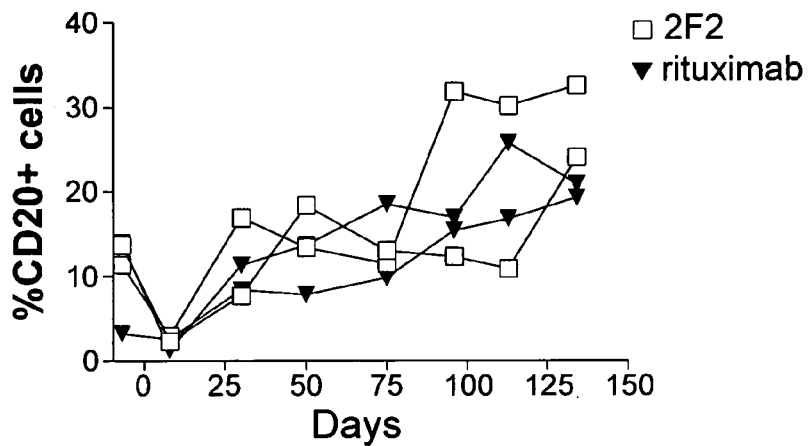
FIGS. 46A-C show flow cytometric analysis of $CD20^+$ cells in lymph node of cynomolgus monkeys following intravenous administration of 2F2 or rituximab at different dosages, 4×1.25 mk/kg (A), 4×6.25 mg/kg (B), or 4×12.50 mg/kg (C).
Figure 46B:
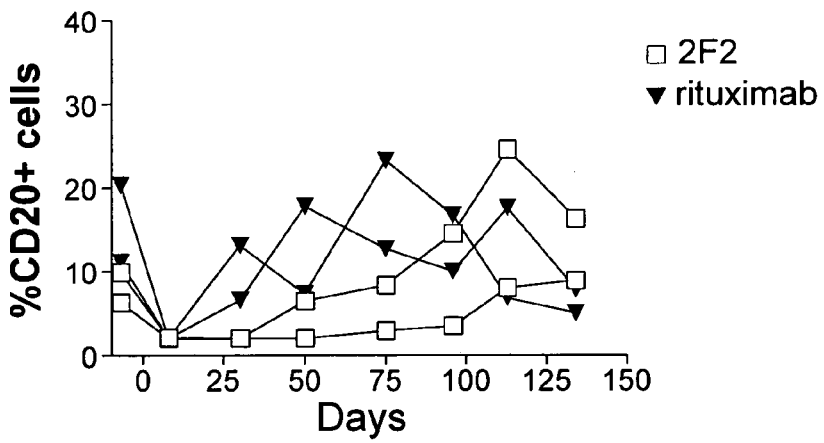
Figure 46C:
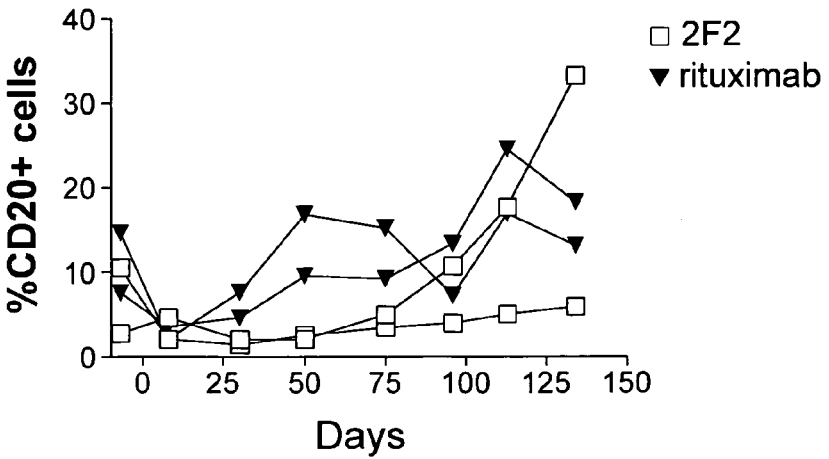

There were no adverse clinical signs or any findings that were considered to be related to treatment with 2F2 or rituximab. FIGS. 44 and 45 shows the flow cytometry analysis of CD20 and CD21 expressing cells in peripheral blood of treated animals, respectively. FIG. 46 shows the flow cytometry analysis of CD20 expressing cells in lymph nodes. Together, both phenotypes analysed during the study indicate a strong and efficient B cell depletion after administration of 2F2 and rituximab at 6.25 mg/kg/day (25 mg/kg in total) and 12.5 mg/kg/day (50 mg/kg in total). In addition, data shows that repopulation of CD20 expressing cells in the lymph nodes and peripheral blood of 2F2 treated animals restarted approximately at day 75 post dosing of 25 mg/kg and 50 mg/kg, i.e., markedly later than in rituximab treated animals.

Figure 47A:
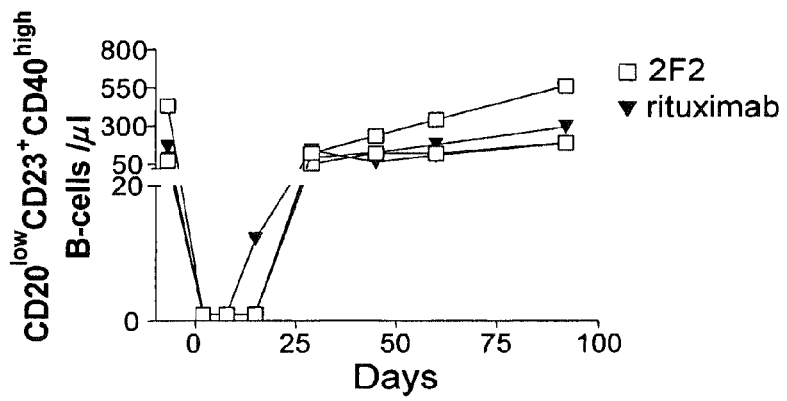
FIGS. 47A-C show flow cytometric analysis of $CD20^{low}CD23^+CD40^{high}$ expressing cells in peripheral blood of cynomolgus monkeys following intravenous administration of 2F2 or rituximab at different dosages, 4×1.25 mk/kg (A), 4×6.25 mg/kg (B), or 4×12.50 mg/kg (C).
Figure 47B:
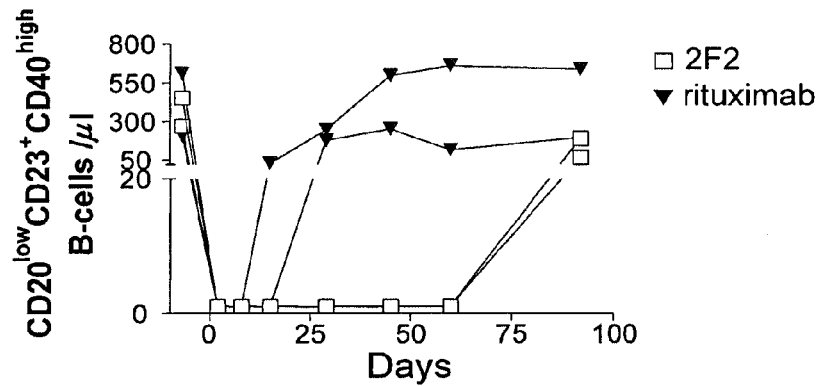
Figure 47C:
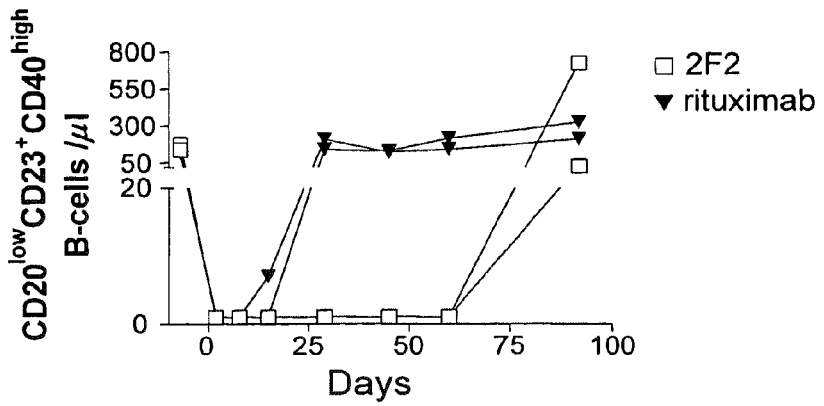

Furthermore, FIGS. 47A-C show the flow cytometric analysis of $CD20^{low}CD23^+CD40^{high}$ expressing cell subpopulations in the peripheral blood (Y. Vugmeyster et al. (2003) Cytometry 52A:101-109).

Peripheral blood cells obtained from either 2F2 or rituximab treated monkeys at dose levels of 1.25 mg/kg (FIG. 47A), 6.25 mg/kg (FIG. 47B), and 12.5 mg/kg (FIG. 47C) once daily by intravenous infusion administrations for 4 consecutive days were incubated with anti-human CD20 FITC murine monoclonal antibody (Coulter) at room temperature for 10 min. Afterwards, count beads were added together with PBS and the cells were washed twice (300 g for 10 min), followed by immediate analysis of $CD20^{low}CD23^+CD40^{high}$ vs. $CD20^{high}CD23^+CD40^{low}$ expressing cell subpopulation in a flow cytometer (Beckman Coulter). Results of $CD20^{low}CD23^+CD40^{high}$ cells shown are expressed as cells per μl. As can be seen from the FIG. 47 2F2 was capable of inducing a complete and longer depletion of $CD20^{low}CD23^+CD40^{high}$ expressing cells compared to rituximab.

Example 14

Epitope Mapping Using Site-directed Mutagenesis

Epitope mapping studies using a mutagenesis approach have indicated that alanine at position 170 (A170) and proline at position 172 (P172) in the second extracellular loop are critical for the recognition of human CD20 by known anti-CD20 antibodies. In studies by Deans and colleagues (M. J. Polyak, et al., Blood, (2002) 99(9): pp 3256-3262; M. J. Polyak, et al., J. Immunol., (1998) 161(7): pp 3242-3248) the binding of all anti-CD20 mAbs tested was abrogated by changing A170 and P172 into the corresponding murine CD20 residues S170 and S172. Some heterogeneity in the recognition of the A×P epitope has been recognized however as most antibodies like rituximab recognize murine CD20 with S170 and S172 mutated to the human A170×P172 sequence whereas some others require additional mutations immediately N-terminal of the A×P sequence. To verify whether the A170×P172 motive is also important for the binding of the antibodies according to the invention the A×P sequence was mutated into S×S using site-directed mutagenesis (A×P mutant=A170S, P172S), cells were transfected with the A×P mutant and wild-type (WT) CD20 DNA, and the binding characteristics of the anti-CD20 mAbs were compared.

Further mutants were prepared, P172S (proline at position 172 mutated to serine), N166D (asparagine at position 166 mutated to aspartic acid), and N163D (asparagine at position 163 mutated to aspartic acid), using site-directed mutagenesis to evaluate whether the mutated amino acid residues are important for binding of the antibodies of the invention. To examine this, a CD20 expression vector was constructed by amplifying the CD20 coding sequence using suitable primers introducing restriction sites and an ideal Kozak sequence for optimal expression. The amplified fragment was digested and ligated in the expressions vector pEE13.4. After transformation in E. coli, colonies were screened for inserts and two clones were selected for sequencing to confirm the correct sequence. The construct was named pEE13.4CD20HS.

Mutagenesis was performed to introduce the AxP mutation and to introduce 20 mouse mutations in the extracellular loop regions of human CD20. Mutagenesis was checked by restriction enzyme digestion and sequencing. The constructs were transiently transfected in CHO cells (for AxP mutations) or HEK293F cells and analyzed 24 or 48 hours post-transfection using flow cytometry.

Oligonucleotide PCR Primers: Oligonucleotide primers were synthesized and quantified by Isogen BV (Maarssen, The Netherlands). Primers were reconstituted in water in a concentration of 100 pmol/µl and stored at −20° C. until required. A summary of PCR and sequencing primers is shown in Table 3.

Optical density determination of nucleic acids: Optical density was determined using an Ultrospec 2100 pro Classic (Amersham Biosciences, Uppsala, Sweden) according to the manufacturer's instructions. The DNA concentration was measured by analysis of the $OD_{260nm}$, where one $OD_{260nm}$ unit=50 µg/ml. The reference solution was identical to the solution used to dissolve the nucleic acids.

Plasmid DNA isolation from *E. coli* culture: Plasmid DNA was isolated from *E. coli* cultures using kits from Qiagen according to the manufacturer's instructions (Westburg BV, Leusden, The Netherlands). For 'bulk' plasmid preparation either a Hi-Speed plasmid Maxi kit or a Hi-Speed plasmid Midi kit were used (Qiagen). For a small scale plasmid preparation (i.e., 2 ml of *E coli* culture) a Qiaprep Spin Miniprep Kit (Qiagen) was used and the DNA eluted in 50 µl TE (Tris-HCl 10 mM pH 8.0, EDTA 1 mM).

PCR amplification: PCR reactions were performed according to the manufacturer's instructions for the Pfu-Turbo© Hotstart DNA polymerase (Stratagene, Amsterdam, The Netherlands). Each 20 µl reaction contained 1×PCR reaction buffer, 200 µM mixed dNTPs, 6.7 pmol of each forward and reverse primer, approximately 1 ng template DNA and 1 unit of Pfu-Turbo© Hotstart DNA polymerase. PCR reactions were performed on a T-gradient Thermocycler 96 (Biometra GmbH, Goettingen, Germany) using a 30 cycle program of: +95° C. for 2 min, followed by 30 cycles of: +95° C. for 30 sec, anneal: a gradient of 45-65° C. for 30 sec and extension: +72° C. for 2 min, followed by a final extension step of 10 min at 72° C. and subsequent storage at 4° C. The completed reactions were analysed by agarose gel electrophoresis.

Agarose gel electrophoresis: Agarose gel electrophoresis was performed according to Sambrook (Molecular Cloning Laboratory Manual, 3rd edition) using gels of 50 ml, in 1×Tris/acetic acid/EDTA (TAE) buffer. DNA was visualized by the inclusion of ethidium bromide in the gel and observation under UV light. Gel images were recorded by a CCD camera and an image analysis system (GeneGnome; Syngene, Cambridge, UK).

Restriction enzyme digestions: Restriction enzymes were supplied by New England Biolabs (Beverly, Mass.) and used according to the supplier's recommendations. In general, 100 ng was digested with 5 units of enzyme(s) in appropriate buffer in a final volume of 10 µl. Reaction volumes were scaled up as appropriate. Digestions were incubated for a minimum of 60 min at the manufacturer's recommended temperature.

For fragments requiring double digestions with restriction enzymes which have incompatible buffer or temperature requirements, digestions were performed sequentially so as to offer favourable conditions for each enzyme in turn.

Alkaline phosphatase treatment: Shrimp alkaline phosphatase (USB, Cleveland, Ohio) was used according to the supplier's recommendations. Alkaline phosphatase removes 5'-phosphate groups from the ends of DNA fragments thereby preventing self-ligation. This is of particular relevance when self re-ligation of a DNA fragment could result in a replication-competent vector. The enzyme is active in most restriction enzyme buffers and was added as appropriate. After the digestion, the enzyme was inactivated by raising the temperature to 70° C. for 15 min.

Purification of PCR and restriction enzyme reaction products: Purification was carried out using the mini-elute PCR Purification kit (supplied by Qiagen), according to the manufacturer's instructions. Briefly, DNA samples were diluted in 5 volumes of binding buffer I (Qiagen) and loaded onto a mini-elute column within an Eppendorf centrifuge tube. The assembly was centrifuged in a bench-top microcentrifuge. The column was washed twice with buffer II (Qiagen): Following buffer application, the assembly was centrifuged and the flow-through was discarded. The column was dried by centrifugation in the absence of added buffer. DNA was eluted by adding elution buffer to the column and the eluate collected by centrifugation. Isolated DNA was quantified by UV spectroscopy and quality assessed by agarose gel electrophoresis.

Isolation of DNA fragments from agarose gel: Where appropriate (i.e., when multiple fragments were present), digested DNA samples were separated by gel electrophoresis and the desired fragment excised from the gel and recovered using the QIAEX II gel extraction kit (Qiagen), according to the manufacturer's instructions. Briefly, DNA bands were excised from the agarose gel and melted in an appropriate buffer at +55° C. QIAEX II resin was added and incubated for 5 min. QIAEX II resin was pelleted by a short centrifugation step (1 min, 14000 g, RT) and washed twice with 500 µl of wash buffer PE. The final pellet was dried in a hood and DNA was eluted with the appropriate volume of TE and temperature (depending on the size of the DNA).

Ligation of DNA fragments: Ligations were performed with the Quick Ligation Kit (New England Biolabs) according to the manufacturer's instructions. For each ligation, the vector DNA was mixed with approximately 3-fold molar excess of insert DNA such that the total amount of DNA was lower than 200 ng in 10 µl, with volume adjusted with water as appropriate. To this was added 10 µl 2×Quick Ligation Buffer and 1 µl Quick T4 DNA ligase and the ligation mix was incubated for 5-30 min at room temperature.

Transformation of DNA into bacteria: Samples of DNA were used to transform One Shot DH5α-T1R competent *E. coli* cells (Invitrogen, Breda, The Netherlands) using the heat-shock method according to the manufacturer's instructions. Briefly, 1-5 µl of DNA solution (typically 2 µl of DNA ligation mix) was added to an aliquot of transformation-competent bacterial cells and the mixture incubated on ice for 30 min. The cells were then heat-shocked by transferring to a waterbath at 42° C. for 30 sec followed by a further incubation on ice for 5 min. Cells were left to recover by incubation in a non-selective culture medium (SOC) for 1 hour with agitation at 37° C. and were subsequently spread onto agar plates containing appropriate selective agent (ampicillin at 50 µg/ml). Plates were incubated for 16-18 hours at +37° C. or until colonies of bacteria became evident.

Screening of bacterial colonies by PCR: Bacterial colonies were screened for the presence of vectors containing the desired sequences using the PCR colony screening technique. 20 µl of PCR reaction mix containing 0.5 volumes of HotStarTaq Master Mix (Qiagen), 4 pmol of the forward and reverse primers and completed with water was added to a PCR tube. A colony was lightly touched with a 20 µl pipet tip, once touched in 2 ml LB in a culture tube (for growing bacteria containing the corresponding plasmid) and resuspended in the 20 μl PCR mix. PCR was performed on a T-gradient Thermocycler 96 (Biometra) using a 35 cycle program of: +95° C. for 15 min, followed by 35 cycles of: +94° C. for 30 sec, anneal: 55° C. for 30 sec and extension: +72° C. for 2 min, followed by a final extension step of 10 min at 72° C. and subsequent storage at 4° C. The completed reactions were analyzed by agarose gel electrophoresis. See Table 3 for details of primer pairs used for colony PCR.

DNA sequencing: Plasmid DNA samples were send to AGOWA (Berlin, Germany) for sequence analysis. Sequences were analyzed using the VectorNTI software package (Informax, Frederick, Md., USA).

DNA combined with the diluted lipofectamine. After gently mixing and incubating the solution (RT, 20 min), 1000 μl DNA/lipofectamine was added to the CHO cells, thoroughly mixed and incubated for 48 hours at 37° C., 5% $CO_2$. Two days after transfection of CHO cells, cells were washed twice with FACS buffer (PBS supplemented with 0.1% BSA and 0.002% $NaN_3$). CHO cells were treated with trypsin/EDTA (Gibco BRL, Life Technologies, Paisley, Scotland) and lifted off the culture plates.

Anti-CD20 Antibody binding: HEK293F cells and CHO cells were taken up in PBS in a concentration of $2 \times 10^6$/ml, and added to round bottom plates ($1 \times 10^5$/well). Then, 50 μl

TABLE 3

| Name | Application | Length | Oligo Sequence | SEQ ID NOs |
|---|---|---|---|---|
| CD20P172S | CD20 mutagenesis | 36 | TGGGGAGTTTTTCTCAGAGGAATTC-GATGGTTCACAGTTGTA | SEQ ID NO: 58 |
| CD20N166D | CD20 mutagenesis | 39 | TGTAACAGTATTGGGTAGATGGG | SEQ ID NO: 59 |
| CD20N163D | CD20 mutagenesis | 36 | AATCATGGACATACTTAATATTA | SEQ ID NO: 60 |
| cd20exfor | CD20 construction | 41 | TATAGCCCGGGGCCGCCACCATGACAACACCCAGAAATTCA | SEQ ID NO: 61 |
| cd20exrev | CD20 construction | 38 | GCGTCTCATGTACATTAAGGAGAGCTGTCATTTTCTAT | SEQ ID NO: 62 |
| pee13.4seqrev2 | Colony PCR | 23 | TCGGACATCTCATGACTTTCTTT | SEQ ID NO: 63 |
| pConKseq1 | Colony PCR | 23 | GTAGTCTGAGCAGTACTCGTTGC | SEQ ID NO: 64 |
| cd20hsapmutr (AxP) | CD20 mutagenesis | 42 | TGGGGAGTTTTTCTCAGAGGAATTC-GATGGTTCACAGTTGTA | SEQ ID NO: 65 |
| cd20hsapmutf (AxP) | CD20 mutagenesis | 42 | TACAACTGTGAACCATCGAATTCCTCT-GAGAAAAACTCCCCA | SEQ ID NO: 66 |
| CD20seq2 | CD20 sequencing | 23 | TGTAACAGTATTGGGTAGATGGG | SEQ ID NO: 67 |
| cd20seq1 | CD20 sequencing | 23 | AATCATGGACATACTTAATATTA | SEQ ID NO: 68 |

Mutagenesis: The mutagenesis was performed, using either the QuikChange® XL Site-Directed Mutagenesis kit (Cat 200517-5, Lot 1120630, Stratagene Europe) according to the manufacturer's instructions.

Mutagenesis reactions were concentrated using ethanol precipitation and transformed into either oneshot DH5α-T1R competent *E. coli* cells or electroporated into ElectroTen-Blue® Electroporation-Competent Cells. Colonies were checked by colony PCR and restriction digestion prior to transfection.

HEK293F cell transfection: HEK293F cells were obtained from Invitrogen and transfected according to the manufacturer's instructions, using 293fectin. The HEK293F cells were used for all the single mutant sequences.

CHO cell transfection: CHO cells grown to approximately 95% confluence were transiently transfected with CD20 wild-type, mutant cDNA or a combination of both constructs using lipofectamine 2000 (M668-019, Invitrogen, Breda, Netherlands). To this end, 24 μg precipitated DNA was diluted (1 μg/μl) in 500 μl optimem, in ratios of AxP 100%: WT 0%; AxP 33.3%: WT 66.6%; AxP 66.6%: WT 33.3%; AxP 0%: WT 100%. For each transfection 24 μl lipofectamine was diluted in 500 μl optimem. Then, the diluted lipofectamine was incubated (RT, 5 min), and the diluted CD20 mAb was added, in serial dilutions of 10, 5, 2.5, or 0 μg per well (4° C., 30 min). After washing in FACS buffer (PBS supplemented with 0.1% BSA and 0.002% $NaN_3$), the cells were analyzed on a flow cytometer (Becton Dickinson, San Diego, Calif., USA), and 5,000 events per sample were acquired at high flow rate.

Figure 48A:
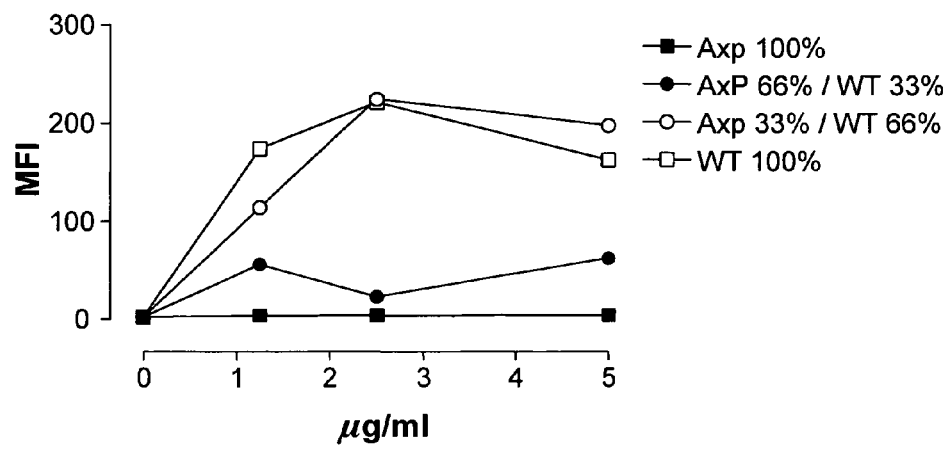
FIGS. 48A-E show binding of rituximab (A), 2F2 (B), 11B8 (C), B1 (D), or an isotype control antibody (E) to CHO cells expressing wild type (WT) CD20, mutant CD20 (A×P), or both WT CD20 and mutant CD20 (A×P) as determined by flow cytometry.
Figure 48B:
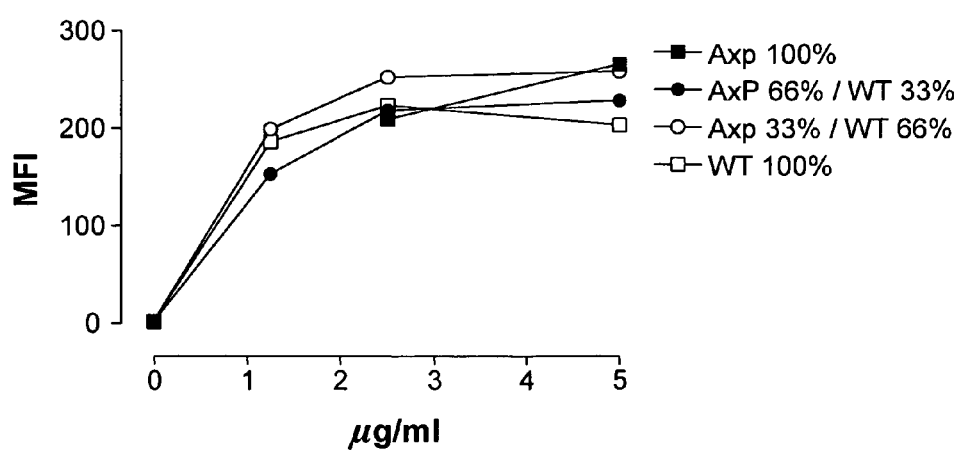
Figure 48C:
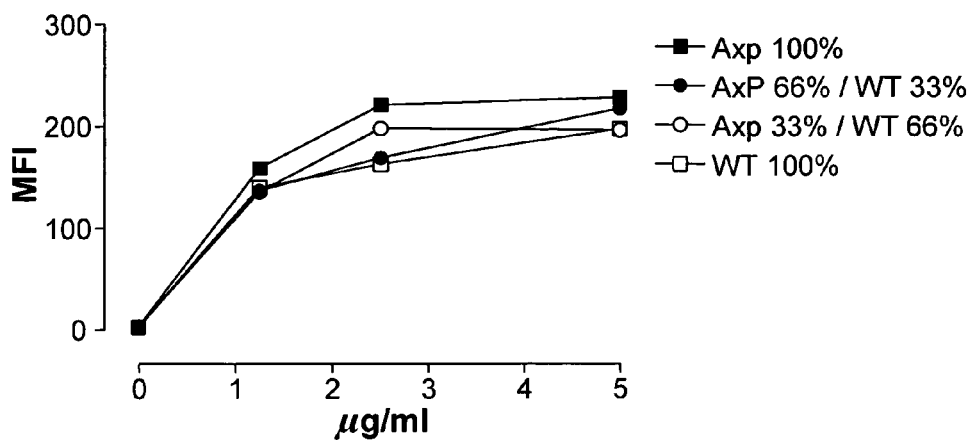
Figure 48D:
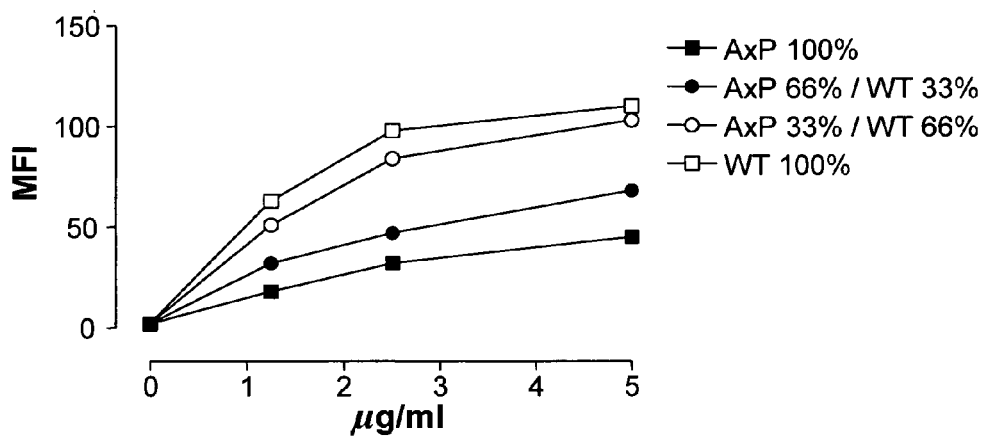
Figure 48E:
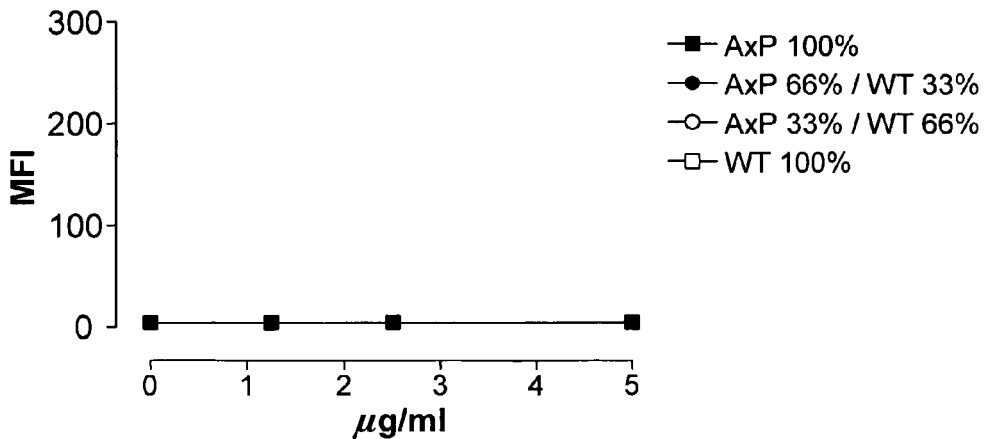

As can be seen from FIGS. 48A-E, all anti-CD20 mAbs bound efficiently to CHO cells expressing WT CD20. As expected, rituximab did not bind the AxP mutant (FIG. 48A), and B1 bound this mutant poorly (FIG. 48D). Both 2F2 and 11B8 in contrast bound to WT and AxP mutant CD20 equally well (FIG. 48B and FIG. 48C). Titrating the amount of WT CD20 on the surface indeed titrated the binding of rituximab and B1. Both 2F2 and 11B8 again were insensitive to the absence or presence of the mutation.

This study indicates that the binding of 2F2 and 11B8 to human CD20 is insensitive to mutations at amino acid positions 170 and 172. 2F2 and 11B8 therefore represent a new class of CD20 mAbs recognizing a novel CD20 epitope.

Figure 49A:
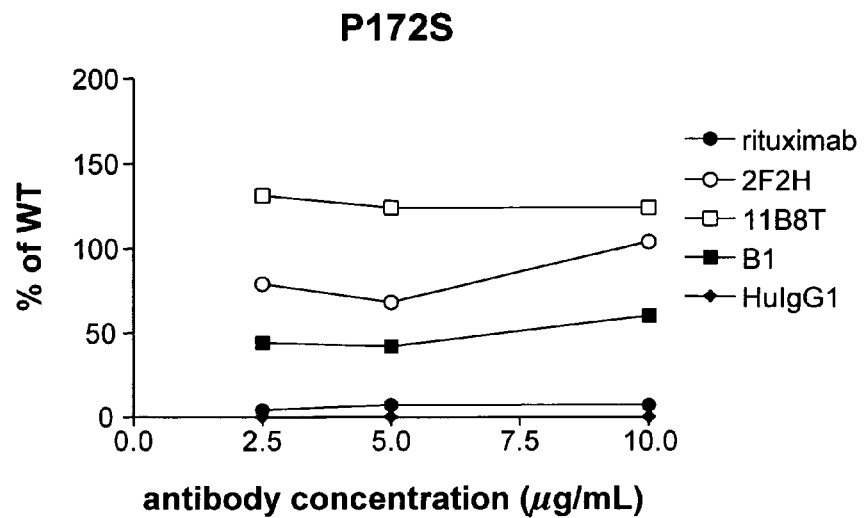
FIGS. 49A-F show percentage binding of 2F2, 11B8T, B1 or rituximab to mutant P172S vs. WT CD20 (A), percentage binding of 2F2T, 11B8T, B1, CAT (CAT 13.6E12, a mouse monoclonal IgG2A anti-CD20 antibody, Diatec.Com), a control isotype antibody (KLH) or rituximab to mutant CD20 (A×P) vs. WT CD20 (B), percentage binding of 2F2, 11B8T, B1 or rituximab to mutant N166D vs. WT CD20 (C), percentage binding of 2F2T, CAT or rituximab to mutant N166D vs. WT CD20 (D), percentage binding of 2F2T, 2F2, 11B8T, B1 or rituximab to mutant N163D vs. WT CD20 (E), and percentage binding of 2F2T, CAT or rituximab to mutant N163D vs. WT CD20 (F).
Figure 49B:
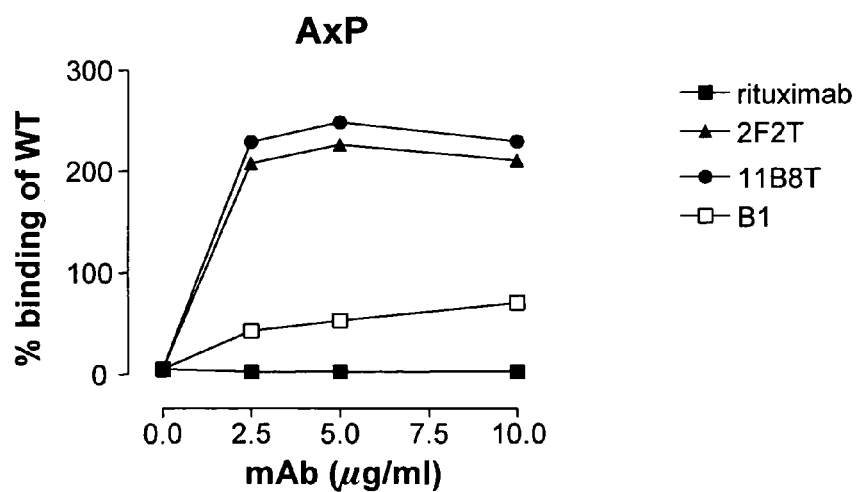

FIG. 49A shows percentage binding of 2F2, 11B8T, B1 or rituximab to mutant P172S vs. WT CD20, FIG. 49B shows percentage binding of 2F2T, 11B8T, B1, CAT (CAT 13.6E12, a mouse monoclonal IgG2A anti-CD20 antibody, Diatec.Com), a control isotype antibody (KLH), or rituximab to mutant CD20 (AxP) vs. WT CD20.

Figure 49C:
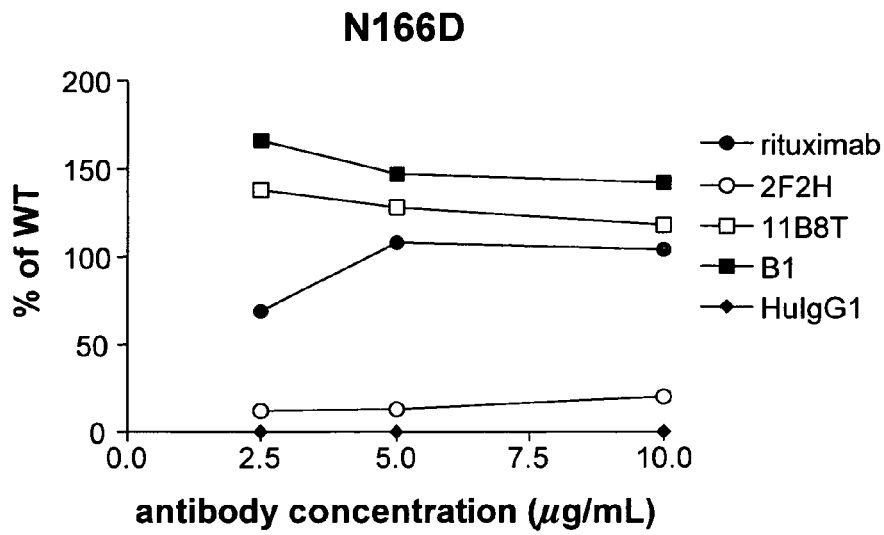
Figure 49D:
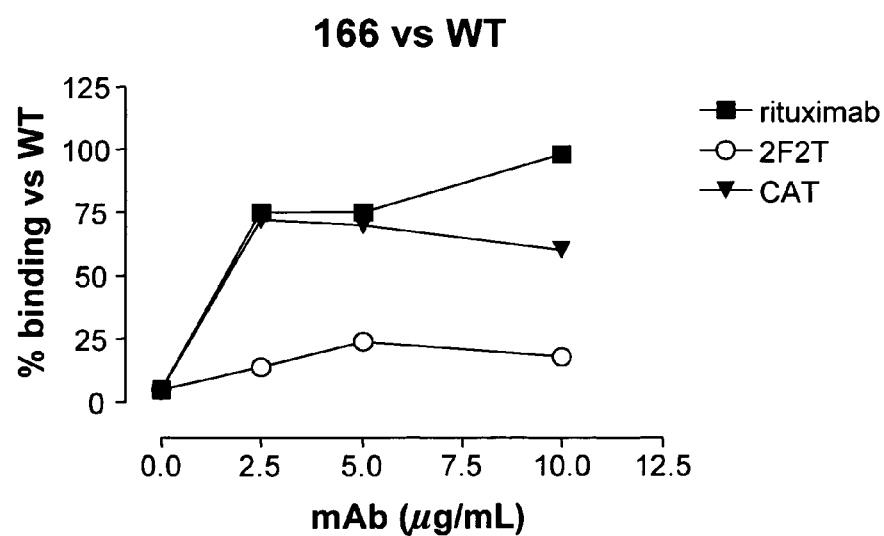
Figure 49E:
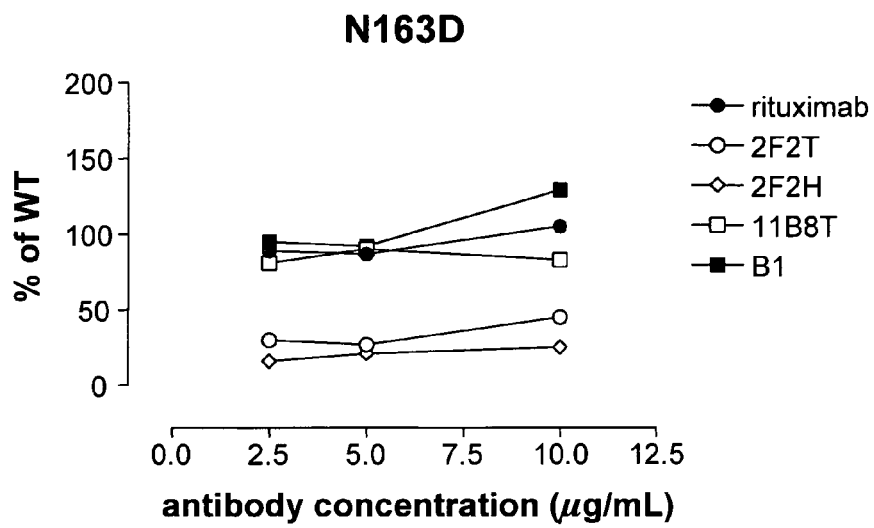
Figure 49F:
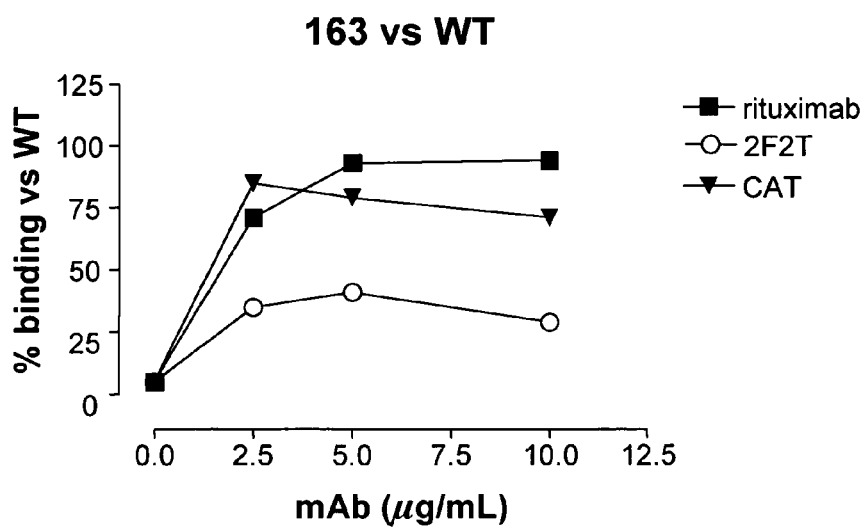

For the mutant wherein asparagine at position 166 has been replaced with aspartic acid (CD20N166D) 2F2 showed very low binding, whereas B1, rituximab and 11B8T were able to bind, see FIG. 49C. In a similar experiment CAT 13.6E12 and rituximab were able to bind to CD20N166D, whereas 2F2T only showed very low binding, see FIG. 49D. For the mutant wherein asparagine at position 163 has been replaced by aspartic acid (CD20N163D) again rituximab, 11B8T, and B1 were able to bind to CD20N163D, whereas 2F2 and 2F2T only showed very low binding, see FIG. 49E. In a similar experiment CAT 13.6E12 and rituximab were able to bind to CD20N163D, whereas 2F2T only showed very low binding, see FIG. 49F.

These experiments indicate that 2F2 and 11B8 bind to different epitopes.

Example 15

Epitope Mapping Using Pepscan Method

Synthesis of peptides: 7-, 9-, and 15-mer peptides were synthesized according to standard methods. In some cases chemical linkage of the legs of a 15-mer peptide helps to identify amino acid sequences of a potentially discontinuous epitope. According to known procedures (H. M. Geysen et al. (1984) *Proc. Natl. Acad. Sci. USA*, 81:3998; J. W. Slootstra et al. (1996) *Mol. Divers.* 1:87; and WO 01/60769), 7-, 9-, and 15-mer peptides were synthesized that could be possible binding sites or epitopes involved in binding of 2F2 or 11B8 to the human CD20 molecule. The 9- and 15-mers were synthesized as loops and screened using credit-card format mini-PEPSCAN cards (455 peptide format/card). In all looped peptides amino acids at varied positions were replaced by a cysteine (e.g., acetyl-XCXXXXXXXXCX-minicard). The peptides were synthesized using standard Fmoc-chemistry and deprotected using TFA with scavengers. Subsequently, the deprotected peptides were reacted on the microarray with an 0.5 mM solution of 1,3-bis(bromomethyl)-benzene in ammonium bicarbonate (20 mM, pH 7.9), supplemented with acetonitrile (1:1 (v/v)). The microarrays were gently shaken in the solution for 30-60 min, while completely covered in the solution. Finally, the microarrays were washed extensively with excess of Millipore $H_2O$ and sonicated in disrupt-buffer containing 1% sodium dodecyl-sulfate, 0.1% β-mercaptoethanol, in PBS (pH 7.2) at 70° C. for 30 min, followed by sonication in millipore $H_2O$ for another 45 min. Subsequently, the microwells were ready for screening in an ELISA-assay.

Pepscan ELISA-assay: The 455-well credit card-format polyethylene cards, containing the covalently linked peptides, were incubated with serum (diluted 1:1000 in blocking solution which contains 5% horse serum (v/v) and 5% ovalbumin (w/v)) (4° C., over night). After washing, the peptides were incubated with anti-human antibody peroxidase (dilution 1:1000, 1 hour, 25° C.), and after washing the peroxidase substrate, 2,2'-azino-di-3-ethylbenzthiazolin sulfonate and 2 µl/ml 3% $H_2O_2$ were added. After one hour, the color development was measured. The color development of the ELISA was quantified with a CCD-camera and an image processing system. The set up consists of a CCD-camera and a 55 mm lens (Sony CCD Video Camera XC-77RR, Nikon micro-nikk or 55 mm f/2.8 lens), a camera adaptor (Sony Camera adaptor DC-77RR) and the Image Processing Software package Optimas, version 6.5 (Media Cybernetics, Silver Spring, Md. 20910, U.S.A.). Optimas runs on a pentium II computer system.

The absorbances (OD values) for the peptides at different antibody concentrations are shown in below Table 4 and Table 5.

TABLE 4

| | | mABs | | | | | | | | |
|---|---|---|---|---|---|---|---|---|---|---|
| | SEQ ID NOs | 11B8 10 µg/ml | 11B8 100 µg/ml | 7D8 10 µg/ml | 7D8 100 µg/ml | rituximab 10 µg/ml | 2F2 10 µg/ml | 2F2 100 µg/ml | B1 10 µg/ml | B1 100 µg/ml |
| KMECLNFIRAHCPYI | SEQ ID NO:69 | 763 | 2997 | 134 | 41 | 90 | 48 | 66 | 147 | 304 |
| LKMECLNFIRCHTPY | SEQ ID NO:70 | 165 | 738 | 160 | 41 | 120 | 49 | 87 | 179 | 216 |
| KMESCNFIRACTPYI | SEQ ID NO:71 | 625 | 3090 | 142 | 52 | 123 | 39 | 78 | 170 | 308 |
| MESLCFIRAHCPYIN | SEQ ID NO:72 | 179 | 956 | 127 | 55 | 102 | 41 | 65 | 119 | 178 |
| CFIRAHTPC | SEQ ID NO:73 | 188 | 534 | 181 | 69 | 134 | 91 | 114 | 170 | 212 |
| CIRAHTPYC | SEQ ID NO:74 | 151 | 449 | 186 | 60 | 132 | 57 | 92 | 151 | 195 |
| CRAHTPYIC | SEQ ID NO:75 | 427 | 1605 | 188 | 64 | 145 | 48 | 87 | 179 | 216 |
| CAHTPYINC | SEQ ID NO:76 | 179 | 452 | 174 | 65 | 125 | 42 | 106 | 161 | 172 |
| IPAGIYA | SEQ ID NO:77 | 217 | 950 | 164 | 76 | 177 | 48 | 85 | 165 | 192 |
| PAGIYAP | SEQ ID NO:78 | 449 | 2501 | 170 | 64 | 111 | 43 | 85 | 165 | 300 |
| AGIYAPI | SEQ ID NO:79 | 251 | 2207 | 188 | 73 | 110 | 44 | 98 | 187 | 143 |
| GIYAPIC | SEQ ID NO:80 | 99 | 251 | 152 | 64 | 141 | 34 | 93 | 177 | 147 |
| IYAPICV | SEQ ID NO:81 | 137 | 313 | 174 | 58 | 159 | 58 | 99 | 175 | 90 |
| GIYAPIA | SEQ ID NO:82 | 172 | 857 | 177 | 96 | 156 | 62 | 96 | 165 | 121 |
| IYAPIAV | SEQ ID NO:83 | 161 | 654 | 181 | 58 | 116 | 62 | 76 | 161 | 106 |

TABLE 5

| | | mABs | | | |
|---|---|---|---|---|---|
| Amino Acid Sequence | SEQ ID NOs | 11B8 10 µg/ml | 7D8 10 µg/ml | rituximab 10 µg/ml | 2F2 10 µg/ml |
| PCINIYNAEPANPCE | SEQ ID NO:84 | 118 | 163 | 152 | 65 |
| YCNIYNAEPANPSCK | SEQ ID NO:85 | 287 | 181 | 2418 | 86 |
| ICIYNAEPANPSECN | SEQ ID NO:86 | 138 | 192 | 142 | 78 |

TABLE 5-continued

| Amino Acid Sequence | SEQ ID NOs | mABs | | | |
|---|---|---|---|---|---|
| | | 11B8 10 µg/ml | 7D8 10 µg/ml | rituximab 10 µg/ml | 2F2 10 µg/ml |
| NCYNAEPANPSEKCS | SEQ ID NO:87 | 93 | 121 | 2649 | 49 |
| ICNAEPANPSEKNCP | SEQ ID NO:88 | 115 | 165 | 3283 | 43 |
| YCAEPANPSEKNSCS | SEQ ID NO:89 | 106 | 188 | 3770 | 65 |
| NCEPANPSEKNSPCT | SEQ ID NO:90 | 159 | 183 | 3476 | 61 |
| ACPANPSEKNSPSCQ | SEQ ID NO:91 | 146 | 148 | 250 | 77 |
| ECANPSEKNSPSTCY | SEQ ID NO:92 | 134 | 179 | 188 | 68 |

As appears from Table 4, 11B8 showed binding to AGIYAP (SEQ ID NO:93) of the small first extracellular loop of human CD20 at both 10 µg/ml and 100 µg/ml, whereas the other antibodies tested did not show significant binding to AGIYAP (SEQ ID NO:93).

Furthermore, 11B8 showed binding to MESLNFIRAHTPYI (SEQ ID NO:94) of the second extracellular loop of human CD20 at both 10 µg/ml and 100 µg/ml, whereas the other antibodies tested did not show significant binding to MESLNFIRAHTPYI (SEQ ID NO:94).

As appears from Table 5, rituximab showed binding to EPANPSEK (SEQ ID NO:95) of the second extracellular loop of human CD20 at both 1 µg/ml and 10 µg/ml, whereas the other antibodies tested did not show significant binding to EPANPSEK (SEQ ID NO:95).

Example 16

Anti-idiotypic Antibodies

Generation of anti-idiotypic antibodies: Mouse anti-idiotypic antibodies were made by immunizing Ba1b/C mice with 2F2 or 11B8T, and generating hybridomas from spleens of these mice by fusion with NS1 myeloma cells using standard techniques. The following anti-idiotypic antibodies were generated: anti-2F2 sab 1.1, anti-2F2 sab 1.2, anti-2F2 sab 1.3, anti-11B8T sab 2.2, anti-11B8T sab 2.3, anti-sab 2.4, anti-11B8T sab 2.5, and anti-11B8T sab 2.6. These were tested for specific binding to 2F2T, 7D8 and 11B8T. ELISA plates were coated with purified 2F2T, 7D8 or 11B8T (diluted in PBS to a final concentration of 1-2 µg/ml, 37° C., 2 hours). Plates were blocked with PBS containing 0.05% Tween-20 and 2% chicken serum (RT, 1 hour). Subsequently, the plates were incubated with supernatants from cultures of the anti-idiotypic antibodies (final concentration adjusted to 1-10 µg/ml, RT, 2 hours). Bound mouse anti-idiotypic antibodies were detected with rabbit-anti-mouse IgG-HRP conjugated antibody (Jackson ImmunoResearch).

Figure 50:
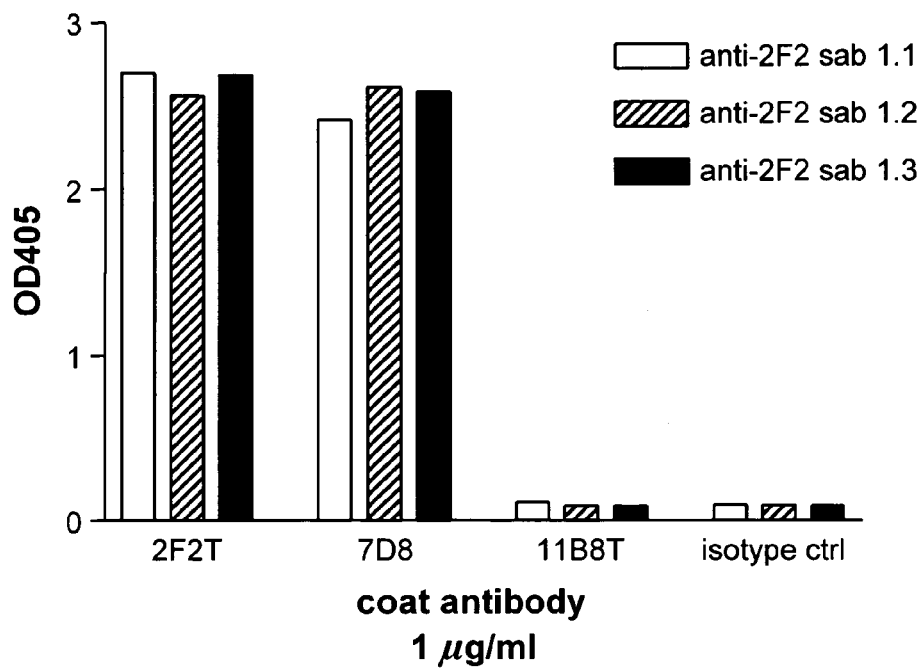
FIG. 50 shows binding of 2F2T, 7D8, and isotype control antibody, as determined by ELISA, to three anti-idiotypic antibodies, anti-2F2 sab 1.1, anti-2F2 sab 1.2, and anti-2F2 sab 1.3, raised against 2F2.

As shown in FIG. 50 anti-2F2 sab 1.1, anti-2F2 sab 1.2, and anti-2F2 sab 1.3 bind to 2F2T and 7D8, but not to 11B8T or an unrelated, isotype control human antibody. Since 2F2T and 7D8 are very homologous in $V_L$ and $V_H$ sequence, reaction of anti-2F2 idiotypic antibodies with 7D8 was expected.

Figure 51:
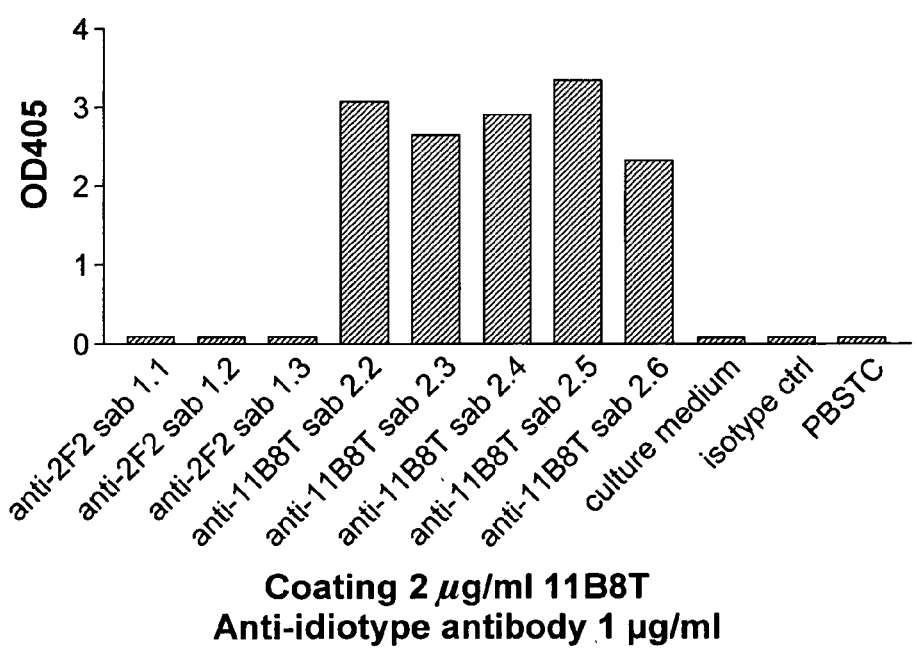
FIG. 51 shows binding of 11B8T, as determined by ELISA, to anti-idiotypic antibodies, anti-11B8T sab 2.2, anti-11B8T sab 2.3, anti-i 11B8T sab 2.4, anti-11B8T sab 2.5, and anti-11B8T sab 2.6, raised against 11B8T, but no binding to the anti-idiotypic anti-2F2 antibodies.

FIG. 51 shows that anti-11B8T sab 2.2, anti-11B8T sab 2.3, anti-11B8T sab 2.4, anti-11B8T sab 2.5, and anti-11B8T sab 2.6 all bind to 11B8T to a similar extent.

Figure 52A:
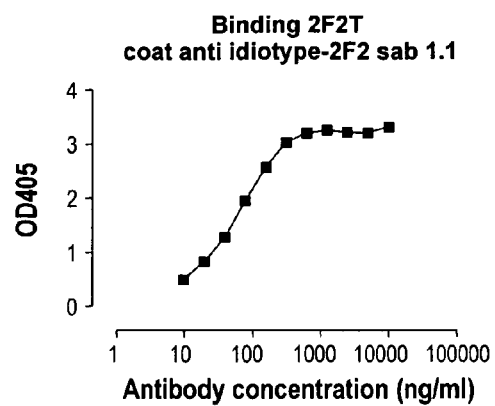
FIGS. 52A-C show dose-dependent binding of 2F2T, as determined by ELISA, to three anti-idiotypic antibodies, anti-2F2 sab 1.1 (A), anti-2F2 sab 1.2 (B), and anti-2F2 sab 1.3 (C), raised against 2F2.
Figure 52B:
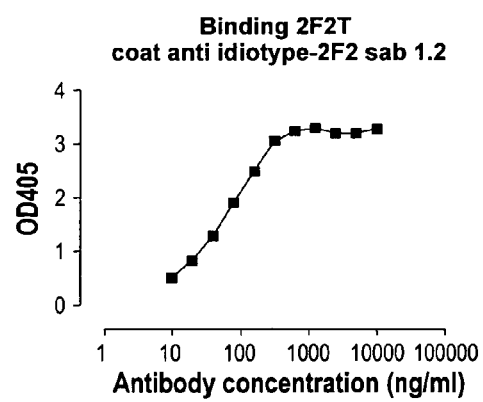
Figure 52C:
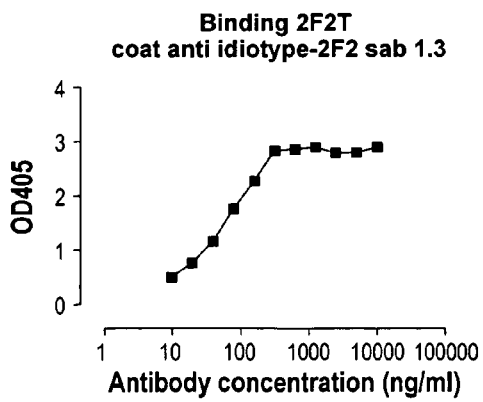

Anti-idiotypic antibodies as an immunodiagnostic tool: The 2F2/7D8 and 11B8T specific anti-idiotypic antibodies can be used as an immunodiagnostic tool to detect and quantify levels of human monoclonal antibodies against CD20 in laboratory or patient samples. This may be useful for examining pharmakokinetics of the anti-CD20 antibody or for determining and adjusting the dosage of the anti-CD20 antibody and for monitoring the disease and the effect of treatment in a patient. As an example of such an assay, ELISA plates were coated with 4 µg/ml anti-2F2 sab 1.1, anti-2F2 sab 1.2 or anti-2F2 sab 1.3. Plates were blocked with PBS containing 0.05% Tween-20 and 2% chicken serum (RT, 1 hour). Subsequently, the plates were incubated with a serial dilution of 2F2T (10,000-9.77 ng/ml, RT, 2 hours). Bound 2F2T was detected with mouse-anti-human IgG HRP-conjugated antibody. As shown in FIGS. 52A-C a dose dependent binding of 2F2T was observed.

Equivalents

Those skilled in the art will recognize or be able to ascertain, using no more than routine experimentation, many equivalents of the specific embodiments of the invention described herein. Such equivalents are intended to be encompassed by the following claims. Any combination of the embodiments disclosed in the dependent claims are also contemplated to be within the scope of the invention.

INCORPORATION BY REFERENCE

All patents, pending patent applications and other publications cited herein are hereby incorporated by reference in their entirety.

We claim:

1. An isolated human monoclonal antibody which binds to human CD20, wherein said antibody is encoded by human heavy chain and human kappa light chain nucleic acids comprising the nucleotide sequences in their variable regions as set forth in SEQ ID NO:1 and SEQ ID NO:3, respectively.

2. An isolated human monoclonal antibody which binds to human CD20, wherein said antibody has human heavy chain and human kappa light chain variable regions comprising the amino acid sequences as set forth in SEQ ID NO:2 and SEQ ID NO:4, respectively.

3. A hybridoma which produces a human monoclonal antibody encoded by human IgG heavy chain and human kappa light chain nucleic acids comprising nucleotide sequences in their variable regions as set forth in SEQ ID NO:1 and SEQ ID NO:3, respectively.

4. A hybridoma which produces a human monoclonal having IgG heavy chain and kappa light chain variable regions which comprise the amino acid sequences as set forth in SEQ ID NO:2 and SEQ ID NO: 4, respectively.

5. A composition comprising a first human antibody and a second human antibody, both of which bind to human CD20, wherein the first antibody has human heavy chain and human kappa light chain variable regions comprising the amino acid sequences as set forth in SEQ ID NO:2 and SEQ ID NO:4, respectively, and wherein the second antibody has human heavy chain and human kappa light chain variable regions comprising the amino acid sequences as set forth in SEQ ID NO:10 and SEQ ID NO:12, respectively.

* * * * *

UNITED STATES PATENT AND TRADEMARK OFFICE
CERTIFICATE OF CORRECTION

PATENT NO. : 8,529,902 B2
APPLICATION NO. : 10/687799
DATED : September 10, 2013
INVENTOR(S) : Teeling et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2728 days.

Signed and Sealed this
Twenty-first Day of July, 2015

Michelle K. Lee
*Director of the United States Patent and Trademark Office*